(12) United States Patent
Tomono et al.

(10) Patent No.: US 7,934,703 B2
(45) Date of Patent: May 3, 2011

(54) MIST GENERATOR AND MIST EMISSION RENDERING APPARATUS

(75) Inventors: Akira Tomono, Kanagawa (JP); Akio Uehara, Kanagawa (JP)

(73) Assignee: Akira Tomono, Hiratsuka (JP)

( * ) Notice: Subject to any disclaimer, the term of this patent is extended or adjusted under 35 U.S.C. 154(b) by 536 days.

(21) Appl. No.: 11/886,020

(22) PCT Filed: Mar. 9, 2006

(86) PCT No.: PCT/JP2006/004604
§ 371 (c)(1),
(2), (4) Date: Mar. 20, 2008

(87) PCT Pub. No.: WO2006/095816
PCT Pub. Date: Sep. 14, 2006

(65) Prior Publication Data
US 2008/0223953 A1   Sep. 18, 2008

(30) Foreign Application Priority Data

Mar. 11, 2005 (JP) .................................. 2005-068712
Oct. 12, 2005 (JP) .................................. 2005-297125
Dec. 6, 2005 (JP) .................................. 2005-351800

(51) Int. Cl.
*B01F 3/04* (2006.01)
(52) U.S. Cl. ........... 261/18.1; 261/26; 261/81; 261/127; 261/DIG. 48; 261/DIG. 65
(58) Field of Classification Search ............. 261/18.1, 261/26, 81, 127, 152, DIG. 48, DIG. 65; 239/4, 102.1, 102.2; 128/200.16
See application file for complete search history.

(56) References Cited

U.S. PATENT DOCUMENTS

| | | | | | |
|---|---|---|---|---|---|
| 3,387,607 | A | * | 6/1968 | Gauthier et al. | 128/200.16 |
| 3,561,444 | A | * | 2/1971 | Boucher | 128/200.16 |
| 3,901,443 | A | * | 8/1975 | Mitsui et al. | 239/102.2 |
| 4,123,481 | A | * | 10/1978 | Herold et al. | 261/81 |
| 4,410,139 | A | * | 10/1983 | Nishikawa et al. | 239/102.2 |
| 4,640,804 | A | * | 2/1987 | Mizoguchi | 261/81 |
| 4,783,006 | A | * | 11/1988 | Hayashi et al. | 239/380 |
| 5,217,165 | A | * | 6/1993 | Takahashi et al. | 239/102.2 |
| 5,485,828 | A | | 1/1996 | Hauser | 128/200.16 |
| 5,645,769 | A | * | 7/1997 | Tamaru et al. | 261/30 |
| 5,918,804 | A | * | 7/1999 | Jung | 236/44 A |
| 6,536,746 | B2 | * | 3/2003 | Watkins | 261/26 |
| 2005/0167860 | A1 | * | 8/2005 | Brooks | 261/81 |

FOREIGN PATENT DOCUMENTS

| | | | | |
|---|---|---|---|---|
| FR | 2690510 A1 | * | 10/1993 | 128/200.16 |
| JP | 54-082707 | | 7/1979 | |
| JP | P S54-82707 A | | 7/1979 | |
| JP | U 55-2454 | | 1/1980 | |
| JP | U S55-2454 U | | 1/1980 | |

(Continued)

*Primary Examiner* — Richard L Chiesa
(74) *Attorney, Agent, or Firm* — Maschoff Gilmore & Israelsen

(57) ABSTRACT

An apparatus includes an ultrasonic transducer; an ultrasonic propagation medium disposed so as to fill a plane of vibration of the transducer; liquid retaining means disposed so as to be in contact with an end face of the medium; and an ultrasonic focusing reflecting mechanism disposed in an ultrasonic propagation path, thereby the apparatus attains discharging into air and atomization of the liquid by use of ultrasonic waves. Atomization efficiency is enhanced by the use of an ultrasonic reflection tube, and mist emission is carried out. Use is made of a compact liquid container equipped at its bottom with an ultrasonic transmission membrane. Various types of liquids can be atomized by changing the direction of ultrasonic course.

6 Claims, 28 Drawing Sheets

FOREIGN PATENT DOCUMENTS

Figure 1:
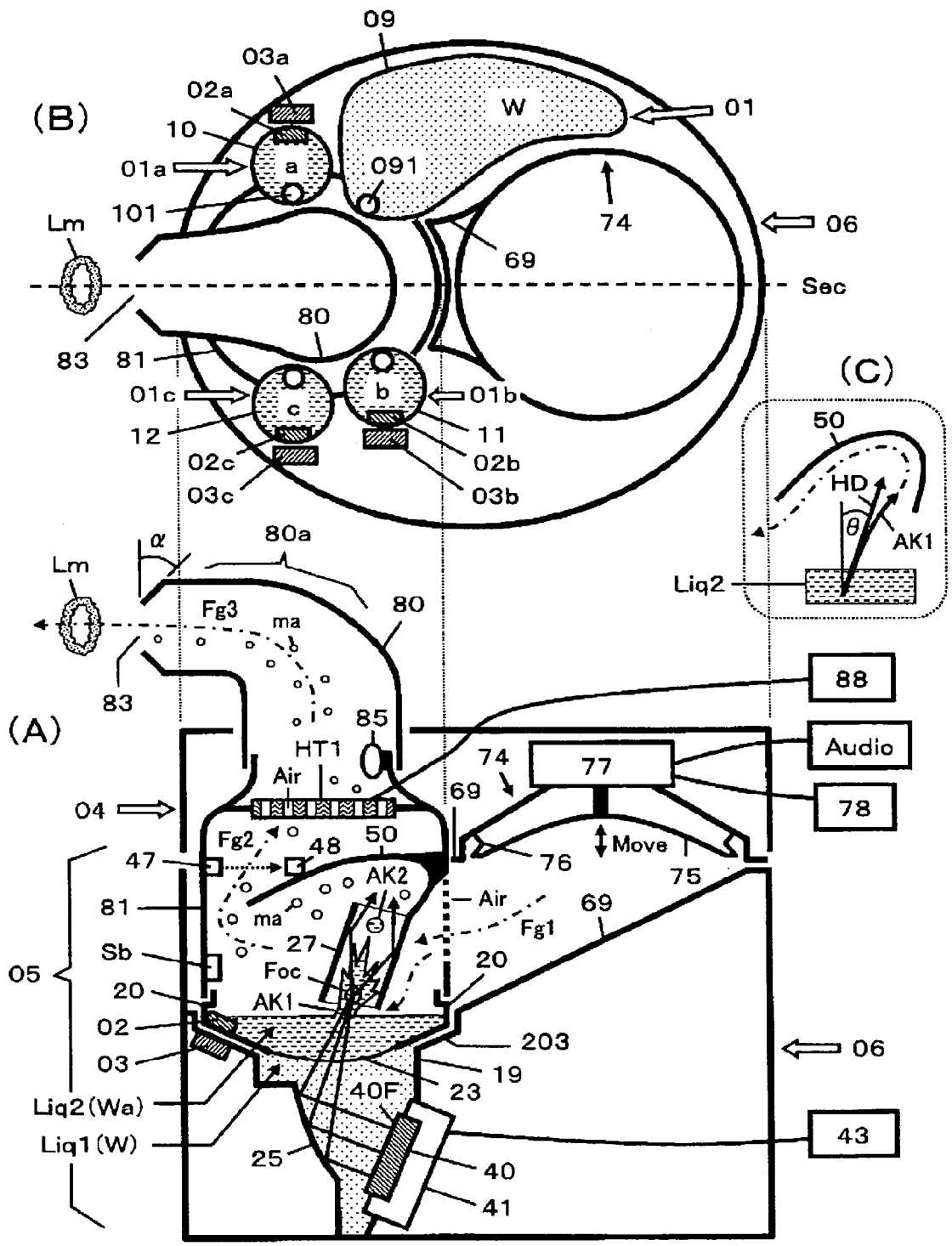

| | | | |
|---|---|---|---|
| JP | U 58-8034 | 1/1983 | |
| JP | U S58-8034 U | 1/1983 | |
| JP | U 63-198933 | 12/1988 | |
| JP | U S63-198933 U | 12/1988 | |
| JP | 1-312336 A * | 12/1989 | ............ 261/DIG. 48 |
| JP | U 2-104872 | 8/1990 | |
| JP | U H02-104872 U | 8/1990 | |
| JP | 03-065264 | 3/1991 | |
| JP | P H03-65264 A | 3/1991 | |
| JP | 3-225133 A * | 10/1991 | ............ 261/DIG. 48 |
| JP | 6-64760 | 9/1994 | |
| JP | 6-507836 | 9/1994 | |
| JP | P H06-507836 A | 9/1994 | |
| JP | U H06-64760 U | 9/1994 | |
| JP | 07-213968 | 8/1995 | |
| JP | P H07-213968 A | 8/1995 | |
| JP | 7-112491 | 12/1995 | |
| JP | P H07-112491 B | 12/1995 | |
| JP | 09-155260 | 6/1997 | |
| JP | P H09-155260 A | 6/1997 | |
| JP | 2000-176339 | 6/2000 | |
| JP | P 2000-176339 A | 6/2000 | |
| JP | 2002-200447 | 7/2002 | |
| JP | P 2002-200447 A | 7/2002 | |
| JP | 2003-038646 | 2/2003 | |
| JP | P 2003-38646 A | 2/2003 | |
| JP | 2003-245580 | 9/2003 | |
| JP | 2003-266034 | 9/2003 | |
| JP | P 2003-266034 A | 9/2003 | |
| JP | U 3100873 | 1/2004 | |
| JP | U 3100873 U | 1/2004 | |
| JP | 2004-159875 | 6/2004 | |
| JP | P 2004-159875 A | 6/2004 | |
| JP | 2004-236508 | 8/2004 | |
| JP | P 2004-236508 A | 8/2004 | |
| JP | P 2003-245580 A | 9/2008 | |

* cited by examiner (D)

(E) Example of Mode 3

(A)

(B)

MIST GENERATOR AND MIST EMISSION RENDERING APPARATUS

TECHNICAL FIELD

The present invention relates to a mist generator for discharging a mist containing chemicals which are used in lives, such as perfumes, medicines, fungicides, and deodorizers, using ultrasonic waves, and a mist discharge producing apparatus using the mist generator. Note that, in the present invention, the mist generator shall include apparatuses for atomizing or evaporating a liquid, and apparatuses for discharging the mist.

BACKGROUND ART

Prior arts and problems thereof will be described concerning an apparatus for discharging a mist which contains a perfume as an example of the above-mentioned chemicals.

In recent years when people are subjected to various stress, fragrance generators using an ultrasonic mist generator attract attention as products for giving people healing. They will become attractive products if various aromas c~n be presented while switching them.

Generally, while an element with a piezo-electric effect or a magnetostrictive effect is used for an ultrasonic transducer used for the mist generator, there are element structures to be used, one has a cantilevered suspension structure, namely, one tip of the vibrator is fixed, and the other tip thereof is vibrated at high speed while contacting it to a liquid; and the other one has a structure in which the element is vibrated in a thickness direction while surroundings of the element being supported, like a disk type vibrator.

As an example of the former cantilevered suspension structure, a structure in which a liquid is retained in a liquid retaining material such as small a sponge, and the vibration point is contacted to the liquid retaining material to thereby generate the mist is disclosed in a fragrance generator of Japanese Published Examined Application Hei. 7-112491. Various aromas can be generated, if a plurality of liquid retaining materials for retaining various perfume liquids are prepared to make them contact with the vibration point.

In the case of the cantilevered suspension structure, however, since it is difficult to vibrate the vibration point at high frequency, particle diameters of the generated mists are apt to be large and uneven. The mists with large particle diameters disperse around the circumference of the apparatus without evaporating, thus causing a problem leading to contaminations.

Additionally, there are problems that an amount of atomization per unit time is small since the contact portion is small, production thereof is difficult since a contact mechanism portion between the tip of the ultrasonic transducer and the liquid retaining portion requires high accuracy, and the mechanism portion is easily degraded. For this reason, there are few examples commercialized as home use.

Meanwhile, an apparatus for generating the mist by ultrasonically vibrating the liquid at high speed while putting the disk type ultrasonic transducer in a liquid storage is disclosed, for example in an ultrasonic atomizing apparatus of Japanese Unexamined Patent Publication (Kokai) No. 2003-245580, and in a humidifier of Utility Model Registration No. 3100873, or the like. Since it is possible to vibrate the vibrator at a high frequency over 1 MHz, the particle diameters of the mists can be made extremely small. Considering applications to the fragrance generators, it will be an apparatus with excellent smell characteristics because of an easy evaporation of the perfume.

In the disk type ultrasonic transducer driven at the high frequency, however, the ultrasonic waves reflect on the surface of the element once the liquid stops existing in the plane of vibration, causing a problem that the ultrasonic transducer itself generates heat to increase a temperature thereof.

In the case of a piezoelectric device, if the temperature of the element exceeds a predetermined temperature, a piezoelectric polarization characteristic thereof will be degraded, or the element itself will be broken to be destroyed. Although it also depends on materials, the polarization is degraded when the element temperature is about 80 degrees Centigrade or more, and it may be destroyed about 150 degrees Centigrade or more. There are similar problems also in the element utilizing the magnetostrictive effect.

Hence, the ultrasonic transducer driven at a high frequency is commonly used in such a way that the sufficient liquids may always exist on the plane of vibration. In other words, since there is a risk that the ultrasonic transducer may be destroyed, the mist generator for atomizing a small amount of liquid by the ultrasonic waves with a high frequency has not been well studied so far in the field of household articles.

Many ultrasonic mist generators commercialized as home use now usually atomize water or one type of perfume-containing liquid. In addition, most of the systems atomize the liquid for atomization in a condition where it is sufficiently supplied on the ultrasonic transducer.

However, even when one type of aroma is discharged for a long time, people stops feeling the aroma shortly since they have smell adaptive characteristics, so that an expensive perfume becomes useless easily. When a perfume that is strong in physiological influence is used, there may also arise a problem which is not preferable on healthy.

Moreover, since the conventional ultrasonic mist generator is hard to be cleaned because of its structure, remaining perfume tends to contaminate the inside of the apparatus when using a perfume-containing liquid. It has hardly spread as a whole because of such a maintenance problem.

Hereinafter, it will be described that what kind of technical problems there are in the conventional mist generators that use the high frequency ultrasonic transducer using specific examples.

Figure 28:
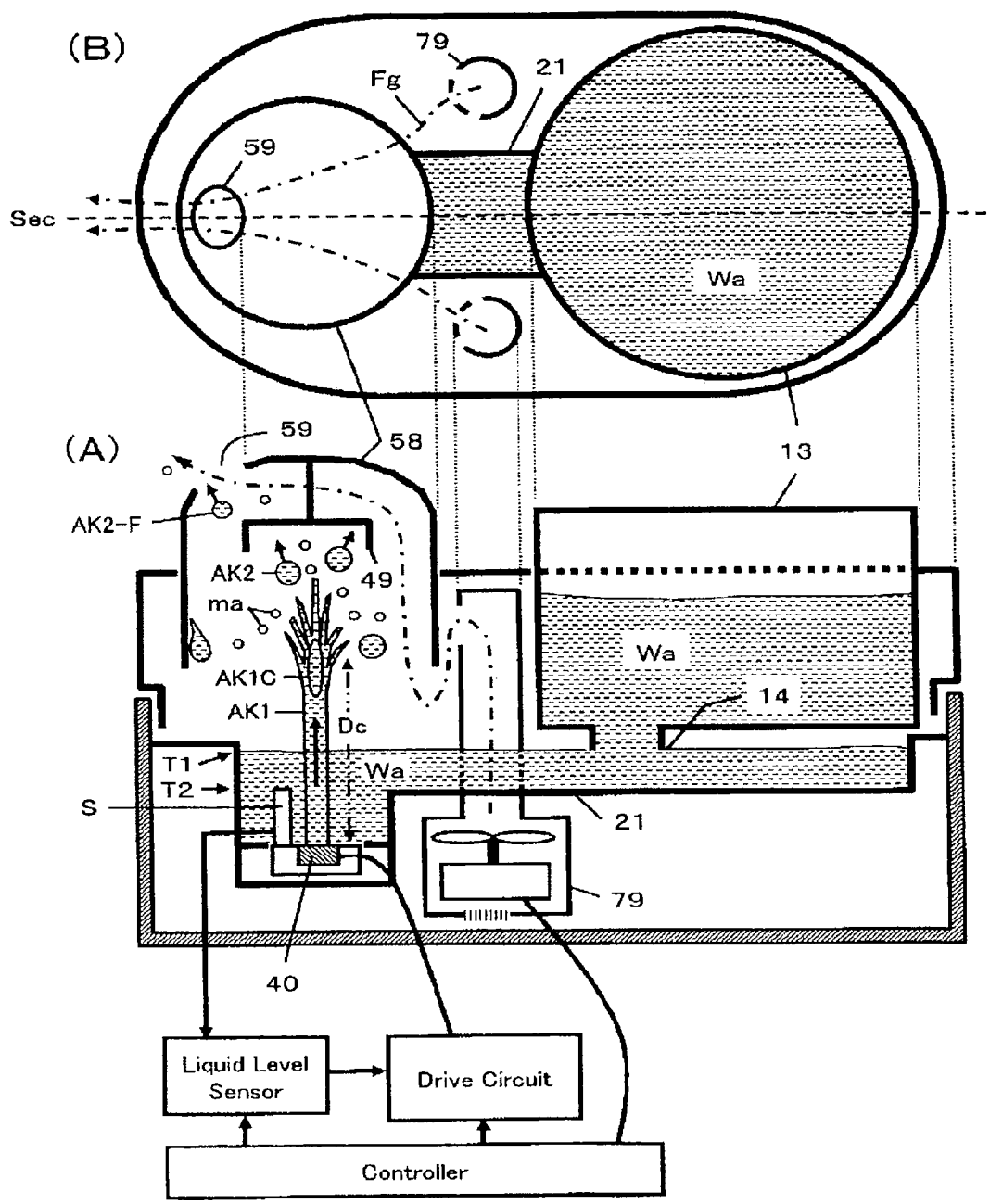

FIG. 28 is an exemplary example of the conventional home mist generator using an ultrasonic transducer. FIG. 28(A) is a sectional view and FIG. 28(B) is a top view. A cross section at the dashed line Sec in FIG. 28(B) corresponds to FIG. 28(A). In the same figure, reference numeral 13 is a liquid container, reference numeral 21 is a liquid storage, reference numeral 40 is an ultrasonic transducer, reference numeral 79 is an air blower mechanism, and symbol S is a liquid level sensor.

An operation thereof will be described briefly. In the same figure, a perfume-containing liquid Wa in the liquid container 13 flows into the liquid storage 21, and is kept at a water level of T1. T1 is decided by a position (height) of a liquid outlet 14 of the liquid container 13. When the liquid Wa in the liquid storage 21 is decreased, the liquid Wa is automatically supplied into the liquid storage 21 since air flows into the liquid container 13 from the liquid outlet 14. Thus, the water level is always kept at T1.

Operation of an ultrasonic transducer 40 will generate a liquid column AK1 from a liquid surface, and droplet dispersed liquids AK2 and atomized fine-particles ma will be generated from an upper part of AK1. Hereinafter, the atomized fine-particles will be expressed as mist. AK2 collides with a liquid dispersion preventing mechanism 49 and drops.

The mist ma is discharged by the air blower mechanism 79 from a mist discharge port 59 of a mist discharge tube 58. An alternate long and short dash line Fg indicates an air current flow by the air blower mechanism.

When the liquid in the liquid container 13 becomes empty, a liquid level of the liquid storage 21 will drop. When the liquid level drops to T2, the liquid level sensor S will operate and driving power to the ultrasonic transducer 40 will be cut off. T2 is a water level with which a plane of vibration of the ultrasonic transducer 40 is fully filled, and is normally set to an upper point by about 1 cm from the plane of vibration. This is for preventing boil-dry of the ultrasonic transducer 40.

Next, the problems of the conventional mist generator shown in FIG. 28 will be described. A first problem is related to means for atomizing the liquid. Since the plane of vibration of the ultrasonic transducer 40 faces upwardly, the liquid column AK1 is generated vertically. A part of ultrasonic energy is consumed for pushing up the liquid.

For this reason, a rate for the ultrasonic energy to be used for atomization is small, thus causing less atomization efficiency. Additionally, since the liquid column AK1 tends to be high and the mist is generated from a wide range of an upper part of AK1, the mist discharge tube 58 must be high and large in capacity, causing the mist generator to tend to be large-scale.

Moreover, when the air flow generating means 79 is used in order to discharge the mist, a part of droplet dispersed liquids AK2-F will be carried together with the mist, causing a problem that the liquids are dispersed around the circumference from an opening 59 to contaminate it.

A second problem is related to means for changing an aroma type. In order to change the aroma type in a configuration shown in FIG. 28, it is necessary to replace the liquid in the liquid storage 21. However, a volume of the liquid storage 21 is large, and it is necessary to create a situation where the perfume-containing liquid Wa above T2 always exists in order to prevent that the ultrasonic transducer 40 falls in a boil-dry state, and thus even when the liquid container 13 is exchanged to a liquid container containing another perfume, the liquids before and after the exchange are mixed with each other in the liquid storage 21, making it difficult to switch the aroma at high speed and clearly.

A third problem is related to cleaning and maintenance. As described above, since the mist discharge tube 58 is large, the droplet dispersed liquids AK2 disperse in a wide range. For this reason, it is troublesome to clean the inside of the apparatus and its maintainability is poor. This is a serious problem as the home mist generator.

Moreover, in order to prevent degradation of the ultrasonic transducer 40 as described above, the liquid in the liquid storage 21 cannot be used up. Namely, even after the apparatus is used, the liquid storage 21 will be in a situation where the liquid always remains. When the perfume-containing liquid Wa is left as it is, it will cause perfume degradation and bacteria breeding. That is unsanitary and bad also for health rather than healing.

A fourth problem is related to the air flow generating means 79. Since the mists are only blown out of the opening 59 in a system using normal air blowing blades, it is visually uniform and insipid. Stage effects are unsatisfactory.

As described above, the ultrasonic mist generator for home use has less atomization efficiency, and does not primarily have a structure aiming at switching the aroma, so that it might not be used as an aroma switching apparatus. Naturally, it neither has a function for mixing aromas. Even when it is used as a single-aroma generator, there are maintenance problems, such as useless consumption of the perfumes, troublesome cleaning, or the like. Moreover, there are problems that the apparatus tends to be large-scale, and there is no function for increasing healing effects by producing the discharge of the mist.

[Patent Document 1] Japanese Published Examined Application Hei. 7-112491

[Patent Document 2] Japanese Unexamined Patent Publication (Kokai) No. 2003-245580

[Patent Document 3] Utility Model Registration No. 3100873

[Patent Document 4] Japanese Unexamined Patent Publication (Kokai) No. 2003-38646

[Patent Document 5] Japanese Unexamined Patent Publication (Kokai) No. 2003-266034

[Patent Document 6] Publication of Unexamined Utility Model Application No. Sho. 58-8034

[Patent Document 7] Publication of Unexamined Utility Model Application No. Hei. 2-104872

[Patent Document 8] Publication of Unexamined Utility Model Application No. Sho. 63-198933

[Patent Document 9] Japanese Unexamined Patent Publication (Kokai) No. Hei. 3-65264

[Patent Document 10] Japanese Unexamined Patent Publication (Kokai) No. Hei. 07-213968

[Patent Document 11] Japanese Unexamined Patent Publication (Kokai) No. 2002-200447

DISCLOSURE OF THE INVENTION

Problem to be Solved by the Invention

The main object that the mist generator of the present invention attempts to solve is to achieve an efficient mist generator suitable for an object that the chemicals used in lives, such as perfumes, medicines, fungicides, and deodorizers, are contained in the mist to be discharged. Specifically, a configuration in which atomization efficiency is high, utilization efficiency of chemicals is high, and the chemicals that is to be contained in the mist to be discharged can be switched in a short time is an important subject.

Moreover, when the mist generator is seen from a user's side, that it can be compactly and economically composed, it can comfortably present the mist to users, and cleaning is easy and maintainability is good is an important subject.

An object that the mist discharge producing apparatus of the present invention attempts to solve is to achieve an apparatus which presents a sensory stimulation according to the type of above-mentioned mist to be generated, and produces an atmosphere with high healing effects.

Means for Solving Problem

Means 1

A mist generator of the present invention is, when described with relation to, for example, FIG. 4, FIG. 5, FIG. 10, FIG. 19, FIG. 20, FIG. 21, and FIG. 27, characterized by comprising:

an ultrasonic transducer (40); an ultrasonic propagation medium (Liq1) or a liquid for atomization (Liq2) provided so as to fill a plane of vibration of the ultrasonic transducer; an ultrasonic convergence and reflection mechanism (24 or 25) provided in the ultrasonic propagation medium or the liquid for atomization; and means for discharging a mist outside, wherein the above-mentioned means for discharging the mist outside uses at least the above-mentioned ultrasonic convergence and reflection mechanism and an ultrasonic reflection tube (27 or 29) as components, and the ultrasonic convergence and reflection mechanism has a function for pushing up the liquid for atomization (Liq2) to locally disperse an end thereof, the ultrasonic reflection tube is composed of an ultrasonic reflecting material with tube length of 3 cm or more, is kept at a predetermined height from a liquid level of the above-mentioned liquid for atomization so that a lower part of the tube may surround the above-mentioned end of the liquid and a local liquid dispersing portion and air may enter from the lower part of the tube, and has a mist/liquid separating function for introducing most of ultrasonic waves scattering around the dispersing portion into the tube to convert them into traveling waves in a tube axial direction, carrying the mist only by the traveling wave in the axial direction until it passes through the tube, and dropping a droplet liquid from the lower part of the tube.

In the above-mentioned means 1, the mist/liquid separating function is possible by any one of following means on condition that the mist is carried only by the ultrasonic waves in the ultrasonic reflection tube.

a; As shown in FIG. 5 (GD1, GD2), supposing that a tube length is L, a tube diameter is D, and an angle between a direction of the ultrasonic wave HD and an axis of the ultrasonic reflection tube is β, the ultrasonic reflection tube is arranged so as to satisfy conditions of $L \geqq 3$ cm and $\tan \beta \geqq D/L$.

b; As shown in FIG. 5 (GD4), and FIG. 10, a curved ultrasonic reflection tube is used.

c; As shown in FIG. 18, the ultrasonic reflection tube with tube length of about 5 cm to 20 cm, which is sufficient for the droplet dispersed liquids AK2 to be atomized in the tube or to drop, is used.

In the above-mentioned means 1, the above-mentioned means for keeping it at the predetermined height is composed of liquid pouring means (01*a*, 01*b*) for keeping the liquid level constant, and means 291 for holding the ultrasonic reflection tube at the predetermined height from the liquid level in FIG. 10 and FIG. 27, for example. Meanwhile, in FIG. 5 (GD5), it is composed of liquid pouring means (10) for keeping the liquid level constant, and means 191 for holding the ultrasonic reflection tube.

A component 30 shown in FIG. 17, or a small liquid container up/down mechanism (component 20 shown in FIG. 21, FLT) can be used for the means for keeping the liquid level constant.

In the above-mentioned means 1, the small liquid container with an ultrasonic transparent film (20) containing the liquid for atomization (Liq2) can keep the liquid level constant regardless of a fluid volume of the liquid Liq2 by being floated on the ultrasonic propagation medium (Liq1), as shown in, for example FIG. 12 and FIG. 21.

In the above-mentioned means 1, it is possible to constitute the ultrasonic transducer (40) so as to move around the axis in the ultrasonic propagation medium (Liq1) to thereby irradiate the ultrasonic waves to a plurality of liquids for atomization (Liq2), as shown in, for example FIG. 10, FIG. 19, and FIG. 27.

In the above-mentioned means 1, a direction of the mist can be changed by moving an integrated mechanism of an ultrasonic concave mirror lens (25) and the ultrasonic reflection tube (27), as shown in, for example FIG. 17.

Means 2

A mist generator of the present invention is, when described with relation to, for example, FIG. 18, FIG. 19, and FIG. 20, characterized by comprising: an ultrasonic transducer (40); an ultrasonic propagation medium (Liq1) provided so as to fill a plane of vibration of the ultrasonic transducer; means for holding a liquid for atomization (Liq2) so that it may contact with the ultrasonic propagation medium; an ultrasonic convergence and reflection mechanism (24 or 25) provided in the ultrasonic propagation medium or the liquid for atomization; and means for discharging a mist outside, wherein the above-mentioned means for holding the liquid for atomization is composed of a small liquid container (20) with an ultrasonic transparent film (23), the above-mentioned means for discharging the mist outside uses at least the above-mentioned ultrasonic convergence and reflection mechanism and an ultrasonic reflection tube (27 or 29) as components, and the ultrasonic reflection tube has a function for carrying the mist in an axial direction of the tube only by ultrasonic traveling waves generated within the tube until it passes through the tube, and the above-mentioned small liquid container (20) with the ultrasonic transparent film and the ultrasonic reflection tube are integrally composed, and the integrated structure is detachably and attachably held so that the ultrasonic transparent film (23) may contact with the above-mentioned ultrasonic propagation medium (Liq1).

In the above-mentioned means 1 or means 2, the ultrasonic transparent film (23) of the small liquid container (20) can be formed into a structure with a hollow, as shown in FIG. 10, FIG. 17, FIG. 18, FIG. 19, FIG. 20, and FIG. 27.

In the above-mentioned means 1 or means 2, the ultrasonic reflection tube (27 or 29) may be constituted so as to separate the mist (ma) and the droplet dispersed liquid (AK2) in the tube to return the droplet dispersed liquid (AK2) to the liquid container (20) as shown in, for example, FIG. 4, FIG. 5 (GD5), FIG. 10, FIG. 18, FIG. 19, and FIG. 21. It can be achieved by setting the length of the tube to 3 cm or more, leaning the axis of the tube to a liquid dispersing direction (refer to the angle β shown in FIG. 5), or using a curved tube (29).

In the above-mentioned means 1 or means 2, the ultrasonic reflection tube (27, 29) is provided so as to surround a neighborhood where the ultrasonic waves are scattered by the liquid dispersion, and a position where air is taken in the tube in the lower part of the tube is preferably lower than the neighborhood where the ultrasonic waves are scattered and upper than the liquid level.

In the above-mentioned means 1 or means 2, it is preferable that the ultrasonic reflection tube has a high ultrasonic reflectance and it is made from a material with sound isolation effects. Materials, such as metal, ceramics, or the like may be used. The diameter and the shape of the reflection tube are designed so that the ultrasonic waves may travel in the tube while repeating reflection. The diameter of the reflection tube is preferably about 5 mm to 2 cm. The length of the reflection tube may be about 1 cm to 100 cm, preferably about 5 cm to 20 cm. Curved tubes (for example, 29 in FIG. 4, 272 in FIG. 5, 29 in FIG. 10, or the like) other than straight line tubes (for example, 27, 271 in FIG. 5, 27 in FIG. 18 or the like) may be used.

In the above-mentioned means 1 or means 2, it is preferable that, among three components of the ultrasonic transducer (40), the ultrasonic convergence and reflection mechanism (25 or 24), and the ultrasonic reflection tube (27), at least two are integrally coupled as shown in, for example, FIG. 5 (GD5), and FIG. 6 (GD6-A).

Particularly, it is preferable that the ultrasonic transducer and the ultrasonic convergence and reflection mechanism are integrally coupled so that the end of the liquid for atomization (Liq2) pushed out by the ultrasonic waves may be located near a focal point (Foc) of the convergence and reflection mechanism, and the ultrasonic convergence and reflection mechanism and the ultrasonic reflection tube are integrally coupled so that the ultrasonic waves, which are circumferentially scattered when the liquid (Liq2) reflected and pushed out by the convergence and reflection mechanism locally disperses, may travel in the axial direction of the reflection tube, and air may enter from the lower part of the tube. Here, the term of "integrally coupling" means that a plurality of parts are integrally molded, or a plurality of parts are arranged in a predetermined physical relationship by a fitting mechanism or the like.

Means 3

Figure 18:
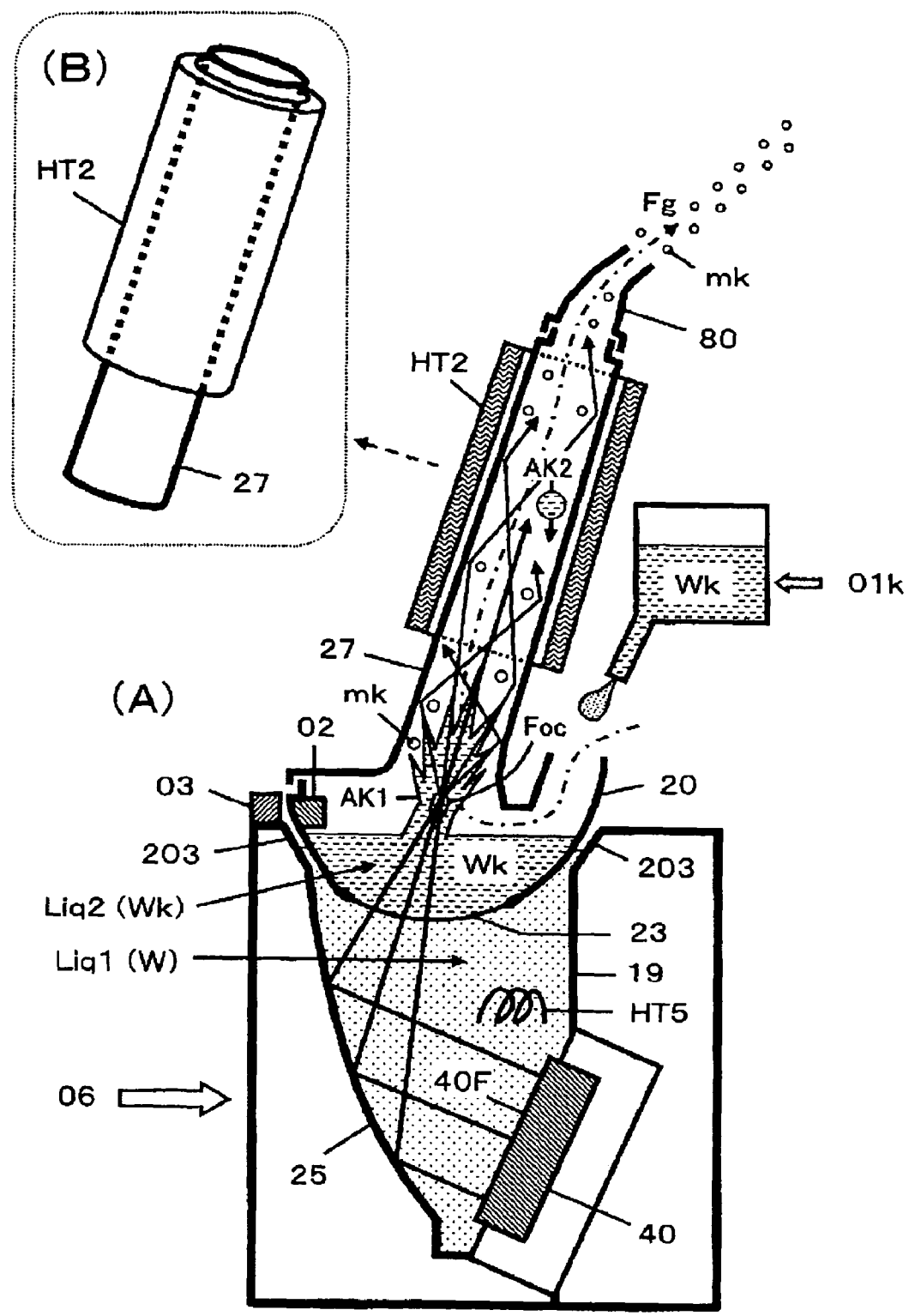
Figure 19:
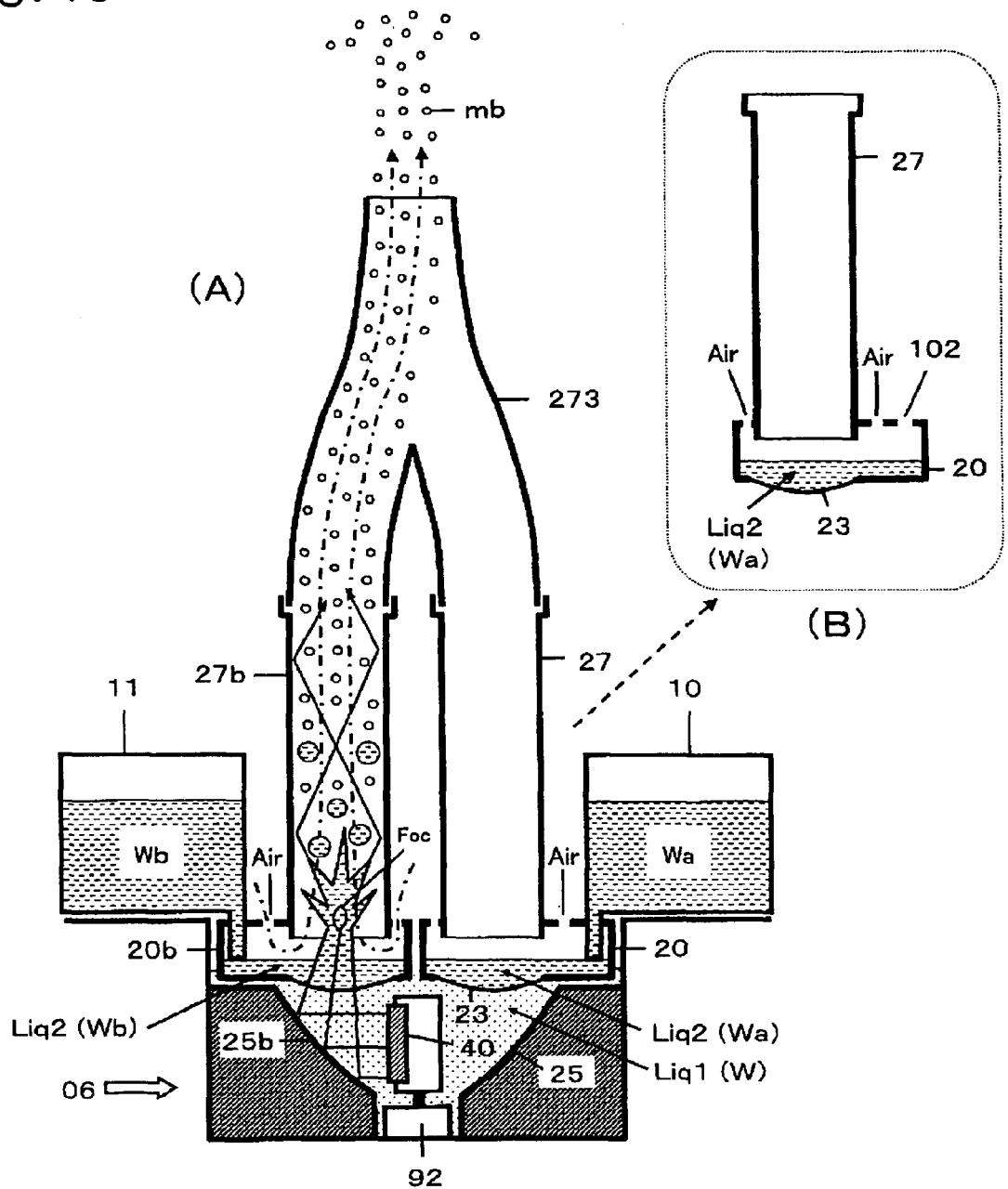
Figure 20:
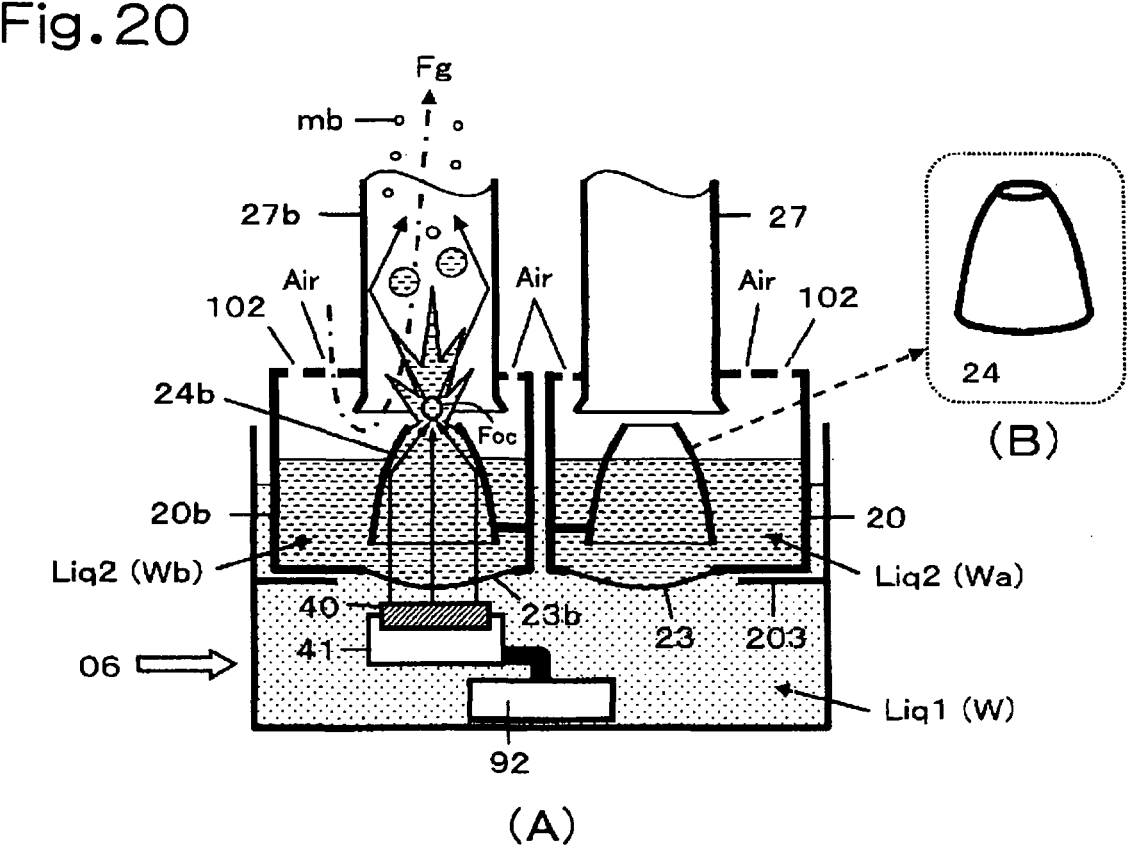

A mist generator of the present invention is, when described with relation to, for example, FIG. 10, FIG. 19, FIG. 20 and FIG. 21, characterized by comprising: an ultrasonic transducer (40); an ultrasonic propagation medium (Liq1) provided so as to fill a plane of vibration of the ultrasonic transducer; means for holding a liquid for atomization (Liq2) so that it may contact with the ultrasonic propagation medium; an ultrasonic convergence and reflection mechanism (25 in FIG. 10, FIG. 19, and FIG. 21, or 24 in FIG. 20) provided in the ultrasonic propagation medium or the liquid for atomization; and means for discharging a mist outside, wherein the above-mentioned means for holding the liquid for atomization is composed of a small liquid container (20) with an ultrasonic transparent film (23), and the above-mentioned ultrasonic transducer (40) or the above-mentioned plurality of small liquid containers (20) are supported by a movable mechanism (90, 91 in FIG. 10, 92 in FIG. 19, 92 in FIG. 20, and 171, 18 in FIG. 21), and ultrasonic waves emitted from the ultrasonic transducer are irradiated so as to be converged near an end of the liquid arbitrarily selected among a plurality of liquids for atomization (Liq2) by the movable mechanism and the above-mentioned ultrasonic convergence and reflection mechanism (25 in FIG. 10, FIG. 19, and FIG. 21, and 24 in FIG. 20).

In the above-mentioned means 3, it is preferable that the plurality of liquids for atomization are controlled to be at an approximately constant liquid level.

Figure 10:
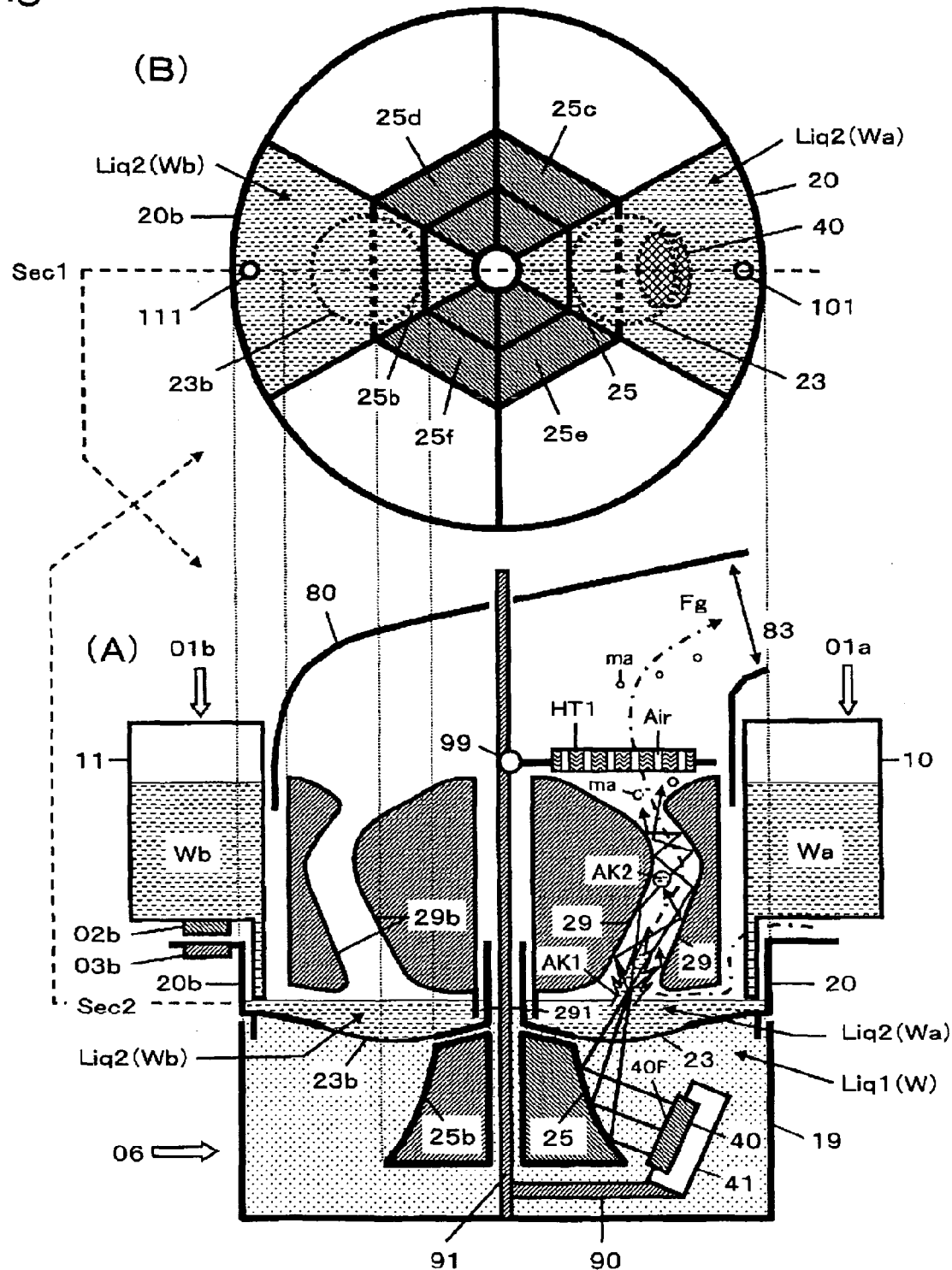

In the above-mentioned means 3, the plurality of liquids for atomization (Liq2 (Wa), Liq2 (Wb), or the like) are circularly arranged, and a plurality of ultrasonic concave mirror lenses (25, 25b, or the like) are provided so as to correspond thereto, as shown in FIG. 10, FIG. 19, and FIG. 20, thus the ultrasonic waves can be irradiated to a portion near the liquid level of the liquid for atomization selected arbitrarily by the ultrasonic transducer (40) which rotates about the center of the circle.

In the above-mentioned means 3, the means for irradiating the ultrasonic waves so as to be converged near the end of the liquid arbitrarily selected among the above-mentioned plurality of liquids for atomization (Liq2) may be constituted using means (205) for inserting the means (20, 20*b*, or the like) for holding the plurality of liquids for atomization into an ultrasonic propagation path as shown in FIG. 21.

Specifically, the plurality of liquids for atomization (Liq2 (Wa), Liq2 (Wb), or the like) are circularly arranged between the concave mirror lens (25) and the ultrasonic reflection tube (27), and the mechanism (171) circularly arranged is rotated, thereby making it possible to irradiate the ultrasonic waves to the liquid arbitrary selected.

Means 4

A mist generator of the present invention is, when described with relation to, for example, FIG. 1, FIG. 4, FIG. 13, FIG. 19, and FIG. 21, characterized by comprising: an ultrasonic transducer (40); an ultrasonic propagation medium (Liq1) or a liquid for atomization (Liq2) provided so as to fill a plane of vibration of the ultrasonic transducer; an ultrasonic convergence and reflection mechanism (25) provided in the ultrasonic propagation medium or the liquid for atomization; and means for discharging a mist outside, wherein the above-mentioned means for discharging the mist outside includes means (for example, 27 or 29) for carrying the mist near a tip of a mist discharge passage, means (for example, 47, 48 in FIG. 1 and FIG. 13) for detecting a concentration of the mist provided in the mist discharging passage, and instant air flow generating means (for example, 74 in FIG. 1 and FIG. 13), wherein the instant air flow generating means (74) is driven upon detecting that the mist concentration becomes higher than a predetermined concentration.

In the means 4, the above-mentioned means for discharging the mist outside uses at least the above-mentioned ultrasonic convergence and reflection mechanism and an ultrasonic reflection tube (27 or 29) as components, the ultrasonic reflection tube has a mist/liquid separating function for carrying the mist near the tip of the mist discharge passage by ultrasonic traveling waves generated within the tube, and dropping a droplet liquid from a lower part of the tube, the mist near the tip of the above-mentioned mist discharge passage can be discharged as an annular mass (Lm) by the instant air flow generating means for instantaneously increasing an air pressure of the tube.

An air pressure of the mist discharge tube (81 in FIG. 1 and FIG. 4, and 80 in FIG. 13) provided so as to surround the above-mentioned ultrasonic reflection tube might be instantaneously increased. The tip of the tube for discharging the mist is preferably narrowed so that a cross section thereof may be about ⅔ to 1/10 compare with a stem of the tube.

In the means 4, it is possible to provide fluctuation to a discharge time interval of the mist, or to provide fluctuation to a discharge speed thereof.

Means 5

A mist generator of the present invention is, when described with relation to, for example, FIG. 10, FIG. 18, FIG. 21, and FIG. 27, characterized by comprising: an ultrasonic transducer (40); an ultrasonic propagation medium (Liq1) or a liquid for atomization (Liq2) provided so as to fill a plane of vibration of the ultrasonic transducer; an ultrasonic convergence and reflection mechanism (24 or 25) provided in the ultrasonic propagation medium or the liquid for atomization; and means for discharging a mist outside, wherein the above-mentioned means for discharging the mist outside uses the above-mentioned ultrasonic convergence and reflection mechanism, a ultrasonic reflection tube (27 or 29), and means for heating the inside of the tube, or a mist discharge passage coupled with the tube (for example, HT2 in FIG. 18, HT3 in FIG. 21, or HT1 in FIG. 27) as components, and has a function for raising the mists while maintaining visibility by using ultrasonic traveling waves together with ascending air currents in the tube.

In the above-mentioned means 5, the ultrasonic reflection tube may be provided with a mist/liquid separating function for carrying the mist in an axial direction of the tube by ultrasonic traveling waves generated within the tube until it passes through the tube, and dropping a droplet liquid from a lower part of the tube.

In the above-mentioned means 5, the inside of the above-mentioned ultrasonic reflection tube (27, 29) or the upper part of the tube can be heated uniformly, and thus the air current can be raised orderly. A temperature of the mist or vapor near the heating means (HT1) can be heated in a range higher than a room temperature by 5 degrees Centigrade or more, and 50 degrees Centigrade or less. It is further preferable to be heated in a rage of higher than the room temperature by 10 degrees Centigrade or more, and 45 degrees Centigrade or less. As a result of this, as for a rising appearance of the mist, quick repeated movements (fluctuation) tend to appear in orderly and slow movements as a whole. Namely, a frequency component contained in the movement of the mist is proportional to an inverse number of the frequency. Moreover, the above-mentioned term "while maintaining visibility" means to create a situation where the motion of the mist is visible, and thus it is preferable to create the situation where the fluctuation of the mist is visible.

In the above-mentioned means 5, the heating means (HT1) provided in the mist discharge passage is composed of a plate-like heating element provided with many holes through which air passes, and the heating element may be provided so as to cross a mist discharge passage (Fg) as shown in, for example, FIG. 1, FIG. 10, FIG. 25, and FIG. 27.

Figure 27:
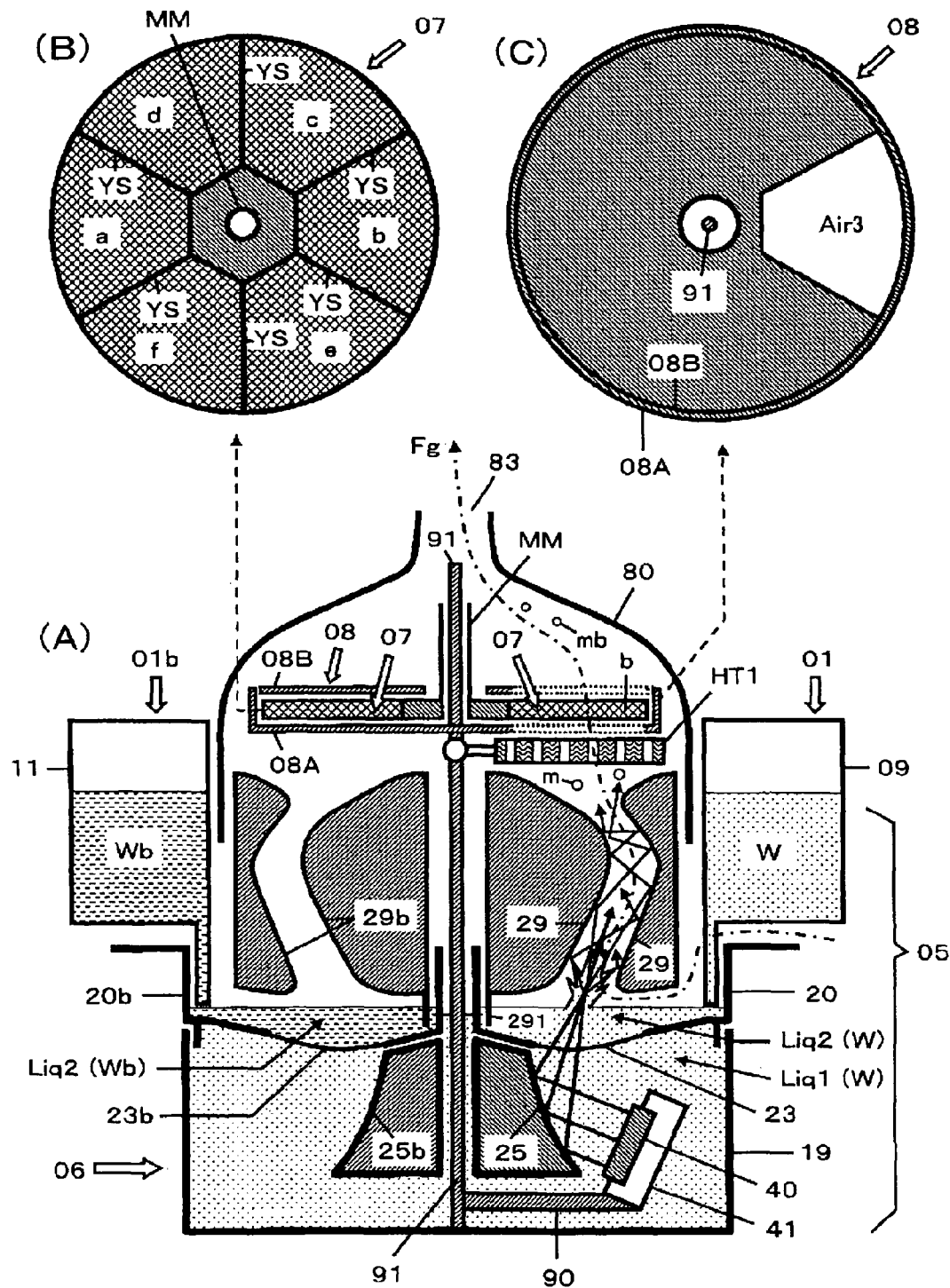

As shown in FIG. 27, the chemical-containing material (07) is warmed by the heating means (HT1), and evaporated chemicals are discharged with the above-mentioned mist, Means 6

Figure 22:
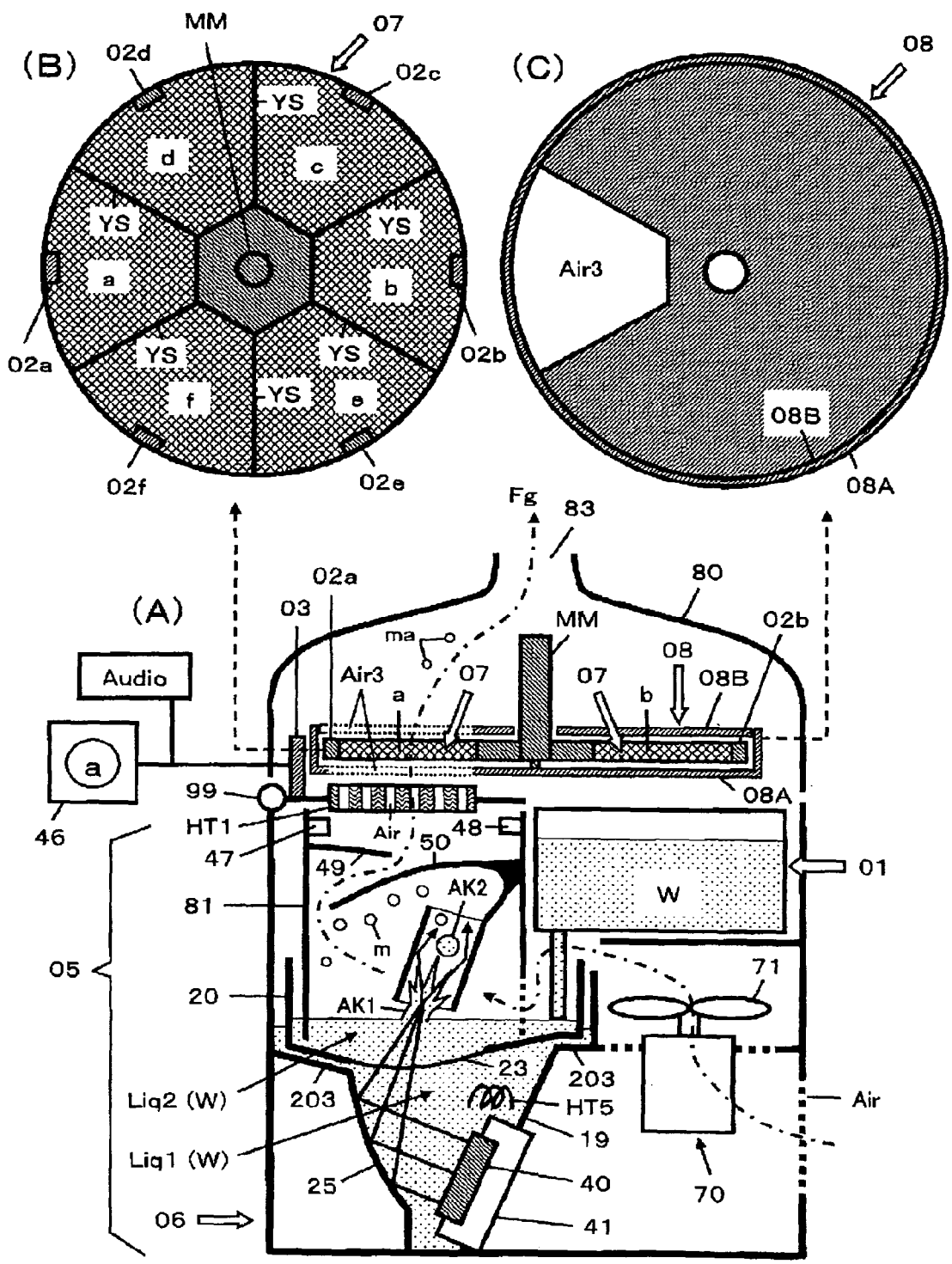
Figure 25:
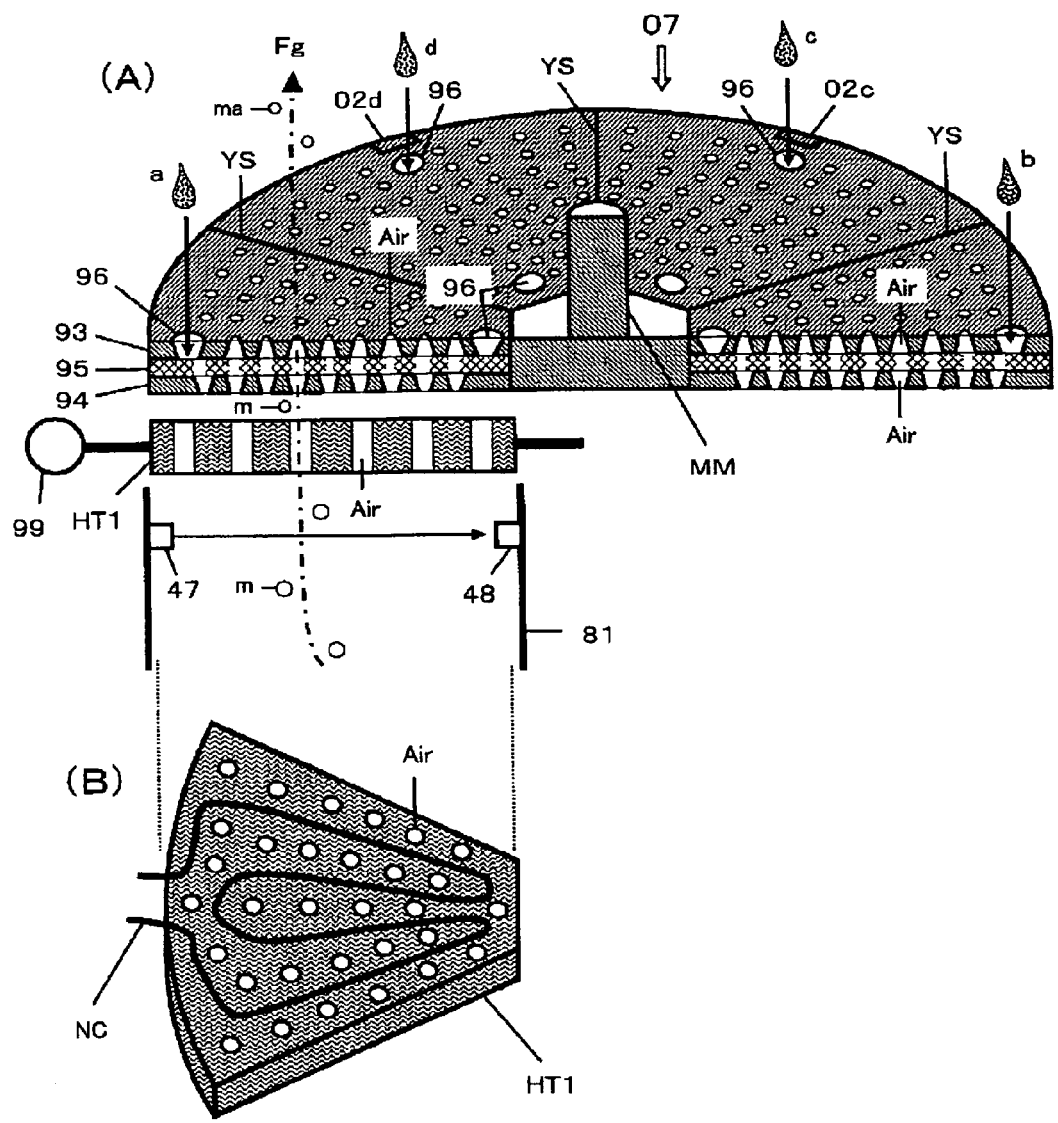

A mist generator of the present invention is, when described with relation to, for example, FIG. 22, FIG. 25, and FIG. 27, characterized by comprising: an ultrasonic transducer (40); an ultrasonic propagation medium (Liq1) or a liquid for atomization (Liq2) provided so as to fill a plane of vibration of the ultrasonic transducer; an ultrasonic convergence and reflection mechanism (24 or 25) provided in the ultrasonic propagation medium or the liquid for atomization; and means for discharging a mist outside, wherein the above-mentioned means for discharging the mist outside uses at least the above-mentioned ultrasonic convergence and reflection mechanism and an ultrasonic reflection tube (27 or 29) as components, and the ultrasonic reflection tube has a mist/liquid separating function for carrying the mist in an axial direction of the tube only by ultrasonic traveling waves generated within the tube until it passes through the tube, and dropping a droplet liquid from a lower part of the tube, and a chemical-containing material (07) of a mesh structure (refer to FIG. 25) or a porous structure (refer to FIG. 26) which can pass the mist is provided in a mist discharging passage, the chemical-containing material is heated by heating means (HT1, HT2, or HT3), and evaporated chemicals are discharged with the above-mentioned mist.

In the above-mentioned means 6, the above-mentioned ultrasonic reflection tube (27 or 29) forms a part of the mist discharge passage, and can carry the mist near the tip of the mist discharge passage only by the ultrasonic traveling waves generated inside the tube, as shown in FIG. 27.

In the above-mentioned means 6, the mist carried by the ultrasonic traveling waves can pass through the air holes of the above-mentioned chemical-containing material (07) as shown in FIG. 27. Additionally, in order to promote the passage of the mist, air flow generating means (70) may be used together as shown in FIG. 22.

In the above-mentioned means 6, a plurality of chemical-containing materials (07) which move around the axis may be provided in the above-mentioned mist discharge passage as shown in FIG. 22, FIG. 25, and FIG. 27.

In the above-mentioned means 6, as shown in FIG. 27, a plurality of chemical-containing materials (07) and a plurality of liquids for atomization (Liq2) are arranged in a longitudinal direction, and an arbitrary Liq2 is atomized, thus making it possible to pass the mist through the arbitrary chemical-containing material 07. Moreover, a combination between Liq2 and the chemical-containing material 07 may be changed arbitrarily.

In the above-mentioned means 6, it is preferable that the chemical-containing material (07) is plate-shaped as shown in FIG. 25(A), and it is provided with many air holes (Air) in a thickness direction of the plate, and has a property that the chemicals can be discharged as vapor by heating. The chemical-containing material 07 can be composed of a reticulated material (95) or a porous material which occludes the chemicals and enables the passage of air, and a cover plate (93, 94) in which a large number pinholes provided so as to wrap the material are formed.

Means 7

A mist discharge producing apparatus of the present invention is, when described with relation to, for example, FIG. 1, FIG. 8, FIG. 10, FIG. 13, FIG. 18, FIG. 22, and FIG. 25, characterized in that, a mist generator including an ultrasonic transducer (40), an ultrasonic propagation medium (Liq1) or a liquid for atomization (Liq2) provided so as to fill a plane of vibration of the ultrasonic transducer, an ultrasonic convergence and reflection mechanism (25) provided in the ultrasonic propagation medium or the liquid for atomization, and means for discharging a mist outside (27, 29, 70, 74, 80, 81, HT1, HT2, or the like) is used, and means (01, 20, 07, or the like) for containing chemicals in the mist is provided, the means is equipped with memory means (02), and the memory means stores information for producing the mist to be discharged.

In the above-mentioned means 7, the above-mentioned memory means (02) may be constituted by integrated memory circuits. The means for containing the chemicals in the mist may be means (20) for holding the liquid for atomization (Liq2) or means (01) for supplying Liq2 to the holding means. The means (20) for holding the liquid for atomization (Liq2) may be a small liquid container provided with an ultrasonic transparent film in a part of a wall thereof.

In the above-mentioned means 7, the means for containing the chemicals in the mist may the chemical-containing material (07) provided in the mist discharge passage.

In the above-mentioned means 7, the information for producing the above-mentioned mist to be discharged includes drive controlling information on liquid atomization means (05), drive controlling information on heating means (HT1), drive controlling information on air flow generating means (71, 74), or visual information or audio information corresponding to a smell impression of the mist to be discharged. A relation between the perfume, and the visual information or the audio information may preferably be stored in the memory means in advance.

Figure 13:
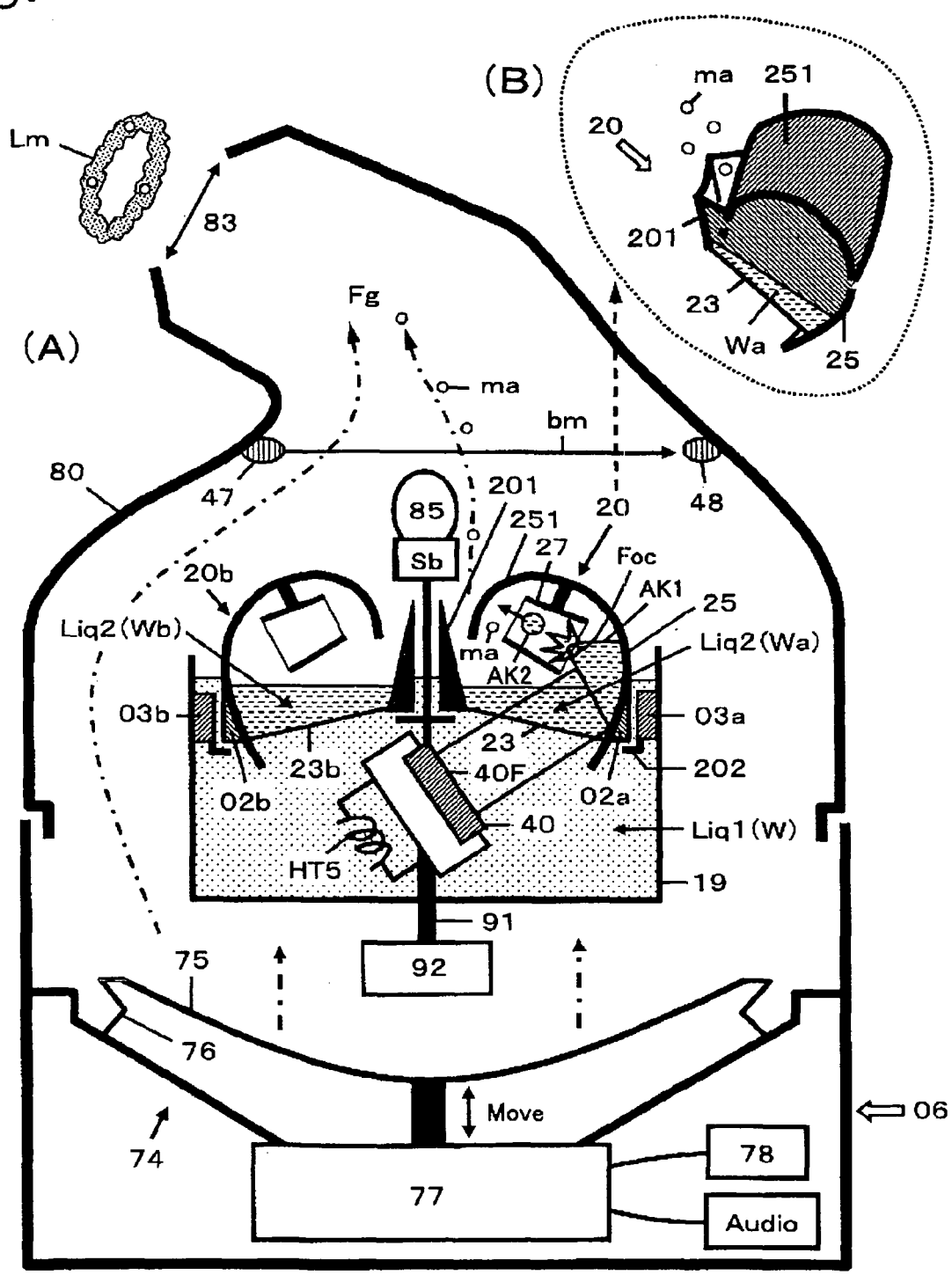

In the above-mentioned means 7, means (85) for irradiating a light which changes colors or intensity may be provided as shown in FIG. 1 and FIG. 13. Particularly, when the mist (ma) is discharged as a mass (Lm), it is possible to provide illumination according to the discharge.

As for the color of the light changed according to the type of perfume-containing mist, it is preferable that the color has a positive correlation between a physiological action or a psychological action of the perfume, and a psychological action of the color of the light.

In the above-mentioned means 7, audio generating means (Audio) in which a tone or sound intensity changes may be provided as shown in FIG. 1 and FIG. 13. Particularly, when the mist (ma) is discharged as the mass (Lm), it is possible to present sound according to the discharge.

In the above-mentioned means 7, as shown in FIG. 1 and FIG. 13, a sensor (Sb) for detecting sound or vibration at the time of generating the mist, and means (Audio) for processing signals of the sensor to play the sound may be provided.

In the above-mentioned means 7, the information for producing the above-mentioned mist to be discharged may be stored in the above-mentioned memory means using communication means, such as the Internet.

In the above-mentioned means 1 through means 7, the ultrasonic propagation medium (Liq1) and the liquid for atomization (Liq2) may be the same type of liquid or a different type of liquid.

In the above-mentioned means 1 through means 7, water (W), alcohol, oil, liquid resin, or the like may be applied to the above-mentioned ultrasonic propagation medium (Liq1). Moreover, water (W), perfume-containing water (Wa or the like), liquid medicines (Wk), liquors, alcohols, liquids with a bactericidal action, liquids with odor eliminating, liquid insecticides, and other chemical-containing liquids may be applied to the above-mentioned liquid for atomization (Liq2).

In the above-mentioned means 1 through means 7, an air flow generator using impellers (for example, 70 in FIG. 22), an instant air flow generator using air guns (for example, 74 in FIG. 1), heat ascending air current generator (for example, HT1 in FIG. 10), and the like may be combined to be used for the means for discharging the mist outside.

In the above-mentioned means 1 through means 7, since heat and impacts are easily generated in the neighborhood where the ultrasonic waves of the ultrasonic convergence and reflection mechanism (24 or 25) gather together, it is preferable to use hard materials for structures of the neighborhood. Metals and glasses may be used.

In the present invention, in order to carry the mist, the heating means (HT1, HT2, HT3) can be used together as shown in, for example, FIG. 10, FIG. 18, FIG. 21, and FIG. 27, the impeller type air flow generating means (70) can be used together as shown in, for example, FIG. 11, FIG. 14, FIG. 15, and FIG. 22, or the instant air flow generating means (air gun; 74) can be used together as shown in, for example FIG. 1 and FIG. 13.

Even in a case where such mist carrying means is used together, when the ultrasonic reflection tube to be used has functional features described in the above-mentioned means 1, means 2, means 4, means 5, and means 6, they are intended to be involved within the scope of the implementation of the means (corresponding to scope of claims).

EFFECT OF THE INVENTION

Effects According to Means 1

As shown in, for example, FIG. 4, FIG. 5, FIG. 10, FIG. 17, FIG. 19, FIG. 20, FIG. 21, and FIG. 27, the ultrasonic waves emitted from the ultrasonic transducer (40) are converged by the ultrasonic convergence and reflection mechanism (25), and are strongly irradiated near the end (Foc) of the liquid for atomization (Liq2). In this case, the liquid is locally dispersed, and the ultrasonic waves are generally hemispherically scattered in a traveling direction at a position where the liquid is dispersed. When the scattered ultrasonic waves are converged into the ultrasonic reflection tube (27 or 29) again to be traveled in the axial direction of the tube, a part of droplet dispersed liquids with large particle diameter generated as by-products when the above-mentioned liquid is atomized, is also atomized, thus increasing atomization efficiency. As compared with the case where the above-mentioned ultrasonic convergence and reflection mechanism (25) and the above-mentioned ultrasonic reflection tube (27 or 29) are not used, the amounts of mist over two to three times are generated.

Moreover, since the liquid for atomization (Liq2) locally disperses and it is atomized as described above, it is suitable for the object of atomizing a small amount of liquid. Hence, using the liquid as the chemical-containing liquid (Wa) makes it possible to achieve the mist generator whose utilization efficiency of the chemical is very high. Additionally, it is easy to atomize various chemical-containing liquids while exchanging them.

By using the above-mentioned ultrasonic convergence and reflection mechanism (25) and the ultrasonic reflection tube (27 or 29) in combination, quite a lot of fine-particles generated within the reflection tube are flown in the axial direction of the tube by a pressure of the ultrasonic waves which travel in the axial direction of the tube. The air flow is generated in the tube, thus allowing the mist generated by the ultrasonic energy to be discharged to the outside.

In the experiment shown in FIG. 5, the longer the ultrasonic reflection tube (27) is, the higher the mist goes up, thus allowing the mist to be discharged to the height exceeding 100 cm from the liquid level. Meanwhile, using an inclined tube, a curved tube, or a long tube makes the ultrasonic reflection tube more effective in dropping the droplet liquid from the lower part of the tube. Namely, the ultrasonic reflection tube of the present invention has the mist/liquid separating function for carrying the mist toward the tip thereof only by the traveling waves, and dropping the droplet liquid. Hence, in embodiments of the present invention shown in FIG. 4, FIG. 5, FIG. 10, FIG. 17, FIG. 18, FIG. 19, FIG. 20, FIG. 21, and FIG. 27, the air flow generating means composed of a fan (wing) and a motor which have been conventionally indispensable can be eliminated. It has profound effects on downsizing and economization.

Moreover, since a portion where the liquid is atomized is separated from the surroundings by providing the above-mentioned ultrasonic reflection tube (27 or 29); there is an effect of reducing sound generated during atomization. A calm mist generator can be achieved.

When the small liquid container (20) containing the liquid for atomization (Liq2) is used while floating it on the ultrasonic propagation medium (Liq1) as shown in FIG. 12 and FIG. 21, the ultrasonic propagation path (Dp) from the plane of vibration (40F) of the ultrasonic transducer to the liquid level of the liquid for atomization (Liq2) can be maintained at almost constant length regardless of the amount of Liq2. Thereby, the atomization is stabilized and a large amount of mist with fine-grain is generated. A mist generator with excellent atomization efficiency can be achieved.

Effects According to Means 2

Since the small liquid container with the ultrasonic transparent film (20) and the ultrasonic reflection tube (27 or 29) are integrally, and attachably and detachably constituted as shown in, for example, FIG. 4, FIG. 18, FIG. 19, and FIG. 20, the integrated structure can be easily exchanged. The mist can be discharged only by placing the integrated structure on the ultrasonic propagation medium (Liq1). The chemicals (perfumes and medicines) to be contained in the mist can be switched at high speed. Additionally, it can be cleaned easily, thus providing excellent maintainability.

Moreover, since the ultrasonic reflection tube (27 or 29) has a function to collect the dispersed liquid of the large mass into the small liquid container (20), it is not necessary to provide a dispersed liquid collecting mechanism independently. Since the droplet dispersed liquid (AK2) is collected in the small liquid container (20) along an inner wall of the reflection tube, it is possible to efficiently atomize a small amount of chemical-containing liquid.

Since the liquid dispersing portion is within the reflection tube with sound insulation, and the liquid container and the reflection tube are integrally constituted and separated from the surroundings as shown in FIG. 18, FIG. 19, and FIG. 20, there is an effect of reducing liquid dispersing sound during atomization. A calm mist generator can be achieved.

<Supplementary Explanation of Effects According to Means 1 and Means 2>

Since the concave mirror lens (25) has the clear focal point (Foc), the ultrasonic energy is focused on the focal point and the liquid is locally atomized within narrow limits. Here, while the ultrasonic waves which have not contributed to the atomization exit from the liquid to be discharged into the air, they are strongly discharged in the same direction as a liquid dispersing direction generally hemispherically.

When it is described using FIG. 5 as an example, the ultrasonic waves generated by the ultrasonic transducer (40) are converged by the concave mirror lens (25), and the liquid locally disperses near the focal point (Foc). On that occasion, the ultrasonic waves exited from the liquid are discharged upward with strong directivity, as shown in the same figure. Here, when the ultrasonic waves with the directivity are introduced into the ultrasonic reflection tube (27) to be repeatedly reflected on the wall of the tube, strong traveling waves will be generated in the tube.

When the function of the ultrasonic reflection tube is described in more detail, the mist (ma) of small particles are pushed up in the dispersed liquid in the axial direction of the tube by a pressure of the ultrasonic traveling waves. The air flow is generated in the tube, and the mist is discharged from the end of the tube. Meanwhile, although the small droplet dispersed liquid (AK2) is similarly pushed up by the traveling waves; atomization is promoted since the ultrasonic waves are continuously irradiated to the liquid during that time, thus generating the mist of small particles. Accordingly, atomization efficiency is increased. Additionally, there is an effect that the sizes of the mist particles are uniformed, so that a large amount of mist with small and uniform particle diameter and high quality is generated. As described above, the ultrasonic reflection tube has effects of increasing the amount of atomization and making the particles small and uniform.

Since the discharged fine-particles drift in the air for a while, smell presentation characteristics are good when the perfume-containing liquid is atomized. It is comfortable also when taking in a medicine from a breather. It is hardly occurs that liquid particles fall around the apparatus to thereby contaminate the circumference thereof, thus providing excellent maintainability.

When the atomization system according to the combination of the ultrasonic concave mirror lens (25) and the ultrasonic reflection tube (27) of the present invention is compared with the conventional atomization system shown in FIG. 28, the amount of mist of two to three times or more are generated when the ultrasonic transducer with the same output is used.

Note herein that, in the conventional atomization system in which a long liquid column is generated as shown in NG3 of FIG. 6, the ultrasonic energy is consumed for pushing up the liquid, and the ultrasonic waves exiting from the liquid column are diffused in various directions, so that the ultrasonic waves with strong directivity are not generated in the tube like the present invention. Unless a carrying air flow is sent from the outside, it is difficult to discharge the mist.

If principal parts of the ultrasonic transducer, the ultrasonic convergence and reflection mechanism, and the ultrasonic reflection tube are constituted as shown in FIG. 5 (GD5), and FIG. 6 (GD6-A), adjustment for effectively utilizing the ultrasonic energy is easy, resulting in easy manufacturing. Meanwhile, it is also possible to unitize them to sell as a liquid atomizer part. Since the number of parts can also be reduced, the apparatus with high atomization efficiency can be achieved at low cost.

According to the constitution shown in FIG. 17, the discharge direction of the mist can be easily changed by changing the angle of the ultrasonic concave mirror lens (25) using an angle adjustment mechanism (26).

A hollow portion (concave surface) is formed at the bottom of the small liquid container 20 to be a liquid storage portion. The hollow portion is composed of the ultrasonic transparent film 23. Hence, as the liquid Liq2 in the small liquid container 20 decreases, the liquid gathers on the ultrasonic transparent film 23. The chemicals can be used efficiently without waste. Additionally, it is effective also for down-sizing of the mist generator.

Note herein that, since the ultrasonic transducer (40) is filled with the ultrasonic propagation medium (Liq1) even in a state where the liquid (Liq2) in the small liquid container has thoroughly been consumed, and it has a structure in which the ultrasonic waves having exited from the ultrasonic transducer hardly rebound to the ultrasonic transducer, the temperature of the ultrasonic transducer does not become high, resulting in high quality.

If a small amount of chemical-containing liquid (Wa) is poured into the small liquid container (20) to be atomized, and after the liquid is consumed, another type of chemical-containing liquid (Wb or the like) is poured therein to control it so as to be atomized, the chemicals to be contained in the mist can be switched and discharged in a short time. Switching of the chemicals (aroma) is clear. Additionally, olfactory fatigue due to inhaling the perfumes too much can be prevented. When a medicine-containing liquid is atomized, the amount of atomization thereof can be accurately controlled.

When the ultrasonic convergence and reflection mechanism (25), the small liquid container (23) with the ultrasonic transparent film (20), and the ultrasonic reflection tube (27 or 29) are used in combination as shown in FIG. 10, FIG. 19, FIG. 20, FIG. 21, and FIG. 27, the liquid in the small liquid container can be discharged very efficiently as described above, and in addition to that, by providing a mechanism for exchanging the small liquid container, the chemical-containing mist can be switched at very high speed to be discharged.

As described above, the constitutions of the means 1 and the means 2 according to the present invention are suitable for an object of efficiently providing or comfortably presenting the mist to users.

<Comparison with Conventional Technology According to Means 1 and Means 2>

Next, features will be supplementarily described about the effects according to the above-mentioned means 1 and the means 2 while comparing them with those of the conventional example. An ultrasonic reflecting horn is used in, for example, a medical atomizer of Japanese Unexamined Patent Publication (Kokai) No. 2003-38646, an atomizing type ultrasonic cleaner of Japanese Unexamined Patent Publication (Kokai) No. 2003-266034, and an ultrasonic humidifier of Publication of Unexamined Utility Model Application No.

Sho. 58-8034. In the liquid, these parts act so that the ultrasonic waves may be converged to thereby disperse the liquid.

Figure 6:
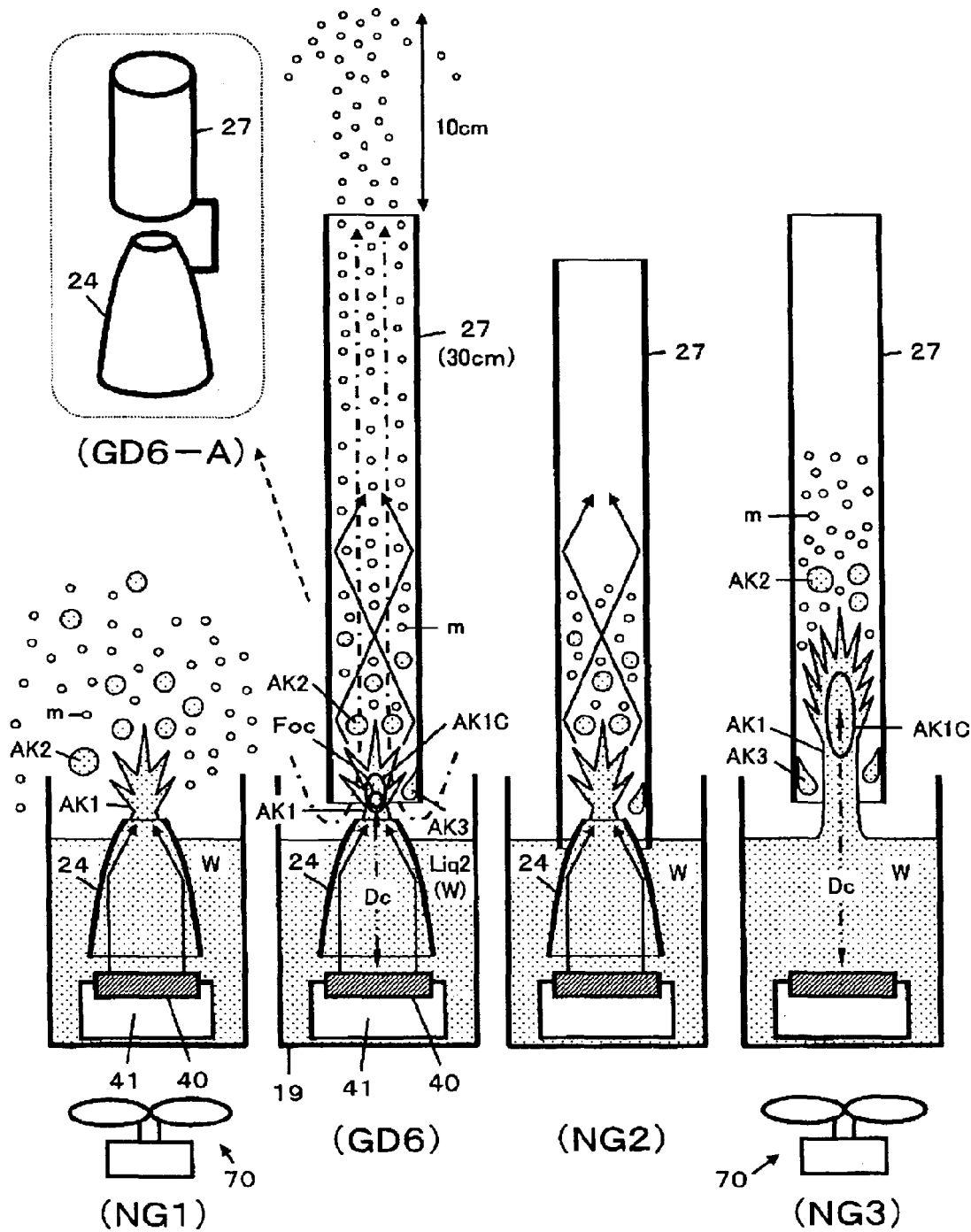

Although its function is partially similar to that of the ultrasonic convergence and reflection mechanism (for example, 25 of FIG. 1, 24 of FIG. 6) of the present invention, the present invention differs from the above-mentioned conventional examples in that the ultrasonic reflection tube (27) is provided so as to surround the liquid which is pushed out and dispersed in the air by the converged ultrasonic waves, namely so as to surround the portion of the liquid to be locally dispersed, the traveling waves are generated in the tube, and air is introduced from the lower part of the tube. Conventionally, there has been no invention in which the ultrasonic waves generated resulting from the local dispersion of the liquid are turned into the traveling waves to be utilized for the discharge of the mist and the promotion of atomization.

In the conventional atomizing apparatus for cleaning or for humidification, liquids with large particle diameters and small particle diameters are readily mixed in the liquids dispersed by the ultrasonic waves, whereas in the present invention, diameters of the fine-particles to be discharged are uniform and small, thus generating a large number (amount) of fine-particles. A large amount of negative ions is also generated. Moreover, the air flow generating means, such as a fan or the like, can be eliminated. There are characteristic effects such that the apparatus can be achieved compactly and economically.

Moreover, as a purpose of applications to humidifying apparatus or the like, a tube mechanism for guiding outside the mists generated by the ultrasonic waves is conventionally disclosed in for example, an ultrasonic mist generator of Publication of Unexamined Utility Model Application No. Hei. 2-104872, and the ultrasonic humidifier of Publication of Unexamined Utility Model Application No. Sho. 63-198933. Although the tube operates as a guide for discharging the mists, it differs from the ultrasonic reflection tube of the means 1 and the means 2 according to the present invention in the structure and the function. The difference of the function will be hereinafter described in detail using experimental results of FIG. 6 and FIG. 7.

An apparatus for atomizing the liquid through the ultrasonic transparent film is disclosed in an atomizing apparatus of Japanese Unexamined Patent Publication (Kokai) No. Hei. 3-65264. However, since the ultrasonic convergence and reflection mechanism is not used in the apparatus; ultrasonic waves are irradiated to the liquid for atomization, without being converged. Since a large liquid column is generated in a liquid bath, it is necessary to store a considerable amount of liquid in the liquid bath. Hence, it is difficult to switch chemicals to be contained in the mist in short time. Additionally, the amount of atomization is little as compared with that of the present invention, resulting in poor utilization efficiency of the liquid for atomization. Further, since the mist is generated from the above-mentioned large liquid column, a large atomization chamber is required. The apparatus becomes large-sized. It is not easy to clean the atomization liquid bath to then switch to another liquid, either.

In a portable ultrasonic humidifier cum small cleaner of Japanese Unexamined Patent Publication (Kokai) No. Hei. 07-213968, there is disclosed a technology of floating a small container, in which an ultrasonic transducer is placed, on a liquid for atomization, introducing the liquid to the container, and atomizing the liquid in the container by ultrasonic waves. In this example, at least the liquid for atomization for giving buoyancy to a main body of the apparatus is necessary. Namely, since the liquids cannot be entirely used for atomization, utilization efficiency of the chemicals is poor if the liquid is used for the chemical-containing liquid. Naturally, it is difficult to switch the chemicals to be contained in the mist. As compared with the conventional example, the effects of the present invention are clear as described above.

Meanwhile, if the chemical-containing liquid is, while being directly filled on the ultrasonic transducer, used like the portable ultrasonic humidifier of the above-mentioned conventional example, Thin protection films, such as stainless steel, titanium, or the like on a surface of the ultrasonic transducer, may be corroded into holes. In the present invention, since liquids without a corrosive action, such as water, are utilized for the above-mentioned ultrasonic propagation medium (Liq1), and the chemical-containing liquid (Liq2) is atomized through the medium, so that the above-mentioned problems cannot be found, thus providing high reliability.

Effects According to Means 3

In the present invention, there is used a new concept the ultrasonic propagation medium Liq1 is utilized, and the ultrasonic waves are switched to irradiate to any of a plurality of liquids for atomization Liq2 far from the ultrasonic transducer 40 to thereby atomize the Liq2.

as shown in, for example, FIG. 10, FIG. 19, FIG. 20, and FIG. 21 different types of chemical-containing liquids (Wa, Wb) are poured into the plurality small liquid containers (20, 20b) with the ultrasonic transparent film (23), the small liquid containers are held so that the ultrasonic transparent film may contact with the ultrasonic propagation medium (Liq1), and the ultrasonic waves are irradiated to the liquid arbitrarily selected among the plurality of chemical-containing liquids, thereby allowing the chemicals to be contained in the mist to be switched and discharged in very short time. It is also possible to mix them to be discharged. Namely, the chemical-containing mist can be generated according to user preferences.

In FIG. 10, FIG. 19, and FIG. 20, only by rotating the ultrasonic transducer (40), the chemical-containing mist can be switched at high speed. Moreover, in FIG. 21, by exchanging and inserting the above-mentioned plurality of small liquid containers (20, 20b) into the ultrasonic propagation path, the chemical-containing mist can be switched at high speed.

Since the air flow generating means, such as a fan or the like, and the droplet dispersed liquid collecting function can be eliminated using the ultrasonic reflection tube (27 or 29) described in the above-mentioned means 1 in combination, the apparatus for atomizing the plurality of chemical-containing liquids can be constituted in small size and economically.

Features thereof will be supplementarily explained concerning the above-mentioned effects as compared with the conventional example. For example, in a thin film deposition apparatus and a method for forming the thin film of Japanese Unexamined Patent Publication (Kokai) No. 2002-200447, there is disclosed the apparatus for generating mists of various mixing ratios to form a thin film on a substrate by changing a drive ratio of a plurality of ultrasonic transducers. However, there are problems in this apparatus that it is difficult to atomize a small amount of liquid since the liquid column pushed out by the ultrasonic waves is large as compared with that of the present invention, and the whole apparatus becomes large-sized since the liquid disperses in a wide range, so that it is not suitable for the apparatus for discharging the mist to users. Moreover, since a solution for forming the film directly contact with the ultrasonic transducer, the solution may degrade or destroy the ultrasonic transducer, thus causing a problem in reliability. Hence, the above-mentioned effects of the present invention are characteristic as also compared with this example.

Effects According to Means 4

Figure 4:
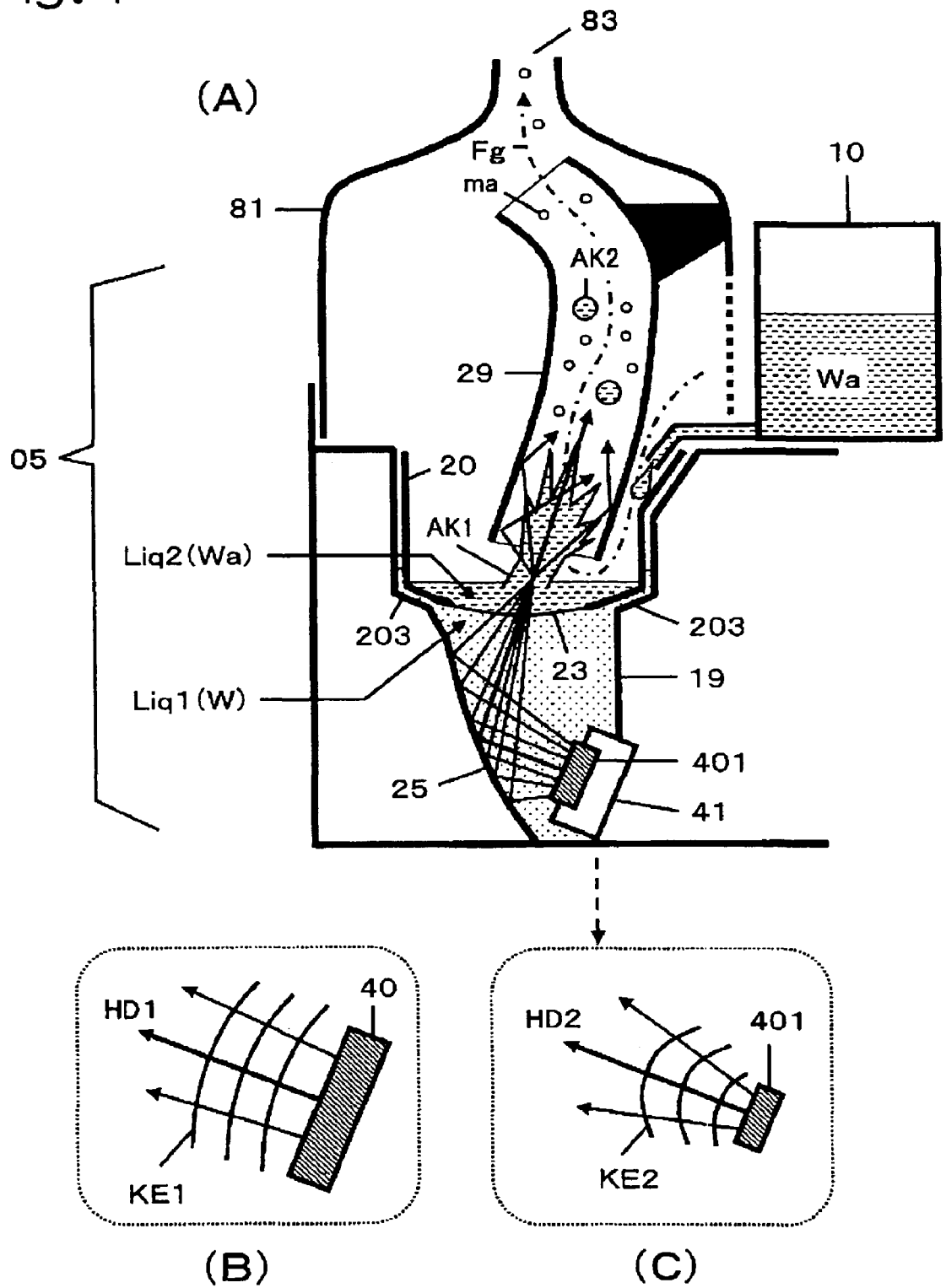
Figure 21:
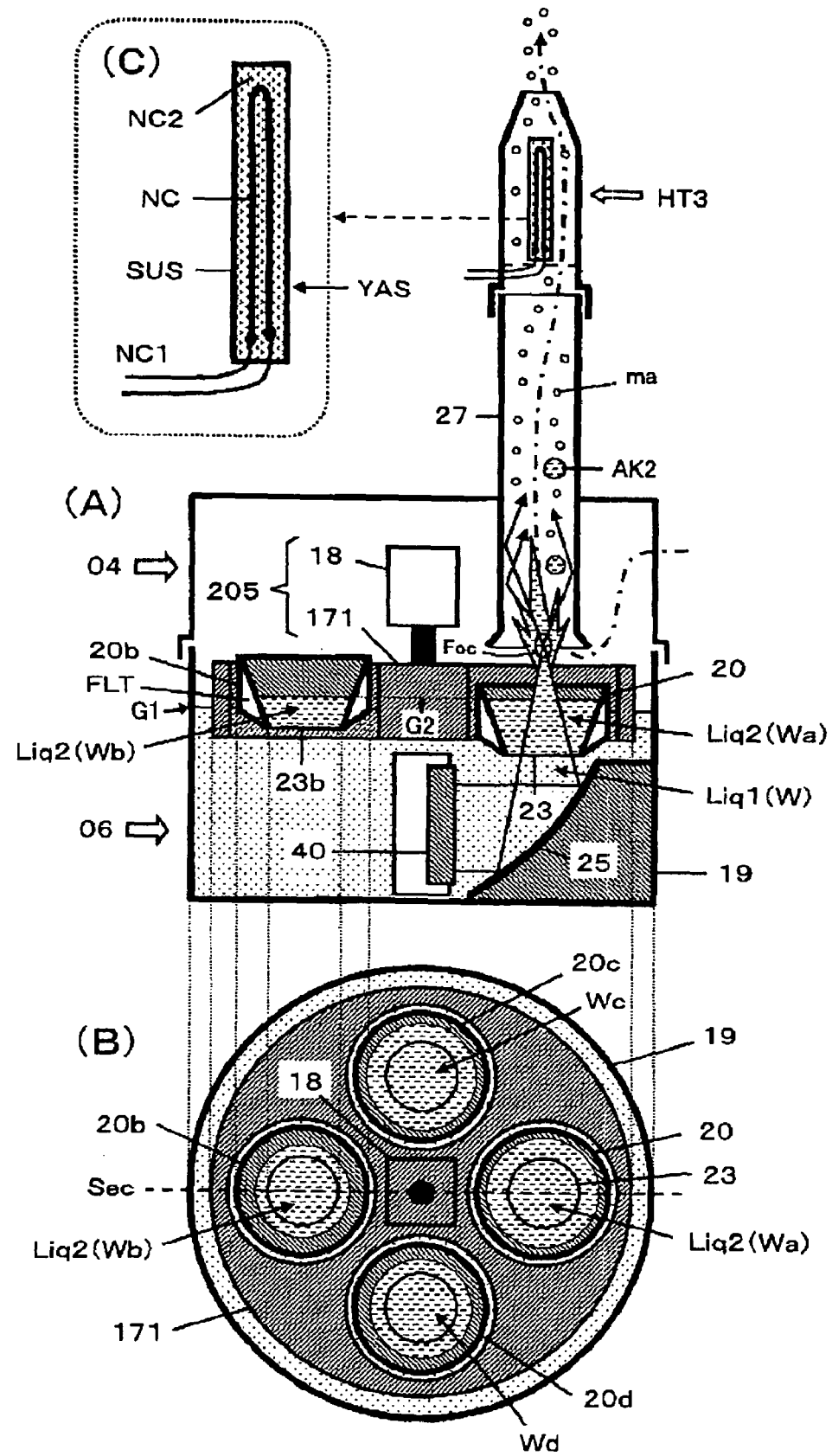

In the present invention, as shown in, for example FIG. 4, FIG. 19, and FIG. 21, the generated mist is carried upward by the traveling waves in the ultrasonic reflection tube (27 or 29). While an alternate long and short dash line is an air current path, the mist is always pushed up. Since atomization is promoted in the tube by the traveling waves and the mist goes to the tip of the tube, naturally a large amount of mist exists near the tip of the tube. Here, when the instant air flow generating means (74) shown in FIG. 1 and FIG. 13 is combined therewith; the mist pushed up will be discharged as an annular mass from a gun tube opening. Conventionally, since the mist generator has been large-sized, including it in the air gun has been difficult. In order to include it in the tube of the air gun, it is indispensable that the liquid atomization means is in a small size. According to the present invention, since a mist generating portion is small, it can be incorporated into the tube of the air gun.

Meanwhile, in FIG. 1 and FIG. 13, the ultrasonic reflection tube (27) for generating the mist is in the tube (81) for mist discharge. Hence, when the air pressure of 81 is increased by the instant air flow generating means (74), a large amount of mist will be annularly discharged like Lm. Particularly, in FIG. 13, the mechanism for generating various aroma-containing mists is arranged in the tube by employing characteristics of ability to make the mist generating mechanism small, and thus a small and highly efficient aroma switching annular mist generator can be achieved.

Since the annular mist has a property to flight straightly, it is possible to efficiently provide the aroma for users who are in distant locations. For example, a small amount of mist or vapor which contains the perfume can be presented to people's tip of nose at pinpoint. The chemicals (perfume) to be used are few and economical. An efficient perfume-containing mist generator can be achieved.

Appearance that the annular mist (Lm) changes a shape thereof while flying by the operation of the instant air flow generating means (air gun), and soon becomes thin and disappears is beautiful, thus providing visual healing effects. It becomes the mist generator for comfortably presenting the mist for users. By switching the type of perfume-containing mist at high speed to discharge it as a mass, The type of aroma can be locally changed even in the same room, and strength of aroma can be changed. Namely, fragrance space can be produced. Healing effects are increased combined with the above-mentioned visual fun.

When the tip of the tube (80) which discharges the mist is narrowed so that the cross section thereof may become about $2/3$ to $1/10$ compared with the stem of the tube, the annular mist (Lm) which has a beautiful shape and flies stably can be formed. The mass of the mist flies to a distance, and mood producing effects are improved.

The mist concentration measuring sensor (47, 48) is provided in the tube (80, 81) in which the above-mentioned generated mist is stored, and the mist is discharged upon detecting that the mist concentration became a predetermined range, thus allowing the annular mist (Lm) with beautiful shape to be formed certainly. The mass of the mist flies to a distance, and mood producing effects are improved.

By providing fluctuation to the discharge time of the above-mentioned annular mist (Lm), or providing fluctuation to the discharge speed thereof, further complicated changes occur, thus increasing fun to thereby increase the healing effects.

Features thereof will be supplementarily explained concerning the above-mentioned effects as compared with the conventional example. Conventionally, although there is an apparatus for discharging smoke of aroma balls or incense sticks using the principle of the air gun, there are no visual healing effects by discharging only the aroma balls, and in addition to that, there are problems that the discharge of the smoke of the incense sticks makes the switching of the aroma difficult and is bad for health or the like. Further, since the type of perfume-containing mist can not be changed in the conventional mist generator even when the conventional mist generator and the air gun are attempted to be combined, stage effects are hardly produced. Additionally, since the mist generator is large-sized, it is difficult to include it in the air gun, and it is not practical. Hence, the above-mentioned effects of the present invention are characteristic as also compared with this example.

Effects According to Means 5

As shown in FIG. 10, FIG. 18, FIG. 21, and FIG. 27, the mist is carried to the tube upper part by the traveling waves generated inside the ultrasonic reflection tube (27 or 29), the heat ascending air current is generated in the mist discharge passage by heating the inside of the tube or the tube upper part to thereby carry the mist further upward, and it is then discharged outside.

The mist straightly goes up from the opening of the tube like pulling strings. Namely, it is possible to generate natural fluctuation in the movement of the mist to discharge it beautifully. This appearance reminds smoke of incense sticks, thus providing the visual healing effects. In commercialization, it is an important appeal point.

Incidentally, although there are some people who dislike the smoke of the incense sticks because of disadvantages, such as throat pain or the like in spite of the visual beauty, it is healthy since components thereof are perfumes and medicines although the mist of this apparatus looks like smoke, so that it is accepted by most of the people.

When the above-mentioned heating means is used, evaporation will be promoted and the mist within the ultrasonic reflection tube will become still smaller fine-particles. When the liquid for atomization is the perfume, evaporation thereof will further improve smell characteristics as far as the mass is the same. Namely, it becomes a perfume-containing mist generator with sufficient perfume utilization efficiency.

When the above-mentioned heating means is not provided as shown in FIG. 24(B), even when the mist is forcibly discharged to the outside of the apparatus using the air flow generating means (70) or the like, a part thereof may drop and contaminate the circumference of the apparatus. However, when the heating means is used as shown in FIG. 24(A), the mist is discharged from the opening of the discharge tube (80), goes up, and is evaporated soon. Hence, it is rare to contaminate the circumference thereof, resulting in easy maintenance.

When the ascending air current due to heat is used in addition to carrying the mist using the ultrasonic reflection tube (27 or 29) as shown in FIG. 10, FIG. 18, FIG. 21, and FIG. 27, the air flow generating means for discharging the mist outside can be completely eliminated. It is effective for down-sizing and economization of the apparatus. New products such as a small electronic incense burner, a portable aroma generator, and the like, which have not existed in the former, can be achieved.

When the temperature of the mist or vapor near the heating means (HT1) is set to a temperature higher than the room temperature by 5 degrees Centigrade or more, and lower than that by 50 degrees Centigrade or less, the mist goes up beautifully and calmly, without dropping. Moreover, natural aromatics can be used as the chemicals.

As shown in FIG. 27, a chemical occlusion mechanism (07) may be provided over the heat ascending air current. Since the mechanism is used in a situation where moisture is always provided by the heated mist it is rare for the chemicals to strongly adhere to the inside thereof, resulting in relatively easy cleaning by washing in cold water or the like. The perfume within the plate is evaporated while floating up as if a steam iron floats and removes dirt in textiles.

Effects According to Means 6

Figure 26:
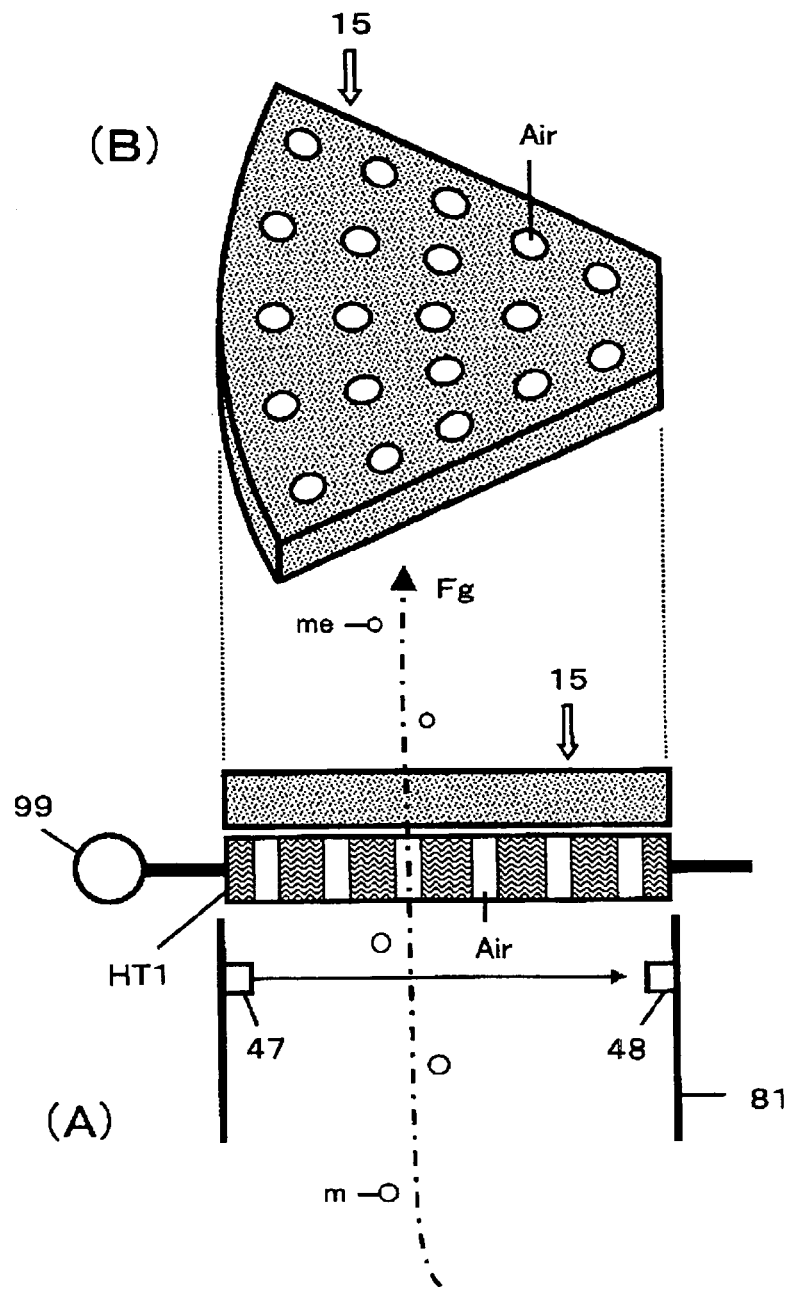

When the chemical (perfume) occlusion mechanism (07) of meshed shape is provided over the liquid atomization means (05) that uses the ultrasonic waves, and the perfume evaporated by the heating means is mixed into the mist to be discharged, as shown in FIG. 25, FIG. 26, and FIG. 27, it has a very mild and is felt soft since it is the aroma properly containing moisture. Since this aroma is discharged for a long time, comfortable aroma space is formed.

In the present invention, since a part of the mist acts so as to supply moisture to the chemical-containing material (07), the chemical (a, b, or the like) is evaporated (consumed) little by little, while the concentration thereof is diluted. Hence, the mist or vapor that contains the chemicals can be discharged over a long time. In an experiment in which a liquid perfume (essential oil) is used, there has been obtained a result that the aroma continues for a longer time by about two to five times as compared when using a dry ascending air current without moisture. Since the chemicals are consumed little by little while the concentration thereof is diluted, chemicals with high concentration can be used for the chemicals. Since the chemicals are efficiently consumed without waste, it requires less replenishment frequency. It is easy to use and economical.

Additionally, different chemicals are stored in the chemical-containing material (07) having a plurality of divided areas, and an arbitrary area is selected to pass a wet hot air flow therethrough, thus allowing the chemicals to be contained in the mist to be switched in a short time.

When means for switching to discharge the mist that contains various types of chemicals (perfumes) is used as the above-mentioned liquid atomization means (05) as shown in FIG. 27, and the mist that contains the chemicals (perfumes) is warmed up by HT1 to pass it through the chemical-containing material (07) that contains different chemicals (perfumes), Two types of chemicals (perfumes) are mixed to be discharged with the mist. Since there are many combinations, it is possible to easily form varied aroma space. Stage effects for healing are high. Specifically, while the mist (mb) that contains the perfume (b) is discharged in FIG. 27, when, from this state, the ultrasonic transducer (40) and the heating means (HT1) are rotated 180 degrees from a position shown in the same figure around the axis of rotation (91), the liquid (Liq2 (Wb)) in the small liquid container (20b) is atomized. Since the mist that contains the perfume (b) according to this atomization is warmed up by HT1, and pass through the chemical-containing material (07) that contains another perfume (a), two types of perfumes (a) and (b) are mixed to be discharged with the mist.

The chemical-containing material (07) with a structure as shown in FIG. 25(A) has excellent chemical-containing characteristics to the mist. Moreover, it is easy to remove and clean it, thus providing excellent maintainability.

Effects According to Means 7

Memory means (02a, 02b, 02c, or the like) for reading and writing information on the liquid for atomization (Liq2), or information on the chemicals (a, b, c) to be mixed in the mist is equipped as shown in FIG. 1 or FIG. 22, so that the information can be automatically read, and the information can be presented to users. Users readily confirm chemicals to be contained in the mist, resulting in fewer mistakes. Additionally, driving conditions can be automatically controlled according to the properties of the liquid for atomization or the chemicals to be mixed in the mist. Users can enjoy the favorite chemical-containing mist with easy operation.

When the chemicals are perfumes, it is possible to easily form varied aroma space. Additionally, since other comfortable sensory stimulations (visual stimulation, audio stimulation) suitable for the olfactory stimulation can be presented to users, space stage effects are high. Illumination information, video information, audio, music information, and the like corresponding to the smell impression of perfume are stored in the memory means.

Specifically, when a light in which color or intensity changes is irradiated to the mist (ma) or the tube (80) for discharging the mist (ma) according to the type of mist or the concentration of the mist by the illuminating device (85), perception expectation of the smell impression caused by the color happens to those who are looking at it. Here, when the mist is the perfume-containing mist corresponding to the smell impression, a sensory integrative action of the visual stimulation and the olfactory stimulation is generated, thus increasing the healing effects.

Additionally, when sound of streams, sound of water droplets, or the like, is generated according to the mist generation by an audio signal generator (Audio), the healing effects will be increased. When people are in the waterside, their minds will become calm. When water is visually produced by the mist, and water is audibly produced by the sound of stream and the sound of water drops, fantastic atmosphere can be produced by synergistic interaction. As the sound to be generated, sound of rain, sound of Suikinkutsu (water harp) sound of surf, sound of wind, sound of trees, or the like is effective other than this.

Particularly, when the mist (ma) is discharged as a mass (Lm) as shown in FIG. 1 or FIG. 13; visual and olfactory impressions are so strong that the healing effects are further increased if the above-mentioned illumination and the above-mentioned sound are presented according to the discharge of the mist.

When visual information and audio information corresponding to the perfume are downloaded from perfume company sites or the like by utilizing the Internet or the like to store them in the above-mentioned memory means, users can enjoy various mist representations which are the newest and suitable for their own preferences whenever they utilize the perfume. It is possible for perfume sales companies to promote the sales of the perfumes.

BEST MODE FOR CARRYING OUT THE INVENTION

First Embodiment

Figure 2:
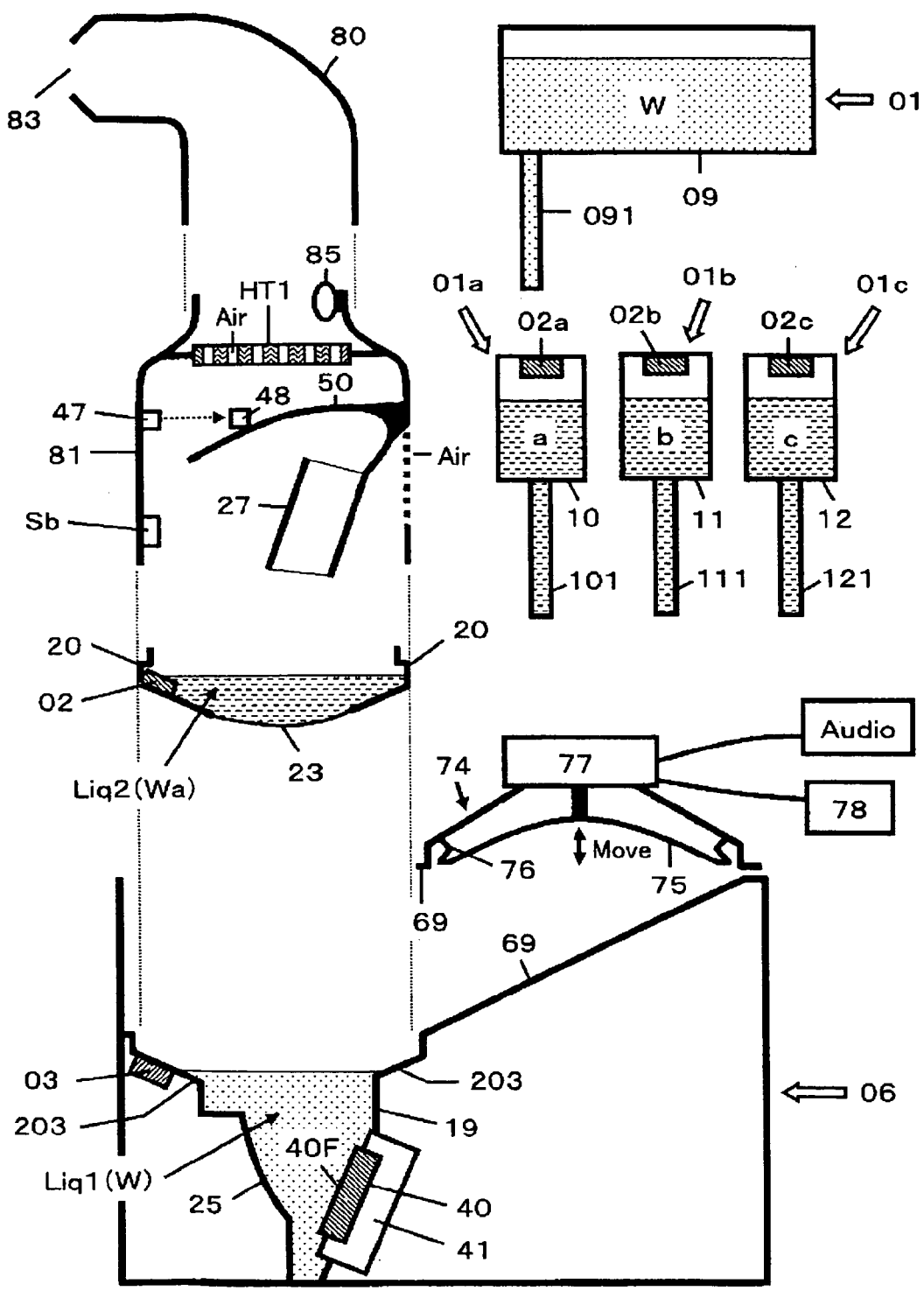
Figure 3:
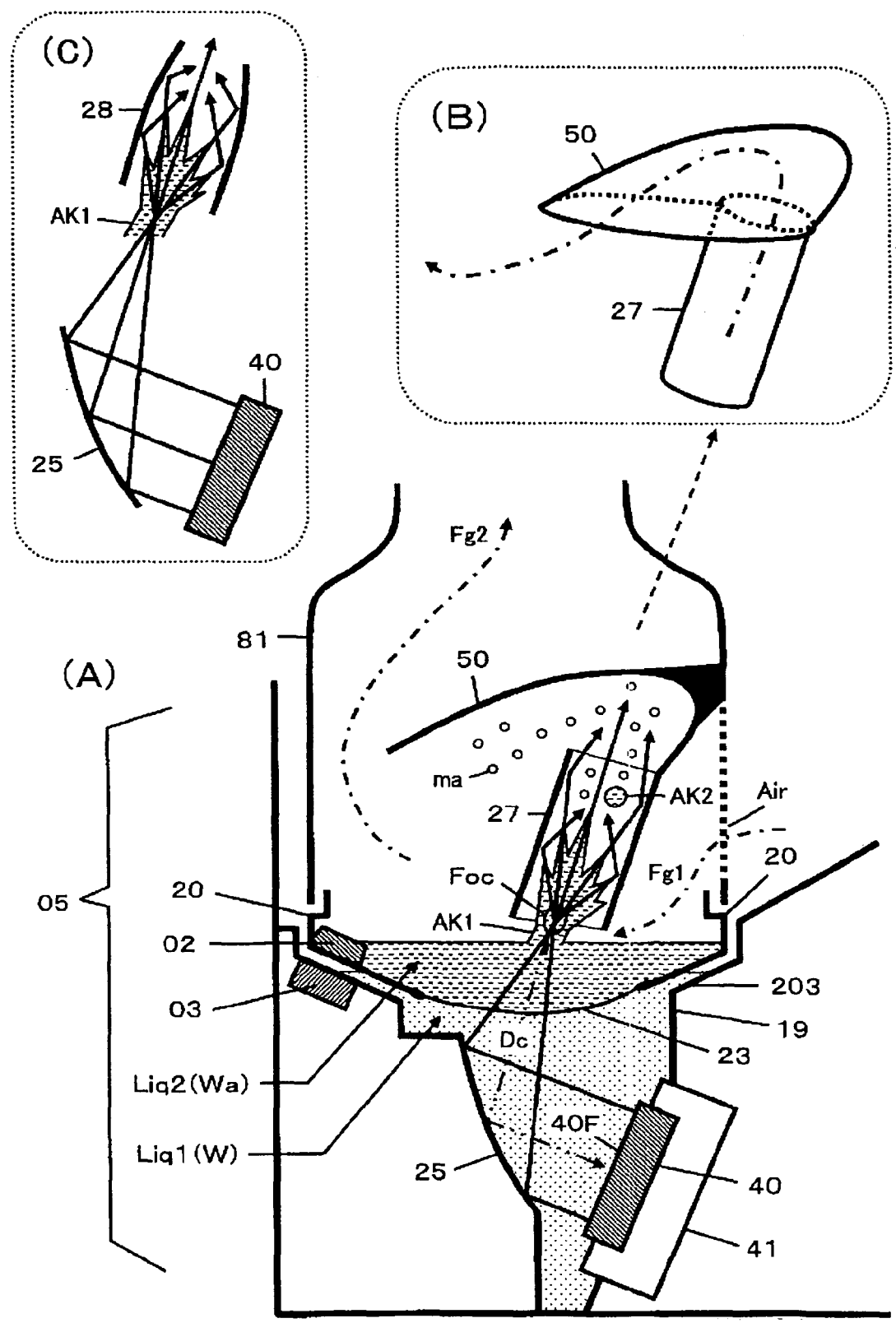

FIG. 1 is a first embodiment of the present invention, and shows a mist generator for discharging a mist or vapor which contains various chemicals to distant locations. FIG. 1(A) is a figure in which a longitudinal section of the apparatus is viewed from the side, and FIG. 1(B) is a top view in a state where an upper housing 04 is removed in FIG. 1(A). FIG. 1(A) shows the longitudinal section at dashed line Sec of FIG. 1(B). FIG. 2 is an exploded view showing a component constitution of the embodiment. Additionally, FIG. 3 is a view for describing in detail a portion which atomizes a liquid in FIG. 1.

In FIG. 1(A), reference numeral 05 represents means for atomizing the liquid, reference numeral 06 represents the lower housing, symbol HT1 represents heating means, reference numeral 80 represents a mist discharge tube, and reference numeral 74 represents means for instantaneously generating an air current (air gun).

First, a constitution of the means 05 for atomizing the liquid will be described. Reference numeral 40 represents an ultrasonic transducer, reference numeral 41 represents a mounting part of the ultrasonic transducer 40, reference numeral 19 represents a container into which an ultrasonic propagation medium Liq1 is put so as to fill a plane of vibration 40F of the ultrasonic transducer.

The ultrasonic transducer 40 is a piezoelectric plate element using ferroelectric ceramics, and it is driven at a high frequency of 1 MHz or more, preferably 2 to 3 MHz. The higher the frequency is, the smaller the particles of the mist become, and thus it is suitable for fragrance generators or the like. However, when the frequency is increased, a production technology for reducing a thickness of the ultrasonic transducer will be an issue. If it could be produced, an ultrasonic transducer of a driving frequency over 3 MHz can be naturally utilized. Reference numeral 43 represents a drive circuit of the ultrasonic transducer.

It is important that the ultrasonic propagation medium Liq1 has a thermal conductivity and a property to pass through the ultrasonic waves, and specifically, water (W), oil, alcohol, liquid resin, or the like may be used.

An ultrasonic convergence and reflection mechanism 25 is provided at a slant in front of the ultrasonic transducer 40. The reflection mechanism constitutes a concave mirror lens, and the ultrasonic waves generated in the ultrasonic transducer 40 are reflected by the concave mirror to slightly slantingly travel in an upward direction.

Means for holding a liquid for atomization Liq2 is provided over the ultrasonic concave mirror lens 25 so that it may contact with an end face of the ultrasonic propagation medium Liq1.

Here, the term "means for holding Liq2 so that it may contact with the end face of Liq1" represents means in which Liq1 and Liq2 are held while not being mixed with each other, namely in a state of being separated, and the liquid for atomization Liq2 is put over the ultrasonic propagation medium Liq1 so that the ultrasonic waves may pass through between both interfaces.

The liquid holding means is composed of the small liquid container 20 for putting Liq2 therein, which is provided with the ultrasonic transparent film 23 at the bottom; and is mounted so that the ultrasonic transparent film 23 may contact with the ultrasonic propagation medium Liq1. Reference numeral 203 is a mechanism section for mounting the small liquid container 20 detachably and attachably.

The liquid for atomization Liq2 may be poured into the small liquid container 20 from the outside. Additionally, the small liquid container can be removed from a main body of the apparatus to be cleaned.

At the bottom of the small liquid container 20, a hollow portion (concave surface) is formed into a liquid storage portion. The hollow portion is composed of the ultrasonic transparent film 23. Hence, as the liquid Liq2 in the small liquid container 20 decreases, the liquid gather on the ultrasonic transparent film 23.

As a material of the ultrasonic transparent film 23, the material whose specific acoustic impedance is close to that of Liq1 or Liq2 is preferable, but even when specific acoustic impedance is different, a material, as far as it is a thin film, can be used.

As a result of experiments, glass, vinyl chloride resin, rubber, stainless steel, paper, or the like may be used as the material. While a thin material in thickness is preferable, it is preferable that the thickness is 0.2 mm or less in the case of glass or metal with high hardness, and is 0.5 mm or less in the case of resin or rubber with low hardness.

Meanwhile, means (01, 01a, 01b, 01c in FIG. 1(B)) for pouring the liquid for atomization Liq2 is connected to the small liquid container 20. In FIG. 1(A), a state where water W and perfume a have been poured as Liq2 is shown. Symbol Wa means water that contains a chemical a.

Liquid medicines, alcohols, liquors, pesticides harmless to a human body, fungicide-mixing liquids such as a sodium hypochlorite, or the like is applicable to Liq2 other than the perfume-containing liquid. Since a surface tension and a viscosity of a water-based or alcohol-based liquid are small, the liquid will be atomized in an instant to disperse in the air when the output of the ultrasonic waves is increased. An atomization action is increased at 150 dB or more.

As shown in FIG. 2, the means 01 for pouring water is composed of a water container 09, a water pouring nozzle 091, and a fluid volume adjusting mechanism which is not shown in the same figure. Similarly, the means 01a, 01b, and 01c for pouring chemicals a, b, and c are composed of liquid containers 10, 11, and 12, liquid pouring nozzles 101, 111, and 121, and fluid volume adjusting mechanisms which are not shown in the same figure, respectively.

As shown in FIG. 1, the small liquid container 20 and the liquid pouring means 01a, 01b, and 01c are equipped with integrated memory circuits 02, 02a, 02b, and 02c for reading and writing pieces of information on the liquids, respectively. Moreover, signal transmission and reception circuits 03, 03a, 03b, and 03c are provided in positions facing to the integrated memory circuits in order to supply electric power to the integrated memory circuits and read the pieces of memory information.

Reference numeral 81 represents an air tube, and reference numeral 50 represents a dispersed liquid collecting mechanism attached to a part of the air tube.

Reference numeral 47 represents an LED and reference numeral 48 represents a photo-transistor, and a photo coupler is composed of both of them. The photo coupler is used to control a generation amount of mist. The above is the constitution of the means 05 for atomizing the liquid.

Next, a constitution of the heating means will be described. The heating means HT1 is provided in an upper part of the air tube 81 so as to cross the tube. Holes Air through which air passes are provided in HT1. Reference numeral 88 represents a drive circuit for energizing to HT1.

Next, the mist discharge tube 80 will be described. In FIG. 1(A), the tube is constituted so that a medial axis thereof may be curved to the left, and a cross section at the tip of the tube may become sharply small. Preferably, an opening 83 of the tube is formed small so that the cross section thereof may be about ⅔ to 1/10 as compared with that of the stem 80a of the tube. Angle α is a definition of a tip angle of the tube. A setting value will be described hereinbelow.

The tube is attached to an upper part of the above-mentioned heating means (HT1) so as to be inserted into the air tube 81. Since the mist discharge tube 80 can be rotated, the opening 83 can be directed to a predetermined direction.

Next, a constitution of the instant air flow generating means 74 will be described. Reference numeral 75 represents a turbinated film (paraboloidal film) for air compression, reference numeral 76 represents a bellows-shaped deformation film, reference numeral 77 represents a driving solenoid for pushing out the film 75 in a direction indicated by Move, and reference numeral 78 represents a solenoid drive unit. Reference numeral 69 represents a blowing tube for sending air compressed by operation of the instant air flow generating means 74 to the air tube 81.

Air pass holes Air are provided in a right surface (indicated by a dashed line) of the air tube 81, and the above-mentioned compressed air passes through Air from the blowing tube 69, as indicated by an alternate long and short dash line Fg1 to enter the air tube 81. The compressed air further passes through HT1, and passes through the mist discharge tube 80 to be discharged from the opening 83.

Next, an operation of the means 05 for atomizing the liquid will be described. In FIG. 1(A), a drive of the ultrasonic transducer 40 will generate the ultrasonic waves of high frequency from the plane of vibration. The ultrasonic waves travel in the ultrasonic propagation medium Liq1 as indicated by a solid line, are reflected by the ultrasonic concave mirror lens 25 to change the direction and are converged to go upward, and then pass through the ultrasonic transparent film 23 to reach the liquid for atomization Liq2.

Generally, transmission and reflection of the ultrasonic waves occur at border planes of the media which differ in specific acoustic impedance, but when the specific acoustic impedances of Liq1 and Liq2 are close to each other, and the ultrasonic transparent film 23 is thin; the ultrasonic waves are hardly reflected by the respective border planes and efficiently propagate to Liq2.

The ultrasonic waves have sharp directivity for high frequency. A liquid level of the liquid for atomization Liq2 is pushed up near a focal point Foc of the ultrasonic concave mirror lens 25 to thereby create a liquid column AK1.

The ultrasonic waves propagate to an upper part of the liquid column AK1, and reach a border plane with air. Since the specific acoustic impedances of the liquid Liq2 and air are remarkably different, the ultrasonic waves are almost reflected in a border plane between the liquid column AK1 and air. Since a liquid shape of an upper part of the liquid column is complicated as shown in the same figure, the ultrasonic waves repeat reflection in the upper part of the liquid column to vibrate the liquid at high speed. Namely, liquids mutually exercise heavily while repeating collision and dispersion. The liquid locally disperses.

In this case, particles of the liquid that present in a position near the air overcomes the surface tension of the liquid to change into fine-particles, and fly into the air. Thereby, a large amount of mist is generated. As shown in the same figure, when Liq2 is the liquid Wa which contains chemicals (perfumes or the like), chemical-containing mist ma is generated.

When the driving frequency of the ultrasonic transducer 40 is set to about 2.5 MHz, the mist ma will result in extremely small particles of below 3 micron diameter. If the mist has a size as large as this, it will have little moisture, and will have a property of drifting in space for a certain amount of time. Many particles are evaporated while drifting in the air. Moreover, a large amount of negative ions is generated upon atomization.

While the liquid which has not changed into the mist becomes a droplet dispersed liquid AK2 to be dispersed, it collides with the dispersed liquid collecting mechanism 50 and drops to be collected by the small liquid container 20, and returns on the ultrasonic transparent film 23.

Here, since ultrasonic energy is focused on the focal point Foc of the ultrasonic concave mirror lens 25, it is preferable to adjust a mounting angle and position of the lens 25 and a fluid volume of the small liquid container 20 so that the liquid column AK1 may come near this focal point Foc. In FIG. 1(A), the focal point Foc of the lens 25 is set near the liquid level of the liquid storage portion on the ultrasonic transparent film 23.

The mounting part of the ultrasonic transducer 40, the ultrasonic concave mirror lens, and the small liquid container mounting mechanism 203 can be integrally molded using plastics or the like (integrally molded product 1). The ultrasonic transducer 40 can be attached to the molded product 1.

Meanwhile, the small liquid container 20 can be integrally molded using plastics by determining a liquid level in advance and designing a shape so that the liquid level may be near the focal point Foc (integrally molded product 2). The ultrasonic transparent film can be attached to the molded product.

Additionally, an ultrasonic reflection tube 27, the dispersed liquid collecting mechanism 50, and the air tube 81 can be integrally molded using plastics (integrally molded product 3).

The above-mentioned integrally molded products 1, 2, and 3 can be integrated by a fitting mechanism. Thereby, a position of each component can be set so that atomization efficiency may be increased.

Next, the reason why the liquid Liq2 (Wa) can be efficiently atomized by setting as this will be described using FIG. 3(A) in which a cross section of the liquid atomization means 05 is scaled up. Although an ultrasonic plane mirror may be used as the ultrasonic reflection mechanism which changes the direction of the ultrasonic waves, energy can be focused by using the ultrasonic convergence and reflection mechanism, for example, the concave mirror lens 25 as shown in the same figure. By this focusing, the liquid column AK1 becomes short, namely, the liquid Liq2 locally disperses to be atomized near the lens focal point Foc.

That the atomization is local makes it possible to shorten a distance from the plane of vibration 40F of the ultrasonic transducer to the position where the mist is generated (alternate long and two short dashes line Dc in the same figure), so that the ultrasonic energy is efficiently used for atomization. According to the constitution of the present invention, when a diameter of the ultrasonic transducer is about 1 cm, Dc can be set to around 2 cm. Since the distance is short, the large ultrasonic energy is focused near the liquid level of the liquid storage portion, thereby generating a large amount of mist.

Incidentally, in the conventional mist generator shown in FIG. 28, since the liquid column AK1 pushed out by the ultrasonic waves is high (long), and atomization occurs in a range shown in AK1C of the upper part of the liquid column, the distance Dc from the plane of vibration indicated by the alternate long and two short dashes line in the same figure to the atomization position becomes long compared with that of the present invention, thus causing less atomization efficiency. According to experiments using a similar ultrasonic transducer, Dc is about 5 cm in the constitution shown in FIG. 28, the mist has been generated at a position having a distance longer than by two times from the plane of vibration as compared with that of the present invention. The amount of mist according to present invention is much higher.

Further, in the embodiment shown in FIG. 3(A), the ultrasonic reflection tube 27 is provided so that the liquid for atomization (Liq2) pushed out in the air by the ultrasonic waves may be surrounded, while paying attention to that the atomization locally occurs. Additionally, it is provided in a position where air enters from the lower part of the tube. The ultrasonic reflection tube acts so that the ultrasonic waves that circumferentially scatter in the position where the liquid disperses may be again converged into the tube to travel in the axial direction. The solid line arrow indicates this behavior in the tube in the same figure. Since the inside of the tube is filled with the ultrasonic waves, the liquid with large particles is further atomized by the ultrasonic waves.

Hence, unlike the conventional guide for discharging the mist, the ultrasonic reflection tube 27 has actions for increasing the amount of atomization by secondary-using the scattered ultrasonic waves, and giving a pressure to the mist to push out it. Since the ultrasonic energy is consumed extremely efficiently for atomization and mist discharge, the amount of mist is increased by about 50% compared with a case where the ultrasonic reflection tube 27 does not exist. Additionally, the particles of the mist are made finer to be uniform. Preferably, the diameter of the tube is about 5 mm to 2 cm. Preferably, the length thereof has a length in which the reflection is repeated. Incidentally, a setting method and effects of the ultrasonic reflection tube 27 will be hereinafter described in further detail in a description of FIG. 5 and FIG. 6.

A constitution shown in FIG. 3(C) is designed such that the ultrasonic waves focus on the inside of the tube by changing a cross section of an ultrasonic reflection tube 28 in an axial direction to make a cross section closer to the end small. Atomization efficiency is further improved, so that a large amount of mist blows out from the tip of the tube.

When the amount of generated mist according to the constitution shown in FIG. 3(A) is compared with that of the conventional mist generator shown in FIG. 28 which is not provided with the ultrasonic concave mirror lens 25 and the ultrasonic reflection tube 27, it is possible to increase it by about three times or more by using the same ultrasonic energy.

Although FIG. 3(A) shows a case where there is a space between the lower part of the ultrasonic reflection tube 27, and the liquid level of the liquid Liq2 (Wa), the lower part of the tube may be touched to the liquid if air holes are provided in the side of the lower part of the tube for air to enter into the tube. Namely, what is necessary is to just be constituted so that air may be introduced to the inside of the tube from the lower part of the tube below the position where the ultrasonic waves are scattered.

The dispersed liquid collecting mechanism 50 is provided near the tip of the ultrasonic reflection tube 27. FIG. 3(B) shows an outside view of a structure in which the dispersed liquid collecting mechanism 50 and the ultrasonic reflection tube 27 are integrated. Since atomization is local, and further the mist is gathered by passing through the ultrasonic reflection tube 27 as described above, the dispersed liquid collecting mechanism 50 can be constituted in small size. Since collection of the liquid is fast if it is constituted in small size, cycles of liquid dispersion, atomization, droplet liquid collection, and liquid dispersion efficiently proceeds. The liquid Liq2 can be thoroughly atomized to be used up.

As described above, the liquid atomization means 05 of FIG. 1 or FIG. 3 can intensively irradiate the ultrasonic waves to a small amount of liquid through the ultrasonic transparent film to thereby atomize it efficiently. It can be constituted in small size, either.

Although the direction of the ultrasonic waves reflected by the ultrasonic concave mirror lens 25 may be vertical, a traveling direction HD of the ultrasonic waves is inclined at an angle θ from the vertical in FIG. 1(C). If it is constituted as described above, the ultrasonic waves try to travel straightly, whereas the liquid column AK1 tries to turn to the right-hand side due to receiving downward gravity. Since the ultrasonic waves propagate in the liquid column only for a short distance and collide with a side surface of the liquid column, the ultrasonic energy is efficiently consumed for atomization to increase the amount of mist. The angle θ is effective when it is 5 degrees or more. Hereinafter, it will be described in detail in an embodiment shown in FIG. 17.

The dispersed liquid collecting mechanism 50 may be formed in a dome shaped container, which has a depth in the traveling direction of the ultrasonic waves as shown in FIG. 3(B). Since the circumambient air is moved together by the discharge of the mist to thereby form an air current, a weak air current which transmits along the edge of the container is generated in the dome shaped container, as indicated by a alternate long and short dash line in the same figure. The mist rides on this air current and it is carried to the outside of the dome shaped container 50. The droplet dispersed liquid collides with the wall of the dome and drops by gravity. Thus, separation of the mist and the droplet dispersed liquid is performed.

Since the difference between the specific acoustic impedances of Liq1 and air is extremely large in a state where the liquid in the small liquid container 20 has thoroughly been consumed, a part of the ultrasonic waves reflects downward at a position of the ultrasonic transparent film 23 after propagating through Liq1, and as is clear from the structure shown in FIG. 3(A), the reflected waves do not return toward the ultrasonic transducer 40 directly but are diffused in the ultrasonic propagation medium Liq1. Namely, safety of the ultrasonic energy is high since it does not act to heat the ultrasonic transducer 40.

A distance between the ultrasonic transducer 40 and the ultrasonic transparent films 23 can be further reduced by using this property. Since the ultrasonic transducer 40 is neither degraded nor destroyed even when the distance is reduced, it is effective for an increase in efficiency of atomization and a reduction in size of the apparatus.

Moreover, since a small amount of liquid is put into the small liquid container 20, and the liquid can be thoroughly atomized and used up, it is possible to perform a driving method in which, after atomizing and using up the chemical-containing liquid, a next type of chemical-containing liquid is put therein to atomize it again.

As shown in, for example, FIG. 1(A), it is possible to use water Wa containing the perfume a first, to use water Wb containing the perfume b next, and to use water Wabc containing the perfumes a, b, and c further, or the like. Designing to atomize a small amount of liquid makes it possible for the type of perfume-containing mist to be switched in short time and discharged.

Although there occurs a problem that if the perfume-containing liquid poured into the small liquid container 20 remains without being able to be used up, it will be mixed with a perfume to be newly poured, if it is controlled to pour the next perfume-containing liquid after thoroughly using up the previous one like the present embodiment, switching of the aroma is clear.

Next, an operation of the means for discharging the mist or vapor will be described. In FIG. 1(A), when the heating means HT1 is energized, the circumambient air is warmed up to thereby generate an ascending air current indicated by an alternate long and short dash line Fg2. The above-mentioned generated mist ma also rides on the ascending air current to go up. In this case, evaporation of the mist is promoted with the heat and particles become still smaller.

When the liquid for atomization is the perfume, evaporation thereof will further improve smell characteristics as far as the mass is the same. Hence, heating the mist can further efficiently present the aroma with a small amount of liquid perfume. A temperature range between 30 degrees Centigrade to 50 degrees Centigrade is suitable for a temperature of heating the mist.

Note herein that, when there are few ascending air currents due to the above-mentioned heat, and the mist does not reach the air discharge tube 80, slightly and slowly operating the air flow generating means 74 can enhance the air currents Fg1 and Fg2.

The above-mentioned warmed mist or vapor is accumulated in the upper part of the air discharge tube 80. When the inside of the tube is filled, overflowed mist or vapor will be gradually discharged from the opening 83 to then go up.

Here, when the turbinated film 75 for air compression of the instant air flow generating means 74 (air gun) is largely and quickly operated by the driving solenoid 77, the air pressure in the blowing tube 69, the air tube 81, and the mist discharge tube 80 is increased, so that the mist ma or vapor accumulated in the mist discharge tube 80 proceeds along a path indicated by an alternate long and short dash line Fg3 and is discharged from the opening 83 at once as a ring-like mass Lm. Incidentally, symbol Move in the same figure indicates a move of the above-mentioned turbinated film 75.

Here, in order to form the beautiful annular mist Lm, a concentration of the mist and a structure of the tip of the air discharge tube 80 are important. In the same figure, the tube cross section at the tip is constituted so as to be sharply thin with a constant slope. The tip angle α is preferably in a range of 20 degrees Centigrade to 80 degrees Centigrade, more preferably around 45 degrees Centigrade.

The annular mist Lm flies without breaking down a form thereof in a state where there is no wind. It is possible to fly a distance of about 5 m from the discharge opening 83. Directing the opening 83 of the air discharge tube 80 to users to discharge the annular mist Lm makes it possible to send the chemical (perfume a) to users in distant locations while keeping the concentration high. Smell characteristics are extremely good.

Here, when the heating means HT1 is not used or the temperature of HT1 is low, an evaporation speed of the mist (liquid fine-particles) is slow. The above-mentioned annular mist Lm visibly flies at first, and then gradually becomes thin and disappears. When people see this slow change of state of the mist, their minds will be healed.

Meanwhile, when a heating value of the heating means HT1 is increased, and the mist is heated at high, temperature to be discharged, evaporation of the mist (liquid fine-particles) is promoted, and the above-mentioned annular mist Lm is discharged from the opening 83 in a state of an invisible aroma. These can be selected according to the purpose of use.

Since the perfume-containing mist or the perfume-containing vapor can be discharged while pinpointing a target as described above, the type of aroma can be locally changed even in the same room, and strength of aroma can be changed. Namely, aroma space can be produced. Additionally, since it can be presented at pinpoint, it requires less perfume to be used.

It should be noted that since the liquid atomization means 05 of the present invention can be constituted in small size as described above, it is possible to integrate it with the instant air flow generating means 74 (air gun) to be incorporated into the main body of the apparatus.

Next, functions of the photo coupler 47 and 48 provided in the air tube 81 will be described. Generally, in the mist generator using the ultrasonic waves, since currents energized to the ultrasonic transducer and the amount of generated mist are not linear, it is troublesome to gradually control the amount of generated mist. It is necessary to tune the current finely, while visually looking at the generation amount of mist. The above-mentioned photo couplers are used for solving this problem.

Supposing that an output of the LED 47 is constant, when the mist passes through between the LED 47 and the photo transistors 48, light will be interrupted if the amount of mist increases, thus causing a decrease in an output of the photo transistor 48. Namely, the amount of mist is detectable by measuring the output.

Hence, if a relation between the energization currents to the ultrasonic transducer and the amount of mist is measured in advance and, a calibration table is created, the amount of mist can be selected gradually. For example, if about five steps of levels are set, users can obtain a desired amount of mist by selecting the level.

Meanwhile, in the operation of the above-mentioned instant air flow generating means (air gun) 74, although it is difficult to discharge beautiful annular mist if the mist concentration of the air tube 81 or the air discharge tube 80 is not within a predetermined range, it is possible to certainly form the beautiful annular mist if the mist concentration is detected by the above-mentioned photo coupler to drive the air gun with a suitable concentration.

The above-mentioned photo coupler may also be utilized as means for detecting a liquid residual amount of the small liquid container 20. When the amount of mist decreases, controls to add and pour the liquid and to change the type of liquid are possible based on a judgment that there is little liquid residual amount.

Next, functions of the integrated memory circuit will be described in FIG. 1. The means 01, 01*a*, 01*b*, and 01*c* pour the liquid pour into the small liquid container 20. Although the water pouring means 01 is not mistaken since a shape of the container 09 is different from that of other three containers, the containers of means 01*a*, 01*b*, and 01*c* for pouring the chemicals tends to be mistaken in attachment since the shapes are similar.

When users attempt to select and evaporate the chemicals according to their preferences, it is preferable to display information on what type of liquid containers are attached to setting positions of the liquid pouring means.

The integrated memory circuits (IC tag) 02*a*, 02*b*, and 02*c* are means for notifying the pieces of information on the liquids contained in the containers to the main body of the apparatus. For example, the information on the perfume a contained in the container 10 is stored in the integrated memory circuit 02*a*.

When liquid pouring means 01*a*, 01*b*, and 01*c* are mounted as shown in FIG. 1(B), the pieces of information stored in the integrated memory circuits are read by the electric power supply and signal transmission/reception circuits 03*a*, 03*b*, and 03c. This information can be displayed on a display through a control processing unit which is not shown in the same figure to be notified to users. Hence, users can rightly select the chemicals that are desired to be evaporated.

Additionally, reading the information on the liquid makes it possible to drive the ultrasonic transducer 40 or the heating means HT1 under a predetermined condition. For example, it is possible to automatically change the heating temperature and change the generation amount of mist, or the like according to the type and the concentration of the chemical.

Next, a method for increasing the healing effects by presenting sound, music, light, image, or the like corresponding to smell impressions when the perfume-containing liquid is atomized will be described.

Sense information, such as visual information, audio information, or the like, corresponding to a smell impression of the perfume is stored in advance in the integrated memory circuits 02a, 02b, and 02c, as above-mentioned information on the liquid, and when the aroma is presented to users, sensory stimulations can be presented together with it based on the visual information or the audio information. An integrated function of the sensory stimulations of an olfactory sense, a visual sense, and an auditory sense is generated, thus increasing the healing effects.

Illumination information or video information corresponding to the perfume liquid is included in the visual information, and the sound information or music information corresponding to the liquid is included in audio information.

Writing of liquid relevant information to the above-mentioned integrated memory circuit (IC tag) can be performed in advance by perfume sales companies or the like. Moreover, it can be transmitted from perfume sales companies or the like using communication means. In this case, home page addresses of the perfume sales companies or the like on the Internet may be recorded on the integrated memory circuit. The information can be downloaded by accessing the address from the main body of the apparatus.

Next, a method for generating sound having the healing effects will be concretely described. In FIG. 1(A), sound corresponding to the smell impression of the perfume a can be generated by the audio signal generator Audio to present them using the instant air flow generating means 74. Although the instant air flow generating means 74 is the instant air flow generating means as described above, it can be used also as an audio generator because of a loudspeaker structure.

Operation examples of the above-mentioned Audio are as follows. In FIG. 1(A), when the droplet dispersed liquid AK2 is collected in the small liquid container 20 as described above, sound or vibration is generated by the liquid.

Sb is a sensor for detecting the sound or vibration. Sb and Audio are connected to each other by a circuit which is not shown in the same figure. The sound or vibration is processed by Audio to generate audio signals, and is sounded from a loudspeaker 74.

Processing by the Audio includes calculating a frequency spectrum of signals of the above-mentioned sensor, respectively emphasizing or suppressing low pitched sound, medium pitched sound, and high pitched sound to reconstruct them, or the like. It is also possible to generate echoes. Such frequency characteristic conversion can be performed according to the type of aroma. The processing also includes activation processing (trigger processing) for detecting movement of the liquid to generate sound.

It is possible to provide such changes that light and rhythmical sound of water drops is used for a citrus aroma, such as lemon, grapefruit, lime, or the like, which is known as a fresh aroma, by increasing high frequency components, and low and calm sound of water drops is used for a floral aroma, such as rose, ylang ylang, or the like, which is known as a heavy aroma.

The above-mentioned Audio can also perform still more advanced sound processing, including removing noise components that people feel uncomfortable from the above-mentioned sound of water drops or the sound of vibrations, providing fluctuation to a sound pitch or loudness, composing sound to be felt comfortable using the sound of water drops or sound of vibrations as a trigger, or the like. Sound and music from another sound source can also be generated based on trigger signals generated based on movement detection results of the above-mentioned liquid.

Further, when the annular mist (Lm) is discharged, it is also possible to generate sound at timings immediately before or immediately before the discharge.

Sound to be felt comfortable includes sound of water drops, sound of Suikinkutsu (water harp) sound of rain, sound of surf sound of stream, sound of wind, sound of trees, or the like. Additionally, these tones can be changed according to the type of aroma. When an aroma image and a sound image are compiled so as to correspond to each other, a sensory integrative action of the olfactory stimulation and the audio stimulation occurs, thus increasing the healing effects.

For example, when a marine-like aroma and the sound of surf are combined, an image of relaxing while hearing the surf in the summer resort of the beach is obtained, and when a forest-like aroma, and the sound of trees and the sound of stream are combined, an image of relaxing while hearing the sound of calm wind in deep quiet mountains can be created.

Particularly, since the visual and olfactory impression is strong when the annular mist Lm is discharged as described above, if the sound, such as "zabun, zabun" when it is the sound of surf, "pin, pin" when it is the sound of Suikinkutsu, or the like is presented together with the discharge of Lm, the healing effects is further increased.

Further, in order to increase sound quality, it is also possible to make the air tube 81, the air discharge tube 80, the lower housing 06, or the like from ceramics. Thereby echo characteristics are improved.

In FIG. 1, reference numeral 85 is the means for illuminating the inside of the air discharge tube 80 and the annular mist Lm, the means being provided in the upper part of the air tube 81. The light of the color corresponding to the above-mentioned smell impression can be irradiated. The means 85 can use red, green, and blue LEDs in combination, and the light of various colors can be irradiated by changing a power ratio of three types of LEDs. The color of the light irradiated to the air discharge tube 80 and Lm appropriately changes with the type and concentration of the aroma to be discharged. Moreover, it is possible to control so that illumination intensity may change with the concentration of the mist. It is preferable that the color of the illumination has a positive correlation between a psychological action of the aroma and a psychological action of the color.

When illuminated according to the discharge of the annular mist Lm, a perception expectation of the smell impression that "the aroma will come from now on" will happen to users by the color. Here, if the aroma to be presented is an aroma of the same type of image imagined from the color, a sensory integrative action of the olfactory stimulation and the visual stimulation occurs, thus increasing the healing effects.

Specifically, a light green color is effective to an aroma of eucalyptus, peppermint, or the like having an air freshening effect, a warm orange color is effective to an aroma of sweet orange, mandarin, or the like having a bright positive impression, a light purple or blue color is effective to an aroma of lavender having a calm impression, a light pink or red color is effective to an aroma of ylang ylang having an attraction effect, a light yellow color or the like is effective to an aroma of grapefruit, lemon, or the like having a refreshing effect. It is possible to produce healing space in visual and olfactory sense by the controls described above.

In the present embodiment, the area where the liquid disperses within the apparatus is limited only to the inside of the small liquid container 20, the inside of the air tube 81, and the inside of the air discharge tube 80. Moreover, since each structure can be easily disassembled as shown in FIG. 2, it is easy to clean, thus providing excellent maintainability.

In FIG. 1, the small liquid container 20 and the liquid pouring means 01, 01a, 01b, and 01c can be made into a cartridge-type. By exchanging the cartridge, it is possible to atomize or evaporate the liquid which contains various chemicals to be discharged. It will be described in an embodiment shown in FIG. 14 and FIG. 21 in more detail.

FIG. 4(A) is a sectional view of another configuration example about the liquid atomization means 05 of the above-mentioned first embodiment. Different portions as compared with FIG. 3 will be described. Reference numeral 401 represents a small ultrasonic transducer. Reference numeral 29 represents an ultrasonic reflection tube constituted so as to bend the tube. In FIG. 4, the ultrasonic reflection tube 29 also serves as the function of the dispersed liquid collecting mechanism.

An operation thereof will be described. When the ultrasonic transducer is made small, the ultrasonic waves emitted from the ultrasonic transducer will be diffusive rather than flat. This behavior is shown in FIGS. 4(B) and 4(C). FIG. 4(B) is the behavior of the ultrasonic waves emitted from the ultrasonic transducer 40 used in FIG. 1, FIG. 2, and FIG. 3. Symbol KE1 is a wave surface and symbol HD1 is a traveling direction of the wave surface. FIG. 4(C) is the behavior of the ultrasonic waves emitted from the small ultrasonic transducer 401. The wave surface KE2 is further curved than that of KE1, and the traveling direction HD2 of the wave surface has a spread wider than that of HD1.

Even if such small ultrasonic transducer is attached to the conventional mist generator shown in FIG. 28, losses of the ultrasonic energy are large, resulting in poor atomization efficiency. However, when the ultrasonic concave mirror lens 25 that has a sufficiently large size as compared with that of the small ultrasonic transducer 401 is used as shown in FIG. 4(A), the above-mentioned ultrasonic waves trying to diffuse are collected by the lens, allowing them to be reflected so as to converge on one spot. The losses of the ultrasonic energy are very low, thus causing extremely high atomization efficiency. Advantages using the small ultrasonic transducer are the ability of down-sizing the apparatus, constituting it at low cost, or the like.

The above-mentioned ultrasonic energy is focused near the liquid level of Liq2 (Wa), and disperses in the upper part of AK1. In this case, a large amount of mist ma is discharged to the inside of the tube. Since the ultrasonic reflection tube 29 is set so as to surround the liquid dispersion portion and to introduce air to the inside of the tube from the lower part thereof, the ultrasonic waves are scattered into the inside of the tube near the upper part of AK1, and travel the inside of the tube in an axial direction.

The droplet dispersed liquid AK2 is further atomized inside the tube. Simultaneously, the light mist is flown in the axial direction of the tube by the pressure of the ultrasonic waves. An air current as indicated by an alternate long and short dash line Fg is generated inside the tube due to the movement of the mist, the mist ma is discharged from the opening 83 of the air tube 81 through the upper part of the ultrasonic reflection tube 29.

Here, since the upper part of the tube is curved to the left, the droplet dispersed liquid AK2 with a large diameter collides with the wall of the tube, drops along the wall of the tube, and is collected in the small liquid container 20. Since it is rare for the droplet dispersed liquid to jump out of the upper part of the tube, the ultrasonic reflection tube 29 acts also as the dispersed liquid collecting mechanism. Hence, the dispersed liquid collecting mechanism 50 as shown in FIG. 1 and FIG. 3 can be eliminated.

Second Embodiment

Figure 5:
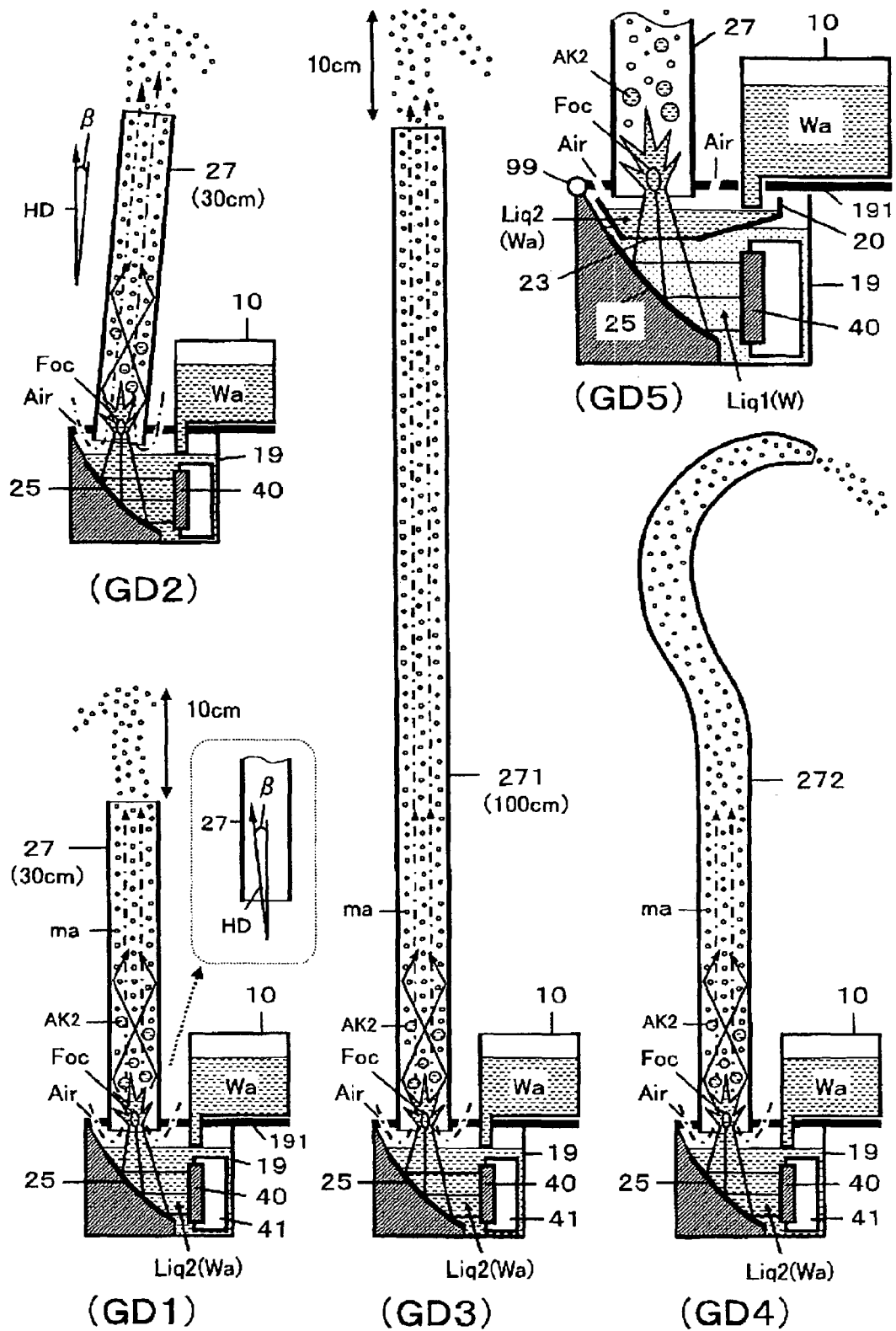

FIG. 5 is a second embodiment of the present invention, and shows a sectional view of the mist generator effectively using the ultrasonic convergence and reflection mechanism 25, the ultrasonic reflection tubes with long axis 27, 271, and 272. Description will be made focusing on different points as compared with FIG. 1. Note herein that GD1 to GD4 correspond to claim 1, and GD5 corresponds to claim 1 to claim 4.

In FIG. 5 (GD1), the ultrasonic transducer 40 is provided in the liquid container 19 while placing a plane of vibration thereof sideways. The liquid for atomization Liq2 (Wa) is poured into the liquid container 19 from the nozzle of the liquid container 10 which stores the chemical-containing liquid Wa so that the liquid level is kept constant. Liq2 fills the plane of vibration.

The ultrasonic concave mirror lens 25 which is the ultrasonic convergence and reflection mechanism is provided on the left-hand side of the ultrasonic transducer 40 so as to be adjacent to each other, and it converges and reflects the ultrasonic waves to irradiate them obliquely upward left. The focal point Foc of the lens is set to around a point where Liq2 is pushed out by the ultrasonic waves. Liq2 (Wa) disperses obliquely upward left around Foc to discharge a large amount of mist.

The ultrasonic reflection tube 27 has a long axis and it is vertically provided. In the same figure, an example of a length of about 30 cm is shown. A lower part of the tube is coupled with a lid 191 of the container 19, and is provided so that the liquid for atomization Liq2 pushed out in the air by the above-mentioned ultrasonic waves may be surrounded. The air passage holes Air are provided in the lid, and it is constituted so that air can be sent into the lower part of the tube 27.

The ultrasonic reflection tube 27 advances the ultrasonic waves circumferentially scattered when Liq2 is atomized to the axial direction of the tube. The ultrasonic waves repeat the reflection inside the tube to reach the upper part thereof as indicated by an arrow of a solid line in the same figure.

The droplet liquid with a small diameter which has dispersed in the above-mentioned tube is atomized by the ultrasonic waves in the tube to increase the amount of mist. The mist is flown in the axial direction of the tube by the pressure of the ultrasonic waves to be discharged from the upper part thereof. A rising speed of the mist inside the tube is extremely high. The mist discharged from the tube goes up straightly by about 10 cm, and spreads around.

In the same figure, the droplet dispersed liquid with a large diameter collides with the inner wall on the left-hand side of the reflection tube to drop, and returns to the container 19.

An angle β between the direction of the ultrasonic waves reflected by the ultrasonic concave mirror lens 25 (HD of shown in a figure enclosed by a dashed line) and the axial direction of the reflection tube 27 (vertical) is set to such an extent that the droplet dispersed liquid AK2 does not jump out of the opening of the tube. What is necessary is just to shift slightly, since the tube has the long axis. When a length of the axis of the reflection tube is L, and a diameter of the tube is D, setting to an angle equal to or more than β that satisfies tan β=D/L is effective.

When the direction HD of the ultrasonic waves reflected by the ultrasonic concave mirror lens 25 is defined as a vertical direction as shown in FIG. 5 (GD2) the axis of the ultrasonic reflection tube 27 may be inclined so as to be the angle β or more.

While the generated mist can be discharged by the pressure of the ultrasonic waves which travel the inside of the tube in the present invention as described above, in order to further show this effect, experimentations are performed by lengthen the ultrasonic reflection tube.

FIG. 5 (GD3) is an example using the long axis ultrasonic reflection tube 271 with a diameter of about 1 cm and a length of about 100 cm. As compared with FIG. 5 (GD1), the mist discharge distances upper from the tip of the tube opening are both about 10 cm, but GD3 discharges the mist more highly than GD1 by the length of lengthen the tube. This shows the effect of the ultrasonic waves traveling the inside of the tube. Incidentally, if such a long axis reflection tube is used, the droplet dispersed liquid AK2 does not jump out of the tube even when the direction of the ultrasonic waves HD reflected by the ultrasonic concave mirror lens 25, and the axial direction of the reflection tube are directed to the same direction.

FIG. 5 (GD4) is an example using the long axis ultrasonic reflection tube 272 which can be curved. A tip thereof can be made thin to several millimeters. The chemical-containing mist can be discharged to a narrow place. It can be coupled with an endoscope or the like.

FIG. 5 (GD5) is improved in GD1 so that the small liquid container 20 can be mounted.

A portion to which the ultrasonic transducer is attached, and the container 19 provided with the ultrasonic concave mirror lens 25 can be integrally molded with plastics. The ultrasonic transducer is attached by a screw clamp or the like In the container 19, the water W is contained as the ultrasonic propagation medium Liq1.

The ultrasonic reflection tube 27 is provided in the lid 191 of the container 19. Additionally, a hole for inserting the nozzle of the liquid container 10, and the air passage holes Air are provided. The lid 191 and the ultrasonic reflection tube 27 can be integrally molded with plastics. Reference numeral 99 represents a fulcrum for attaching the lid 191 to the container 19. An integral construction of the lid 191 and the ultrasonic reflection tube 27 can be rotated to the counter clockwise around the fulcrum 99. Namely, the lid can be opened.

Where the lid 191 is opened, the small liquid container 20 provided the ultrasonic transparent film 23 at the bottom could be floated in Liq1. The liquid for atomization Wa is poured into the small liquid container 20 from the liquid container 10.

The mist which contains the chemical a is discharged from the tube by an operation of the ultrasonic transducer. As described above, since principal parts can be manufactured by integral molding, adjustment is unnecessary resulting in easy manufacturing.

All of the embodiments shown in FIG. 5 have high liquid atomization efficiency and excellent mist discharge characteristics as well, so that the air flow generating apparatus which has been required in the conventional mist generator can be eliminated. Additionally, since the chemical-containing liquid Wa in the liquid container 10 can be atomized while being used little by little, utilization efficiency of the chemical is high. Moreover, it can be constituted economically due to a small number of components. It can be utilized also as a portable mist generator since it is compact.

Next, characteristic effects caused by a combination of the ultrasonic convergence and reflection mechanism and the ultrasonic reflection tube of the present invention will be described in detail while comparing with the conventional example.

FIG. 6 (NG1) is a liquid atomization means using an ultrasonic cylindrical mirror lens 24 (cone horn type) disclosed in Japanese Unexamined Patent Publication (Kokai) No. 2003-38646, Publication of Unexamined Utility Model Application No. Sho. 58-8034, or the like. A case where the water W is atomized is shown. Since the ultrasonic waves are converged near the liquid level, a large amount of mist m and droplet liquid AK2 are generated. However, since the ultrasonic waves are diffused in the air above the liquid level, it cannot be said that the ultrasonic energy is fully utilized. Meanwhile, since particle diameter of the dispersed liquid is not uniform, and the dispersing direction is also wide, a mechanism for separating the droplet liquid and the mist, and an air flow generating apparatus 70 for carrying the mist are required.

FIG. 6 (GD6) is an embodiment of the present invention corresponding to claim 1, and it has a constitution in which the ultrasonic convergence and reflection mechanism is changed to the ultrasonic cylindrical mirror lens 24 in FIG. 5 (GD1). As compared with FIG. 6 (NG1), the long axis ultrasonic reflection tube 27 is provided in an upper part of the ultrasonic cylindrical mirror lens 24. FIG. 6 (GD6-A) is an external view showing an integral constitution of the ultrasonic cylindrical mirror lens 24 and the long axis ultrasonic reflection tube 27. Both are coupled with each other so that a predetermined interval may be provided and medial axes may be aligned.

In FIG. 6 (GD6), the lower part of the ultrasonic reflection tube 27 is set so as to surround the dispersing portion AK1C in the liquid AK1 pushed out by the ultrasonic waves and so as to introduce air to the inside of the tube from the bottom.

When constituted as described above, the ultrasonic waves scattered about near AK1C can be efficiently introduced into the reflection tube 27, thus having an effect on promotion of atomization, uniformization of the particle diameter of the mist, and carrying the mist. When the ultrasonic reflection tube with the length of 30 cm is used, the mist will be discharged from the tip to a height of about 10 cm. The mist can be taken outside and utilized, without using the air flow generating means.

FIG. 6 (NG2) is a result of experimenting in such a way that the lower part of the above-mentioned ultrasonic reflection tube 27 is sunk into the liquid for air not to enter from the lower part. The mist goes up from the liquid level up to a point of about 10 cm.

FIG. 6 (NG3) is a result of experimenting in such a way that, without using the ultrasonic convergence and reflection mechanism, the above-mentioned ultrasonic reflection tube 27 is provided in the same height as that shown in FIG. 6 (GD6) in a situation where the long liquid column AK1 is generated. As compared with GD6, the mist goes up to a height of only about 15 cm due to impacts on long distance Dc from the plane of vibration to the liquid dispersing portion AK1C, wide range of AK1C, or the like. The reason is that the ultrasonic waves scattered about near AK1C do not travel efficiently toward the upper part of the ultrasonic reflection tube 27. In order to discharge the mist from the tube, the air flow generating means 70 is indispensable.

It can be seen from the experimental results described above that atomizing the liquid locally and directionally by the ultrasonic convergence and reflection mechanism, providing the ultrasonic reflection tube so as to surround the portion where the liquid disperses and so as to take in air from the lower part of the tube, and making the ultrasonic waves travel in the axial direction of the tube have effects on improving atomization efficiency.

Figure 7:
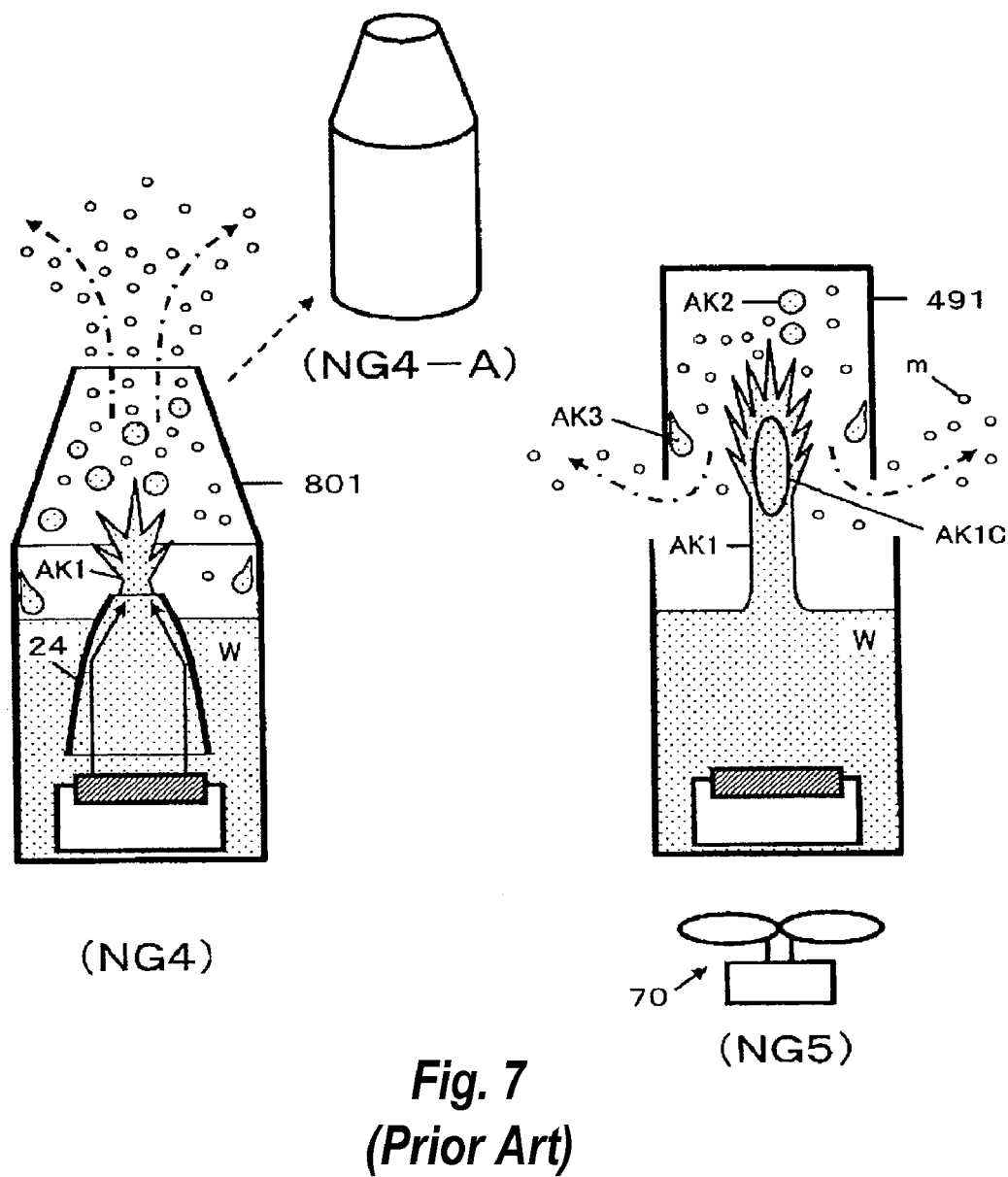

FIG. 7 is a configuration example of the liquid atomization means known well conventionally. A shape thereof is partially similar to that of the present invention. However, a mist discharge tube 801 shown in FIG. 7 (NG4) corresponds to a constitution in which the tube 27 is increased in diameter and decreased in length in FIG. 6 (NG2), and the mist discharge tube 801 acts as a guide for mainly discharging the mist in a predetermined direction.

Additionally, reference numeral 491 in FIG. 7 (NG5) represents a tube-shaped dispersing liquid preventive mechanism for dropping the dispersing droplet liquid and discharging the mist. Hence, in order to discharge the mist outside, the air flow generating means 70 is indispensable.

Both of the conventional examples of NG4 and NG5 do not have effects on remarkably increasing the amount of atomization, uniformizing the particle diameter of the mist, carrying the mist to distant locations, or the like, like the present invention. Hence, effects of the present invention are characteristic.

Third Embodiment

Figure 8:
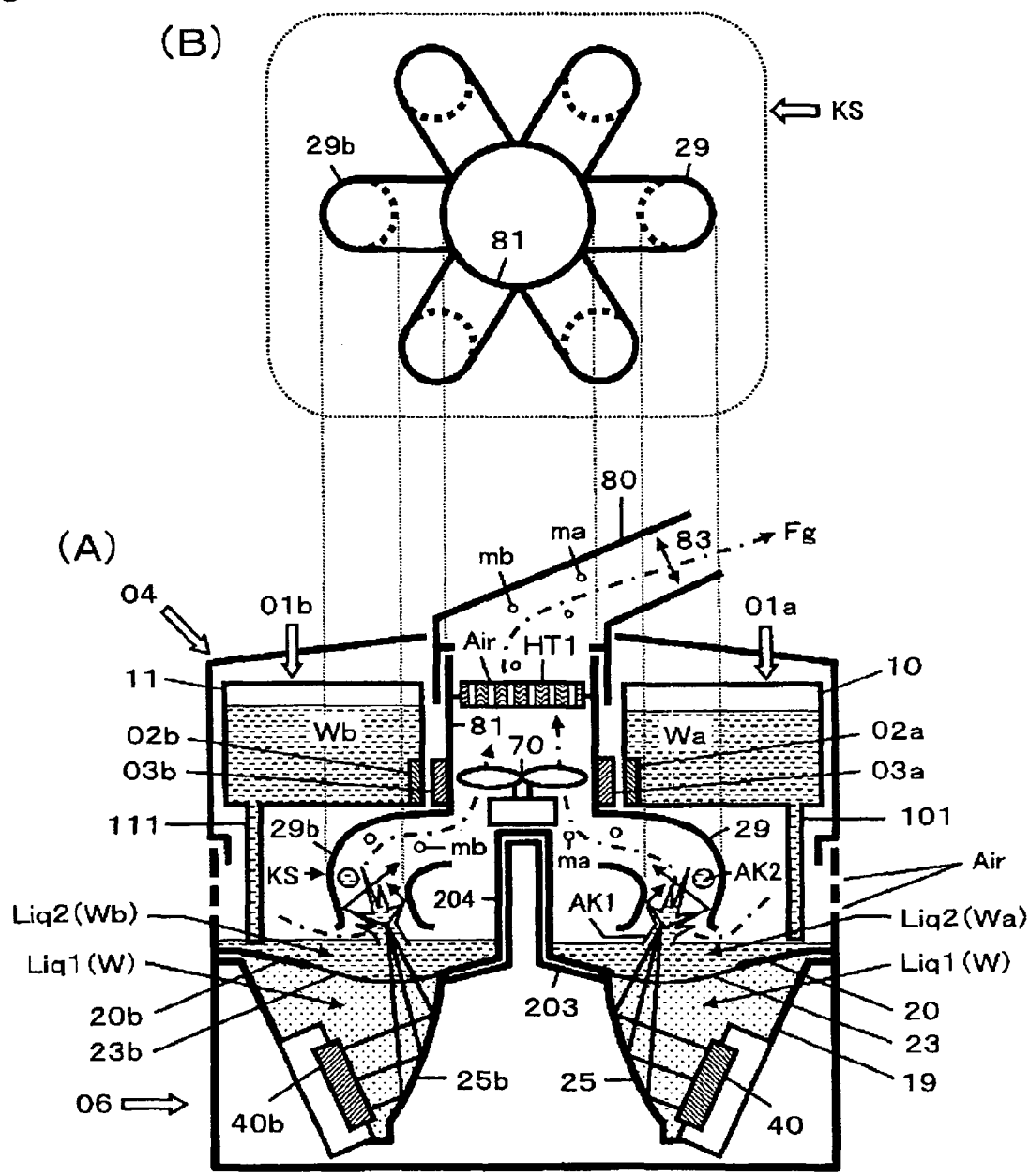
Figure 9:
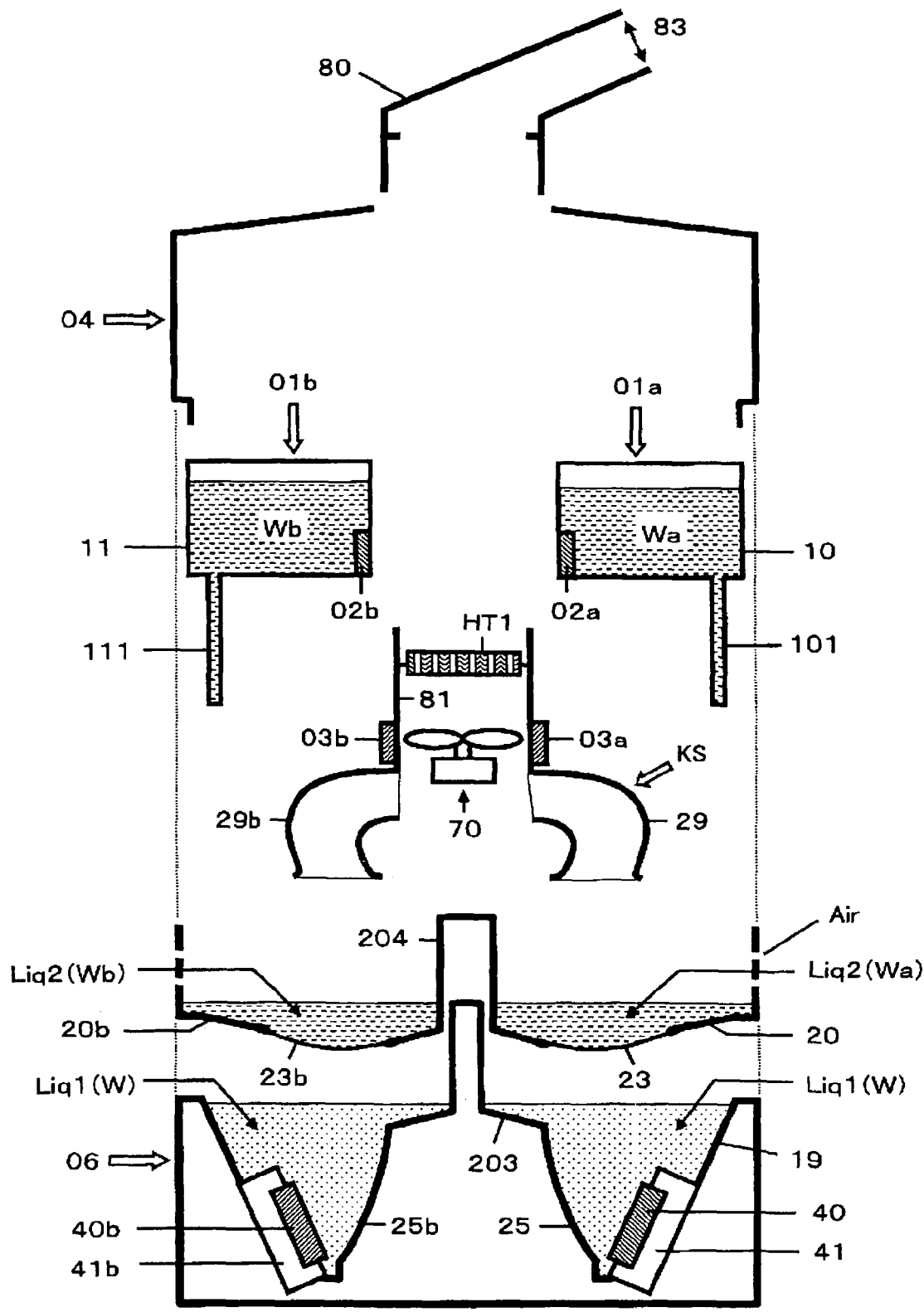

FIG. 8 is a third embodiment of the present invention, and shows a mist generator for atomizing the liquid which contains various chemicals (perfumes), and mixing the mist or vapor to be discharged. FIG. 8(A) is a figure in which a longitudinal section of the apparatus is viewed from the side, and FIG. 8(B) is a figure in which a mixer KS of the mist or vapor in which the ultrasonic reflection tubes 29, 29b and the air tube 81 are integrated in FIG. 8(A) is viewed from the top. The mixer KS can be integrally molded by plastics or the like. FIG. 9 is a view showing a component constitution in the embodiment.

Six means similar to the liquid atomization means 05 shown in FIG. 1 are circumferentially provided at the lower housing 06 in FIG. 8. Two of them are shown at right and left in FIG. 8(A). In the same figure, reference numerals 10 and 11 are the liquid containers for storing the perfume-containing liquids Wa and Wb in which the perfumes a and b are contained in that water, respectively. As for Wa and Wb, predetermined amounts are poured into the small liquid containers 20 and 20b through the nozzles 101 and 111, respectively.

FIG. 8(A) shows a situation in which Liq2 (Wa) is poured into the small liquid container 20, the perfume-containing mist ma is generated by ultrasonic irradiation, and the mist mb is similarly generated from the small liquid container 20b. The mists ma and mb are mixed within the air tube 81.

The air flow generating means 70 is provided inside the air tube 81, and an air current as indicated by the alternate long and short dash line Fg is generated to introduce the mist or vapor to the upper part thereof. The air flow generating means 70 rotates air blowing blades by a motor to generate the air current. Incidentally, although the photo coupler for detecting the amount of mist is omitted, it may be add thereto.

The heating means HT1 similar to that shown in FIG. 1 is provided in a path through which the above-mentioned mist passes as means for heating the mist or vapor. The air discharge tube 80 is provided in an upper part of the heating means HT1. The air discharge tube 80 is rotatable, and can direct the opening 83 in various directions.

Next, an operation thereof will be described. The above-mentioned liquid atomization means provided in six spots can perform on-off controls at high speed, respectively. Hence, it is possible to discharge six types of mists or vapors while switching them at high speed. Additionally, by intermittently driving six types of liquid atomization means and mixing the generated mist or vapor within the air tube 81, aromas can be discharged while being delicately mixed.

For example, in FIG. 8(A), when the ultrasonic transducers 40 and 40b are driven at a time rate of 1:2, the mist or vapor which contains the perfume a and the perfume b at a rate of 1:2 will be generated from the air discharge tube 80. Meanwhile, by changing a ratio of the driving power of the ultrasonic transducers 40 and 40b, the amount of generated mist is controlled, so that a desired mixing ratio may be achieved.

Next, a method for mixing the aroma based on a perfume recipe using the integrated memory circuits 02a and 02b provided in the liquid pouring means 01a and 01b in the same figure will be described. Features of the perfume-containing liquid Wa and Wb, namely, types of perfumes, concentrations, atomization conditions, precautions, or the like can be stored in the integrated memory circuits 02a and 02b.

An aroma recipe shall be obtained via the Internet or the like. Features of an aroma that the user desires, and perfume mixing information required to generate the aroma shall be associated with each other in the recipe in a form of a table or the like.

When a user inputs the aroma recipe into the control processing unit of the apparatus by means which is not shown in the same figure, the control processing unit will extract the type of perfume to be mixed, the mixing ratio, or the like, using the conversion table of the recipe.

Additionally, since the control processing unit can grasp what kind of liquids are poured into the six small liquid containers by reading the pieces of information in the above-mentioned integrated memory circuits, it can calculate the amount of atomization of each liquid so as to be the above-mentioned mixing ratio, and control the liquid atomization means so as to be the calculated value.

Next, a method for discharging the mist or vapor from the opening 83 in FIG. 8(A) will be described. There are a non-visual mode in which the mist is thoroughly evaporated and discharged in an invisible state, and a visual mode in which the mist is discharged in a mist state.

The non-visual mode can be achieved by increasing the heating value of HT1 and relatively reducing the air current in the air discharge tube 80. The atomized fine-particles are discharged from the opening 83 in a state of becoming too small to be seen after the evaporation proceeds with heat.

Two types of visual modes, one mode in which the mist is heavily discharges, and the other mode in which the mist is calmly raised such as smoke of an incense stick, are possible.

In order to setting to the former mode of heavily discharging the mist, what is necessary is just to send out the mist by the air flow generating means 70 without providing HT1.

Meanwhile, in order to raise the mist calmly vertically from the opening 83, following actions will be taken, namely, the air flow generating means 70 is not used, or a weak air current only enough for the mist to pass through the air holes Air of the heating means HT1 is generated by using the air flow generating means 70. A state where the mist is accumulated in the upper part of HT1 is formed. When HT1 is then driven, a circumambient air is warmed up, thus generating an ascending air current due to heat.

The mist rides on the ascending air current to come out of the opening 83, and it is straightly carried upward to be disappears soon. Fragrance floats therearound. If the opening 83 is narrowed, a behavior that the mist goes up changes such as smoke of an incense stick or an incense burner, and is visually interesting, thus providing the healing effects.

Next, as for a temperature control of the heating means HT1, it is preferable to set an air current temperature in the upper part of the heating means to a range of from 30 degrees Centigrade to 50 degrees Centigrade. The reason is that the perfume is appropriately evaporated, and the mist is raised beautifully visually, and it will be hereinbelow described in an embodiment shown in FIG. 22 in detail.

Next, maintenance of the present embodiment will be described. In disassembly, when the air discharge tube 80 and the upper housing 04 are removed, the liquid pouring means 01a and 01b are removed, and a mechanism in which the mixer KS and the air flow generating means 70 are integrated is removed as shown in FIG. 9, all the portions that tend to be dirty can be cleaned.

Further, the small liquid containers 20 and 20b can be removed and cleaned. Each of reference numerals 203 and 204 represents a part of mechanisms for mounting the small liquid container detachably and attachably. When there are liquids Wa and Wb left unspent, they are not clean, but since they can be removed easily, the small liquid containers can always be kept clean. Note herein that the ultrasonic propagation medium Liq1 (W) can be exchanged if needed, although not contaminated.

Fourth Embodiment

FIG. 10 is a fourth embodiment of the present invention, and shows a mist generator for atomizing or evaporating a liquid arbitrarily selected among a plurality of liquids which contain chemicals (perfumes) to discharge the mist. FIG. 10(A) is a figure in which a longitudinal section (cross section at a dashed line Sec1 in FIG. 10(B)) of the apparatus is viewed from the side. FIG. 10(B) is a figure in which a transverse section at a dashed line Sec2 in FIG. 10(A) is viewed from the top.

FIG. 10(B) shows a state where only the small liquid containers 20 and 20b are mounted in an atomization zone divided into six. The liquids for atomization Liq2 (Wa) and Liq2 (Wb) are poured into the small liquid containers 20 and 20b by the liquid pouring means 01a and 01b, respectively. Reference numerals 101 and 111 are liquid pouring nozzles. Since the ultrasonic transducer 40, and the ultrasonic transparent films 23, and 23b are in the lower housing 06, they are indicated by dashed lines in FIG. 10(B). Naturally, the small liquid container can be provided also in the four remaining zones.

Reference numerals 29 and 29b are ultrasonic reflection tubes provided over the liquids in the small liquid containers 20 and 20b in FIG. 10(A), respectively, and they are made by boring through light metals, or plastic molding. Oblique lines indicate material parts. Reference numeral 291 represents a mechanism for holding the ultrasonic reflection tube 29 at a predetermined height from the liquid level of the small liquid container 20.

Features of the present embodiment are that the ultrasonic transducer 40 is one in number as shown in FIG. 10(A), and it is attached to a tip of a supporting bar 90 and rotates around an axis of rotation 91. The plane of vibration 40F can be moved so as to face to the ultrasonic concave mirror lenses 25, 25b, 25c, 25d, 25e, and 25f provided in six zones.

In FIG. 10(A), the plane of vibration 40F faces to the ultrasonic concave mirror lens 25, and the liquid Liq2 (Wa) is atomized. The ultrasonic reflection tube 29 is provided over AK1 around which the liquid is pushed out to disperse. While the ultrasonic reflection tube 29 is a cylinder, it has a shape which is bent from the middle, and a tip thereof reaches near the heating means HT1. The ultrasonic waves repeat reflection inside the tube to atomize the droplet dispersed liquid AK2. The generated mist is flown by the ultrasonic waves which travel inside the tube to an axial direction to go up near the HT1.

When a circumambient air is warmed by the heating means HT1 here, an ascending air current due to heat is generated, and the mist ma or vapor goes up as indicated by the alternate long and short dash line Fg to finally be discharged from the opening 83.

Although the air flow generating means is not used in the same figure, the same means may be used when the air current is weak or when users desire to discharge the mist in the far distance. The air discharge tube 80 can be rotated, and the opening 83 can be directed in various directions.

Next, when the axis of rotation 91 is turned, the ultrasonic transducer 40 will rotate around of the above-mentioned plurality of ultrasonic concave mirror lenses to atomize an arbitrary liquid among six types of liquids Liq2. Additionally, the heating means HT1 also rotates simultaneously over the ultrasonic reflection tube where the mist passes. Hence, it is possible to sequentially switch the mist or vapor which contains six types of perfumes to be discharged.

For example, when the ultrasonic transducer 40 is rotated by 180 degrees from a state shown in FIG. 10(A), Liq2 (Wb) will be atomized. Switching of the aroma is extremely clear. Moreover, when they are switched one after another in a short time, the aroma will be mixed in space, allowing varied aroma space to be produced.

Fifth Example

Figure 11:
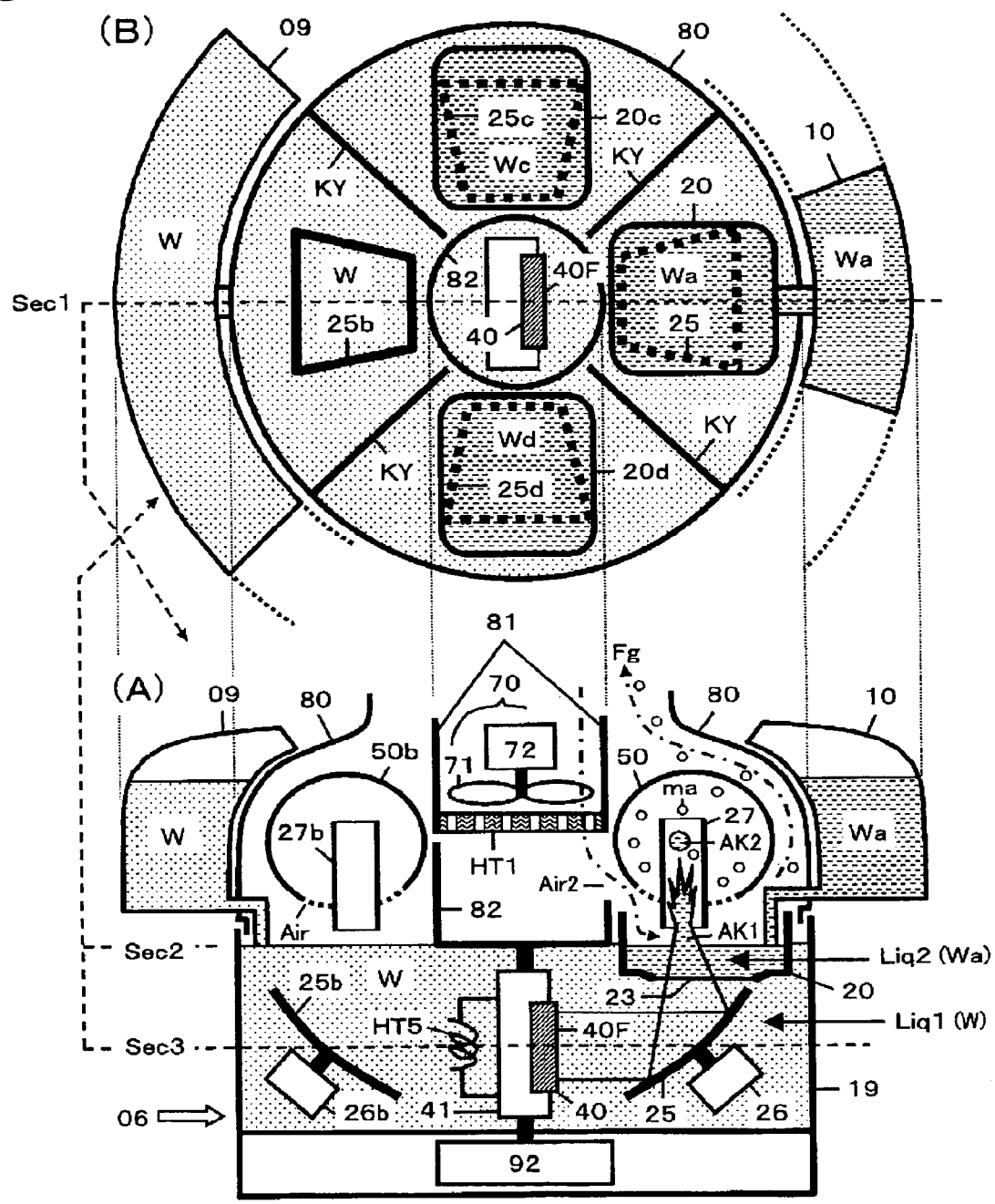

FIG. 11 is a fifth embodiment of the present invention, and shows a mist generator which can irradiate an arbitrary perfume-containing liquid with the ultrasonic waves to discharge the mist or vapor which contains various perfumes. FIG. 11(A) is a figure in which a longitudinal section (cross section at the dashed line Sec1 in FIG. 11(B)) of the apparatus is viewed from the side. FIG. 11(B) is a figure in which transverse sections near two dashed lines Sec2 and Sec3 in FIG. 11(A) are viewed in piles from the top.

The ultrasonic transducer 40 is arranged so that the ultrasonic waves may be transversely generated in FIG. 11(A). The ultrasonic transducer 40 can be rotated 360 degrees by a rotation angle controlling motor 92.

The four ultrasonic concave mirror lenses 25, 25b, 25c, and 25d are obliquely provided around the ultrasonic transducer 40. Each of the ultrasonic concave mirror lenses can adjust an angle of reflection by an angle adjustment mechanism. Only two angle adjustment mechanisms 26 and 26b are shown in FIG. 11(A).

In FIG. 11(B), the small liquid containers 20, 20c, and 20d provided with the ultrasonic transparent film 23 at the bottom are provided on the ultrasonic concave mirror lenses 25, 25c and 25d, respectively. While these small liquid containers are attachable and detachable, the mounting mechanism will be hereinbelow described in detail.

The perfume-containing liquids Wa, Wc, and Wd which differ in type are stored in the small liquid containers 20, 20c, and 20d as the liquid for atomization Liq2, respectively. The bottom of each small liquid container has a hollow, and the ultrasonic transparent film 23 is provided in the hollow portion. Hence, it is constituted that Liq2 gathers on the ultrasonic transparent film when Liq2 in the small liquid container decreases.

Reference numeral 10 represents the liquid container for supplying Wa to the small liquid container 20, and reference numeral 09 represents the liquid container for supplying the water W to the container 19.

In FIG. 11(A), reference numerals 50 and 50*b* are the dispersed liquid collecting mechanisms. The mechanism is constituted by a ball-shaped hollow container, and the ultrasonic reflection tubes 27 and 27*b* are connected to a lower part of the container. The air passage holes Air are provided in the surroundings of a connecting section between the hollow container and the ultrasonic reflection tube. The dispersed liquid collecting mechanism is held by a mechanism which is not shown in the same figure.

Reference numeral 70 represents the air flow generating means, reference numeral 71 represents the air blowing blades, and reference numeral 72 represents the motor. Reference numeral 81 represents the air tube for taking in air from the outside, and the air flow generating means 70 is attached to the air tube 81 by a mechanism which is not shown in the same figure. Additionally, the air tube 81 is fixed to the mist discharge tube 80 by a mechanism which is not shown in the same figure.

Reference numeral 82 represents an air tube with a cave hole Air2 for passing rightward air entered from the air tube 81. The air tube 82 is connected to the axis of rotation of the ultrasonic transducer 40, and when the ultrasonic transducer 40 rotates, it will rotate together. Symbol KY shown in FIG. 11(B) represents a division plate for dividing the mist discharge tube 80 into four portions, and air exited from the above-mentioned cave hole Air2 passes through the divided portion.

An atomizing operation will be described. In FIG. 11(A), the ultrasonic waves generated in the ultrasonic transducer 40 travels rightward, changes the direction upward and is also converged by the ultrasonic concave mirror lens 25, and passed through the ultrasonic transparent film 23 to finally reach Liq2 (Wa).

Liq2 disperses by the ultrasonic waves to generate a large amount of perfume-containing mist ma. The droplet dispersed liquids AK2 are collected by the dispersed liquid collecting mechanism 50 to be returned to the small liquid container 20.

Here, it is preferable to adjust the angle of the concave mirror lens 25 so that the ultrasonic waves may be converged near the liquid column AK1. The angle adjustment mechanism 26 is a mechanism for performing this adjustment.

The perfume-containing mist ma is discharged outside through a path indicated by the alternate long and short dash line Fg. The air flow generating means 70 operates so as to promote the discharge of the mist. Air taken in from the air tube 81 flows downward by the air flow generating means 70, enters the mist discharge tube divided by the division plate KY through the cave hole Air2, and carries the mist ma along the path of Fg.

When the ultrasonic transducer 40 is rotated by 90 degrees in a counter clockwise direction from a state shown in FIG. 11, the perfume-containing liquid Wc is atomized (refer to FIG. 11(B)). In a state where it is further rotated by 90 degrees in the counter clockwise direction, namely, in a state where the plane of vibration 40F faces to the left in FIG. 11(A) Liq1 (water W) in the container 19 is atomized.

In FIG. 11(A), when the temperature of Liq2 (Wa) is low, Liq1 (W) may be warmed up by an electric heater HT5 to conduct the heat to Liq2 (Wa) in the small liquid container 20. When Wa is set to an appropriate temperature to atomize it, a large amount of mist will be generated, and smell characteristics will also be improved. A temperature of 30 to 50 degrees Centigrade is suitable for the temperature of perfume-containing liquid Liq2.

In order to further increase transmission speed of heat, the ultrasonic concave mirror lens 25 is changed downward by the angle adjustment mechanism 26, so that the liquid Liq1 in the container 19 can be stirred by the ultrasonic waves. Heat is conducted from Liq1 to Liq2 to be warmed.

Figure 12:
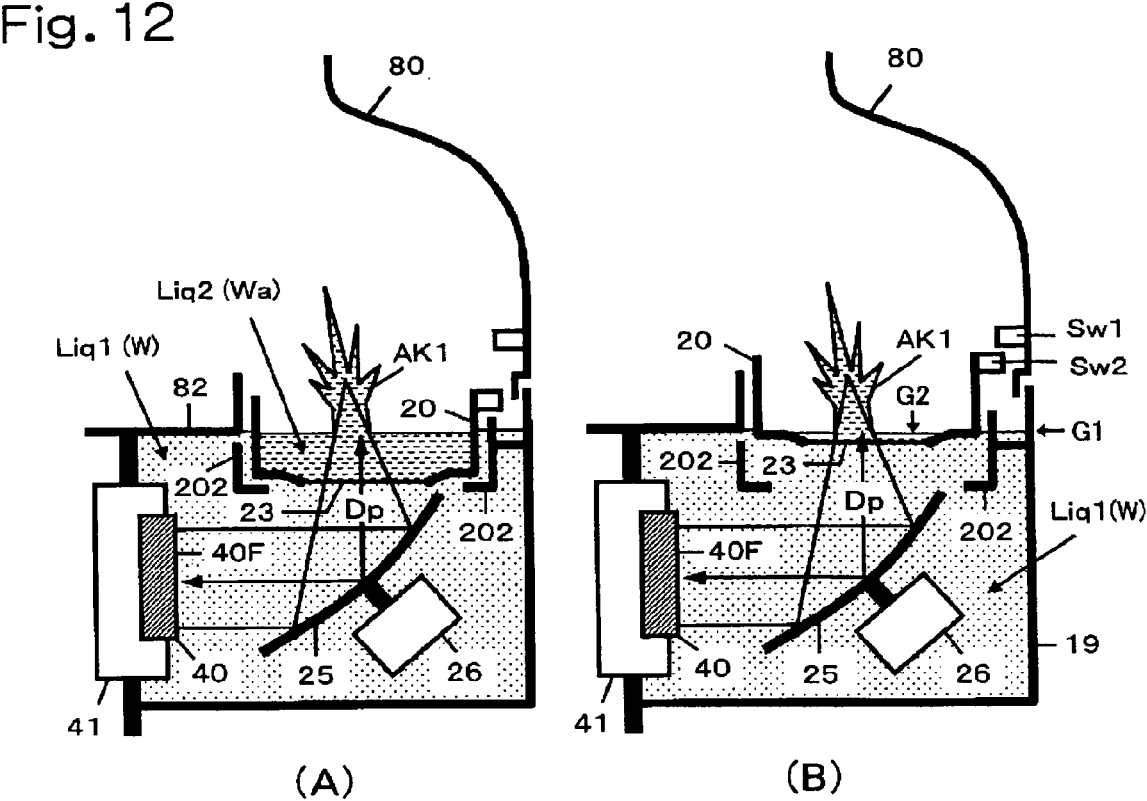

FIG. 12 shows a method of floating and using the small liquid container 20 on Liq1 (W), and its effects in the embodiment shown in FIG. 11.

In FIG. 12, reference numeral 202 represents a tube-type mounting mechanism in which a bottom thereof is partially bored, and the small liquid container 20 is mounted in the tube movably upward and downward. The small liquid container 20 is in Liq1 (W) while floating. Here, it is supposed that a volume of Liq1 is large, and the liquid level of the Liq1 is not changed largely even when the small liquid container 20 moves up and down.

FIG. 12(A) shows a case where Liq2 (Wa) sufficiently exists in the small liquid container 20, wherein a distance from the plane of vibration 40F to the liquid level of Liq2 is Dp. Dp is set to a distance where Liq2 is efficiently atomized.

As atomization proceeds, Liq2 will be consumed to be gradually decreased. This state is shown in FIG. 12(B). Since the small liquid container 20 becomes lighter, it rises by buoyancy.

When Liq1 is water or oil, and Liq2 is perfume-containing water or the like, specific gravities of Liq1 and Liq2 are close. Hence, a reduction in weight due to the consumption of Liq2 and a reduction in buoyancy are almost balanced, resulting in a small change in the liquid level of Liq2. Namely, by comparing FIG. 12(A) with FIG. 12(B), since the change of Dp is small, atomization is stabilized regardless of the amount of Liq2 (Wa). Even when the amount of Liq2 is reduced, it is atomized normally.

Sw1 and Sw2 in the same figure are point of contacts of switches. When the small liquid container 20 rises and Sw1 and Sw2 are brought into contact with each other in FIG. 12(B), it is determined that Liq2 became empty, so that atomization can be stopped. Alternatively, it is possible to control so that the liquid Liq2 may be newly poured thereinto.

In the same figure, a photo coupler, a magnetic sensor, or the like may also be substituted for Sw1 and Sw2. In this case, since a rising amount of the small liquid container 20 can be measured more accurately, the consumption amount of Liq2 can be grasped.

Controls to change an atomization speed, to automatically supply Liq2, or the like according to the change of the consumption amount are possible.

Sixth Example

FIG. 13 is a sixth embodiment of the present invention, and shows a mist generator for atomizing or evaporating various chemical-containing liquids to discharge them to distant locations while switching at high speed. FIG. 13(A) is a figure in which a longitudinal section of the apparatus is viewed from the side. FIG. 13(B) is an external view of the small liquid container 20. Characteristic portions will be described as compared with the aforementioned embodiment.

In FIG. 13(A), the ultrasonic transducer 40 is in the ultrasonic propagation medium Liq1 (water W), and the plane of vibration 40F thereof faces obliquely upward. The plane of vibration 40 is rotated 360 degrees by the rotation angle controlling motor 92. Reference numeral 91 represents the axis of rotation.

The liquid for atomization Liq2 (Wa) which contains the perfume a is contained in the small liquid container 20. A side wall of the container forms the ultrasonic concave mirror lens 25, and the ultrasonic transparent film 23 is provided at the bottom. The ultrasonic transparent film 23 is slightly obliquely attached thereto so that the liquid may gather near the concave mirror lens 25 as the liquid Liq2 decreases.

The above-mentioned Wa is poured into the small liquid container 20 by the pouring means which is not shown in the same figure. Similarly, the perfume-containing liquid Wb is poured into the small liquid container 20b.

Reference numeral 251 represents a hood continuing from the reflecting plate 25, and is a liquid reflecting plate for collecting the droplet dispersed liquids AK2 to the small liquid container 20. Reference numeral 201 represents a part of the small liquid container 20, and acts so as to make the dispersed liquid AK2 collide and to collect it in the small liquid container 20. As described above, the small liquid container 20 is constituted by integrating the ultrasonic transparent film 23, the ultrasonic concave mirror lens 25, and the dispersed liquid collecting mechanisms 251 and 201 (refer to external view (B)).

The small liquid container 20 is mounted in the liquid container 19 so that the ultrasonic transparent film 23 may contact with Liq1. The tube type mounting mechanism 202 is a supporting mechanism for mounting the small liquid container 20, and it is provided so as to surround the small liquid container 20. When the small liquid container 20 is lifted, it is detached from the tube type mounting mechanism 202, and it has flexibility capable of moving up and down in the tube type mounting mechanism 202. Hence, the small liquid container 20 can be floated on Liq1. It is a similar principle to that in FIG. 12.

Although two small liquid containers are shown on the right and left sides in FIG. 13(A), a lot of small liquid containers may be provided around the ultrasonic transducer 40.

Since the plane of vibration 40F is attached so as to face obliquely upward in the present embodiment, an ultrasonic propagation path from 40F to the liquid level of Liq2 is short, resulting in high atomization efficiency. Additionally, since the ultrasonic transparent film 23 and the ultrasonic concave mirror lens 25 are integrated in the small liquid container 20 as described above, the liquid atomization means can be constituted in small size. In order to incorporate in the tube of the air gun, it is indispensable that the liquid atomization means is small in size, and it satisfies this condition.

A mist discharge operation will be described. The ultrasonic waves pass through Liq1 (W), propagates to Liq2 (Wa) through the ultrasonic transparent film 23, and is converged and reflected by the ultrasonic concave mirror lens 25. The liquid disperses near the focal point Foc of the ultrasonic concave mirror lens 25, and a large amount of perfume-containing mist ma and droplet dispersed liquid AK2 are generated.

Although the atomization is promoted by the ultrasonic reflection tube 27, the mist ma and droplet liquid AK2 2 are discharged from the tip of the tube since the tube is short. AK2 collides with the dispersed liquid collecting mechanisms 251 and 201 to drop, and returns on the ultrasonic transparent film 23. The mist flows out of a clearance between the dispersed liquid collecting mechanisms 251 and 201, and is accumulated in the mist discharge tube 80.

The mist concentration is detected by the photo coupler which is composed of the LED 47 and the photo transistor 48. Symbol bm is a light beam emitted from the LED 47.

When the air pressure of the tube is instantaneously increased by the instant air flow generating means 74 (air gun) at a point when the mist concentration of the mist discharge tube 80 becomes suitable, an air current is generated along the path indicated by the alternate long and short dash line Fg, and the mist ma accumulated in the mist discharge tube 80 becomes the annular mist Lm to then fly from the opening 83. It is possible to selectively create aroma space even in distant locations.

The upper part of the mist discharge tube 80 is crane neck shape, and the vicinity the opening 83 has a shape similar to that shown in FIG. 1. The mist discharge tube 80 is rotatable on the lower housing 06. Hence, the annular mist Lm can be discharged in various directions.

The tube near the opening 83 may be composed of materials such as fragrant woods, which circumferentially discharge aroma molecules. In this case, the aroma molecules can be discharged near the opening wile being mixed to the mist.

A flight distance of Lm changes by changing a moving speed and a moving distance of the turbinated film 75 of the instant air flow generating means 74. It is also possible to provide time and speed fluctuation to the discharge of the annular mist Lm.

Thereby, a situation where the mist locally floats can be formed in a room. When people see a behavior of the mist which changes every moment, their minds will be healed.

Moreover, since the type of perfume-containing mist can be switched at high speed, a different aroma can be discharged for every direction. Visual fun that the annular mist changes and the change in aroma are combined to be able to produce attractive space.

The electric heater HT5 for heating Liq1 is provided in the liquid container 19. HT5 is used for setting Liq2 to be an appropriate temperature and promoting the evaporation. Since it is similar to that of the above-mentioned embodiment, its detail description will be omitted.

Next, a constitution for further increasing the healing effects will be described. The acoustic sensor Sb for detecting the sound of water drops, the mist discharge tube 80, and the means 85 for illuminating the mist to be discharged are provided in the center portion where the plurality of small liquid containers gather. Since the method for presenting the sensory stimulation has been described in the embodiment of FIG. 1, it is omitted here.

The means 85 can change the color of illumination and intensity according to the type of perfume-containing mist and concentration. When the mist discharge tube 80 is constituted by transparent glasses or the like, light will be scattered due to the mist, so that the whole mist discharge room seems to be beautifully shining. In addition, the annular mist Lm is also beautifully presented.

The means 85 may also be composed of an incandescent lamp, a tungsten halogen lamp, or the like. In this case, evaporation of the mist is promoted with the heat of the electric lamp. It is possible to achieve the apparatus with excellent smell characteristics.

Seventh Embodiment

Figure 14:
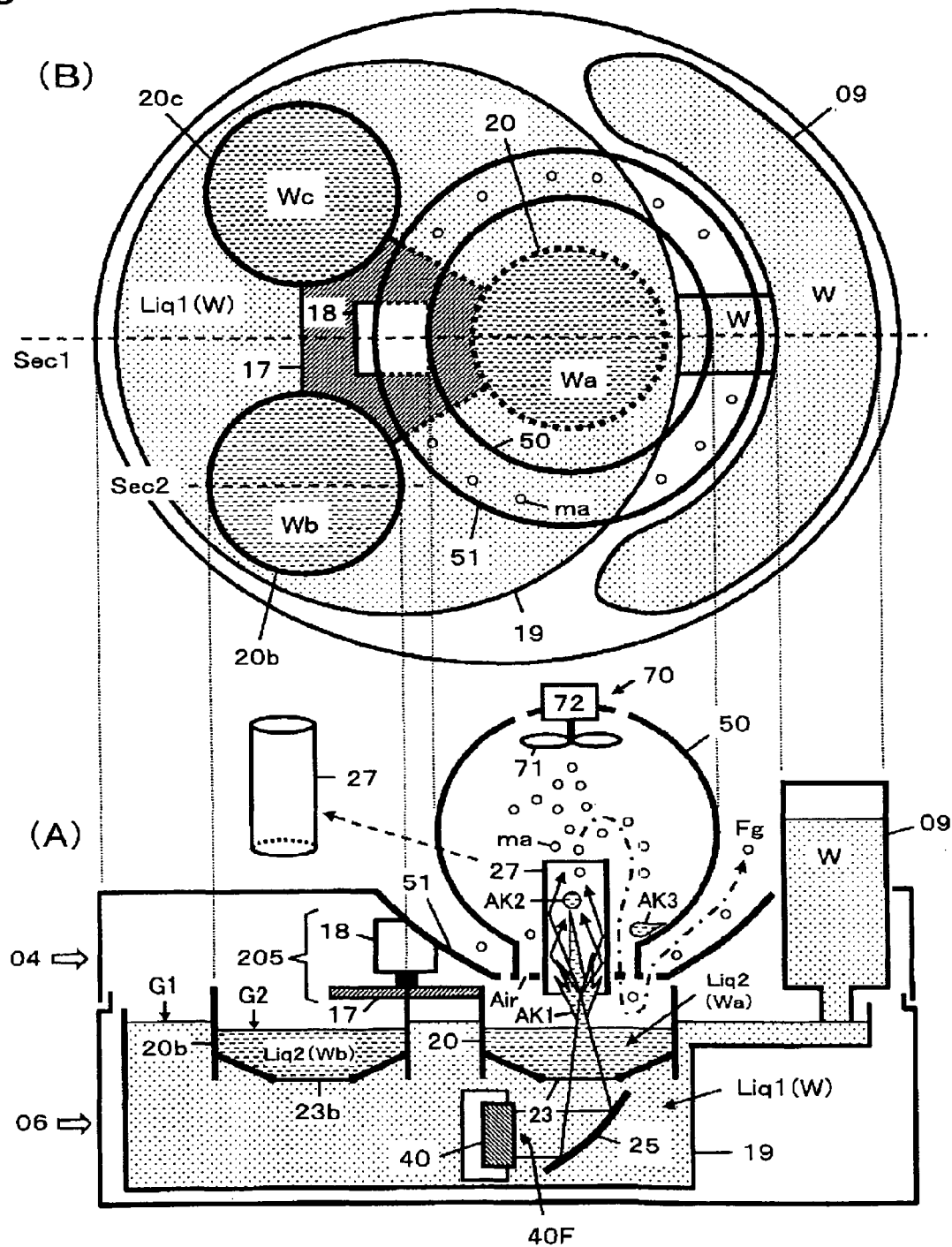

FIG. 14 is a seventh embodiment of the present invention, and shows a mist generator for discharging the mist or vapor in which various chemicals are contained while exchanging the small liquid containers. FIG. 14(A) is a figure in which longitudinal sections (cross sections at dashed lines Sec1 and Sec2 in FIG. 14(B)) of the apparatus are viewed from the side. FIG. 14(B) is a top view wherein the upper housing 04 is removed in FIG. 14(A).

Three small liquid containers 20, 20b, and 20c are provided in the liquid container 19 containing Liq1 so as to be coupled with each other. Reference numeral 205 represents a mechanism for exchanging the small liquid container, and it is composed of a mechanism 17 for coupling the small liquid container, and a mechanism section 18 for rotating the mechanism 17.

Each small liquid container is circular and has a hollow portion at the bottom, and the ultrasonic transparent film 23 is provided in the hollow portion. The containers float on Liq1 and can move up and down. Namely, the above-mentioned coupling mechanism 17 permits a vertical flexibility of each small liquid container, and horizontally couples the container with each other. Symbol G1 is a liquid level position of Liq1 and G2 is a liquid level position of the liquid for atomization Liq2. Since three small liquid containers are floating, the liquid level position G2 of Wa, Wb, and Wc is almost the same.

When the coupling mechanism 17 rotates by the mechanism section 18, each small liquid container will move on the liquid level of Liq1, and will come on the ultrasonic concave mirror lens 25 sequentially.

The ultrasonic waves are reflected by the ultrasonic concave mirror lens 25 to thereby converge in the upper part. The liquid Liq2 (Wa) is pushed out and locally dispersed. The ultrasonic reflection tube 27 is provided so as to surround the dispersing portion. A large amount of mist ma and droplet dispersed liquid AK2 are discharged from the upper part of the tube.

The mechanism 50 for collecting the dispersed liquids AK2 is provided on the ultrasonic reflection tube 27. The mechanism 50 is a globular hollow container and the air passage holes Air are provided in a lower portion indicated by dashed line. The droplet dispersed liquid AK2 drops from the air passage holes Air in the small liquid container 20 along an inner wall of the hollow container to be finally collected. AK3 is a droplet liquid which drops along the wall.

The air flow generating means 70 is provided at an upper part inside the mechanism 50, and it drives so that a downward weak air current may be generated. The above-mentioned generated mist ma passes through the above-mentioned air holes Air along the path indicated by the alternate long and short dash line Fg, and is discharged outside by the downward air current.

The vicinity of the above-mentioned air passage holes Air is connected to a wing-shaped mist guide mechanism lower part 51. The perfume-containing mist is diffused circumferentially to emit fragrance by the mist guide mechanism.

Next, when the liquid to be atomized is switched, the coupling mechanism 17 is rotated in FIG. 14(B). For example, since the small liquid container 20b may move onto the concave mirror lens 25 when the coupling mechanism 17 is rotated in a counter clockwise direction, the perfume-containing liquid Wb is atomized.

Moreover, when an amount of rotation of the coupling mechanism 17 is adjusted and any small liquid container is kept from being located onto the upper part of the concave mirror lens 25, the liquid for atomization will become the water W and a water mist will be generated. The water W is supplied from the water container 09 to the liquid container 19.

Eighth Embodiment

Figure 15:
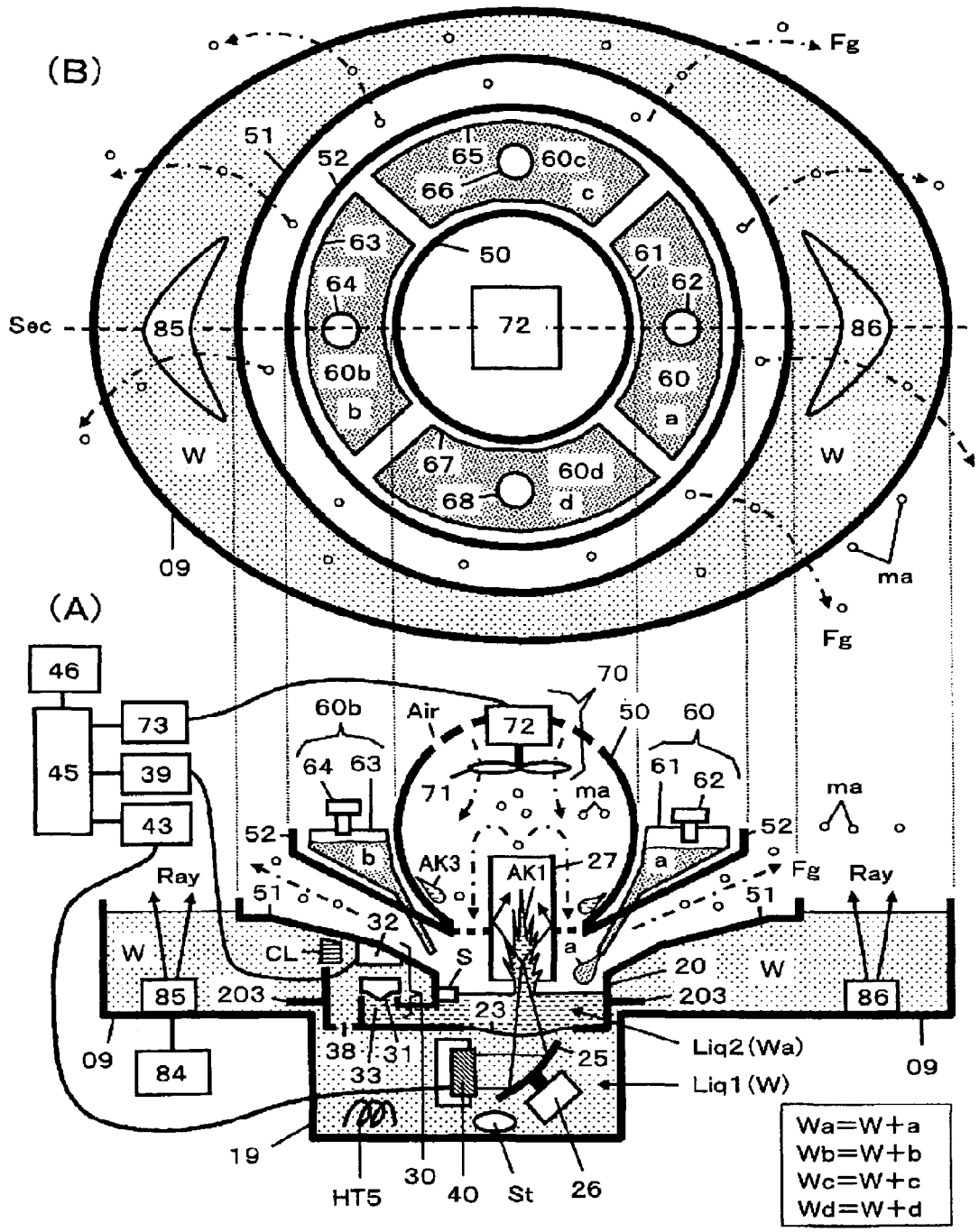

FIG. 15 is an eighth embodiment of the present invention, and shows a mist generator for discharging the mist or vapor which contains various aromas while controlling the types of chemicals (perfumes) to be poured into the small liquid container 20. FIG. 15(B) is a top view. FIG. 15(A) is a figure in which a longitudinal section at the dashed line Sec in FIG. 15(B) is viewed from the side.

In FIG. 15(A), reference numeral 09 represents a liquid container for storing a large amount of water W. This water W passes a clean filter CL to then be supplied into the liquid container 19 from a liquid passage hole 38. This water W is the ultrasonic propagation medium Liq1. The ultrasonic transducer 40 is provided in the liquid container 19 while placing a plane of vibration thereof sideways.

A temperature sensor St is provided near the ultrasonic transducer 40. The temperature sensor measures a temperature rise of Liq1 (W). The temperature data is processed by the control processing unit 45, and when the temperature rise is excessive, it can control a drive circuit 43 to suppress the drive of the ultrasonic transducer 40.

The ultrasonic concave mirror lens 25 is provided on the right-hand side of the ultrasonic transducer 40, and the small liquid container 20 which provided with the ultrasonic transparent film 23 at the bottom is provided in an upper part of the ultrasonic concave mirror lens 25. The vicinity of the small liquid container 20 is connected with the wing-shaped mist guide mechanism lower part 51.

A liquid passage control mechanism 30 for pouring the water W of the liquid container 09 into the small liquid container 20 is provided between the liquid container 09 and the small liquid container 20. The liquid passage control mechanism 30 is composed of a liquid passage hole 33, a liquid stop valve portion 31, and an electromagnet 32 for lifting the liquid stop valve portion. Reference numeral 39 represents a drive circuit of the electromagnet 32, and reference numeral 46 represents a user operating unit for a user to select switching of the perfume-containing mist or the like.

The ultrasonic reflection tube 27, the dispersed liquid collecting mechanism 50, and the air flow generating means 70 are provided in an upper part of the small liquid container 20. Reference numeral 73 represents an air flow generation driving device. A lower part of the dispersed liquid collecting mechanism 50 is connected to a wing-shaped mist guide mechanism upper part 52. The generated mist or vapor passes through between the mist guide mechanism lower parts 51 and 52 to then diffuse circumferentially. Since the constitution is similar to that in FIG. 14, description of operation is omitted.

Means 60 and 60b for pouring the perfumes into the small liquid container 20 are provided on the mist guide mechanism 52 shown in FIG. 15(A). In FIG. 15(B), similar four perfume pouring means (60, 60b, 60c, and 60d) are provided around the globular hollow container 50. Each perfume pouring means is composed of pumps 62, 64, 66, and 68 for pouring the perfume liquids a, b, c, and d in the perfume containers 61, 63, 65, and 67, and the perfume liquids in this perfume container into the small liquid containers 20 little by little.

A nozzle point of the perfume container 61 reaches the upper part of the small liquid container 20 through a hole provided in the above-mentioned mist guide mechanism upper part 52.

The above-mentioned perfume pouring pump is driven and controlled by the control processing unit 45. Additionally, it can also be moved manually.

The small liquid container 20 and the dispersed liquid collecting mechanism 50 are integrated by a fitting mechanism which is not shown in the same figure. Reference numeral 203 represents a mechanism for attaching and detaching the small liquid container 20. Structures above the mechanism 203 are detached when they are lifted.

Next, a method for pouring the perfume-containing liquid into the small liquid container 20 will be described. First, when the electromagnet 32 is driven by drive circuit 39 and the liquid stop valve portion 31 is pulled up in a direction of the electromagnet 32, the water W in the liquid container 09 passes through the clean filter CL, and is poured into the small liquid container 20 from the liquid passage hole 33. Symbol S is a liquid level detection sensor.

When the control processing unit 45 controls the drive circuit 39 to thereby stop energization to the electromagnet 32 at a point where the water level poured into the small liquid container 20 became S, the liquid stop valve portion 31 will move downward by gravity to then close the liquid passage hole 33. The water level of the small liquid container 20 stops at the position of S. A sensor which reacts in a plurality of depths may be sufficient as S.

As described above, the liquid passage control mechanism 30 operates so that only a predetermined amount of liquid in the liquid container 09 may be poured in the small liquid container 20, and has characteristics capable of closing the liquid passage after that.

Meanwhile, the control processing unit 45 and the drive circuit 39 do not replenish the next liquid until the liquid poured into the small liquid container 20 is consumed by a predetermined amount, and operate so that the next liquid may be poured into the small liquid container 20 after the predetermined amount of liquid in the small liquid container 20 is consumed.

Moreover, the liquid for atomization Liq2 can also be mixed within the small liquid container 20 by using a, b, c, and d as basic perfumes. The perfume-containing liquid for generating various aromas can be generated.

The atomizing operation is similar to that of the case shown in FIG. 14. Since separation of the dispersed liquid and the mist is performed by using the air flow generating means 70 in a narrow space, the apparatus can be constituted in small size. In particular, the apparatus can be reduced in height.

The mist discharged between the mist guide mechanisms 51 and 52 floats on a water surface of the liquid container 09. Here, a mist concentration sensor which is not shown in the same figure may be provided in the dispersed liquid collecting mechanism 50, and the air current may be instantaneously generated by the air flow generating means 70 at a point where the concentration thereof becomes a predetermined value or more. It is possible to produce so that the mist may run on the water surface of the liquid container 09.

The means 85 and 86 are illumination means, such as LEDs or the like, and the means 84 is illumination control means. Color and intensity are adjusted and light is discharged according to the concentration of the mist discharged and the type of contained perfume. Since the mist is illuminated from the bottom, it is fantastic. Particularly, irradiation of the light of the color corresponding to the smell impression of the perfume will provide the healing effects.

Although Liq2 (Wa) in the small liquid container 20 is consumed by atomization, the perfume concentration of Liq2 is kept constant since the liquid passage hole 33 is closed in the meantime. Hence, the intensity of the aroma discharged can be kept constant, without being thinned.

Since the mist stops being generated when the small liquid container 20 becomes empty, it is detectable by the above-mentioned mist concentration sensor that the small liquid container 20 became empty. Alternatively, the liquid amount detecting sensor which is not shown in the same figure may be provided near the bottom of the small liquid container 20, and it may detect that Liq2 became a small amount. The control processing unit 45 can be controlled so that another perfume-containing liquid may be poured at a point where Liq2 became the predetermined amount or less.

Figure 16:
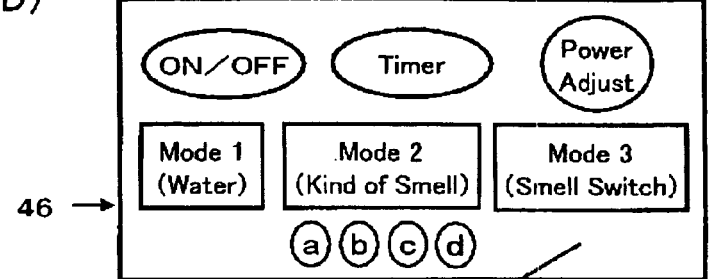
Figure 16:
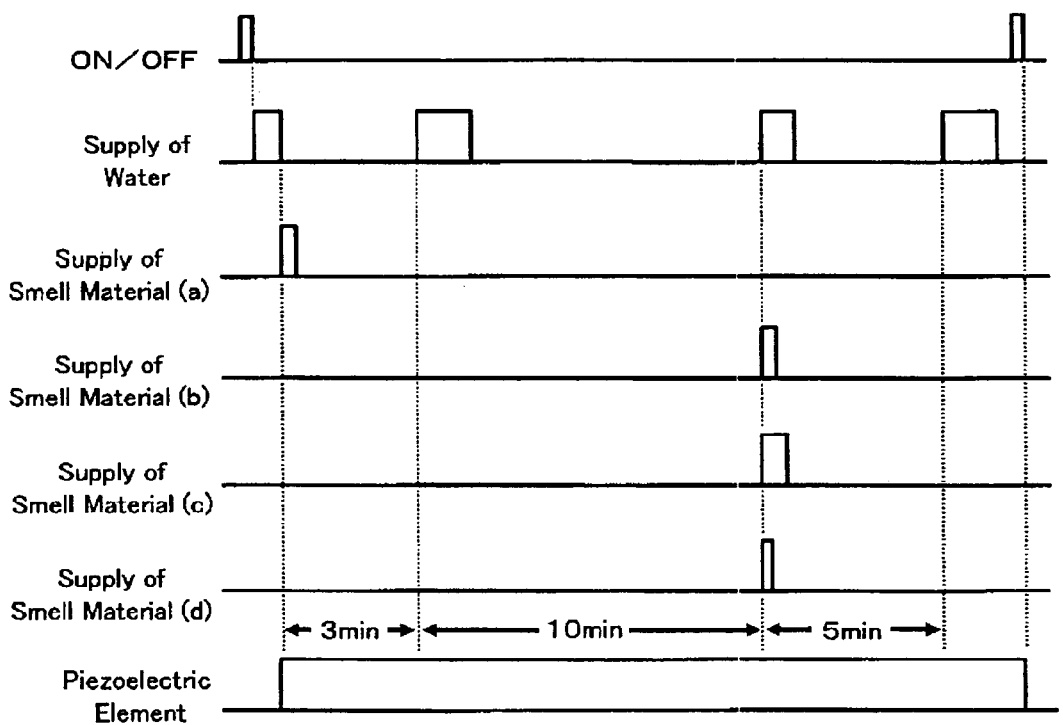

FIG. 16 shows a control method upon switching the perfume-containing mist. FIG. 16(D) is an operation panel of the user operating unit indicated by reference numeral 46 in FIG. 15(A). Mist generation modes can be selected with buttons.

Mode 1 is a mode of generating the mist by putting only water into the small liquid container 20. Mode 2 is a mode of generating the perfume-containing mist by putting water and a specified perfume into the small liquid container 20. When a button a is pushed, the mist which contains the perfume a can be generated. A concentration of aroma can be adjusted according to the amount of perfume to be poured.

Mode 3 is a mode of switching the aroma by automatically changing the type of perfume-containing liquid at an appropriate time. In addition, Power Adjust is a control knob for changing the electric power supplied to the ultrasonic transducer 40 to adjust the amount of atomization. A timer is a switch for controlling an input/output of a power supply at a given time.

FIG. 16(E) shows a specific example of Mode 3. When it is described referring to FIG. 15, operation begins when an ON/OFF switch button is pushed once. The liquid stop valve portion 31 of the liquid passage control mechanism 30 opens, and the water W is poured into the small liquid container 20 from the liquid container 09. The liquid stop valve portion 31 closes at a point when a predetermined amount of water is poured thereinto. When the perfume pouring means 60 operates to pour the perfume a into the small liquid container 20, it will become the perfume-containing liquid Wa.

Here, when the ultrasonic transducer 40 is driven, the mist ma which contains the perfume a is discharged. The perfume-containing liquid Wa is consumed in several minutes (about 3 minutes), and the small liquid container 20 becomes empty.

Subsequently, the liquid passage control unit 30 operates again to thereby pour water into the small liquid container 20. A pouring amount of water is set to be slightly higher as compared with a case where the above-mentioned perfume a has been poured. Since the ultrasonic transducer 40 keeps an operating state, the mist is generated again immediately after pouring water into the small liquid container 20. The mist which contains only water is discharged for a predetermined time (about 10 minutes).

Although aroma is not generated in the meantime, the mist gives proper moisture to air to thereby generate a large amount of negative ion. There is an air freshening effect and also there is an effect of cleaning user's nasal cavity membrane. Thereby, it becomes easy to receive next aroma.

Subsequently, the liquid passage control unit 30 operates to thereby pour water into the small liquid container 20, and the perfume pouring means 60b, 60c, and 60d operate to thereby pour the perfumes b, c, and d into the small liquid container 20. Various perfume-containing liquids can be formed from adjusting a distribution amount of the perfume. This perfume-containing mist is discharged for a predetermined time (about 5 minutes). When the perfume-containing liquid is consumed, it changes to the water mist again, and Mode 3 will be completed when the ON/OFF switch button is pushed on the second time.

It is preferable to set an amount of the perfume-containing liquid poured into the small liquid container 20 to be a small amount that a user enjoys at one time. Here, preferably, the amount which can be enjoyed one time is several times of an atomization time when olfactory fatigue occurs in the same perfume, namely, about several minutes to 10 minutes.

As described above, the perfume-containing liquids having different types, each being small amount, are put into the small liquid container 20 to thereby be atomized, it is possible not only to enjoy various aromas, but also to prevent excess usage of the perfume resulting from carelessness, and thus it is also preferable for health.

Additionally, since the perfume liquid a poured into the small liquid container 20 from the perfume pouring means 60 is consumed little by little, and the remainder is saved without contacting to the open air, it is hard to be degraded and economical. Hence, expensive natural perfumes can be used readily.

In switching of aroma, when a switching time thereof is short, what the physiological action is similar is preferable. For example, when a user would like to increase concentration to thereby reduce mistakes in office or the like, it is effective to switch and use lemon, peppermint, rosemary, and the like, which are said to have clear-headed effects. The same physiological effect can be obtained for a long time, avoiding olfactory fatigue and enjoying different aromas. Meanwhile, when a user would like to feel refreshed, it can also be used while switching to perfumes which differ in physiological and psychological effects.

Ninth Embodiment

FIG. 17(A) is a ninth embodiment of the present invention, and shows a sectional view of the mist generator for discharging the perfume-containing mist in a transverse direction. It is designed to readily enjoy aroma while being floated on a bathtub.

The liquid container 09 for storing water corresponding to the bathtub in the same figure. The hot water W in the bathtub passes the liquid clean filter CL to fill the liquid container 19. The plane of vibration 40F of the ultrasonic transducer 40 is set upward, the small liquid container 20 provided with the ultrasonic transparent film 23 is provided over the plane of vibration 40F, and the liquid for atomization Liq2 (Wa) is stored therein. The method of controlling Liq2 is similar to that of the embodiment shown in FIG. 15.

The ultrasonic concave mirror lens 25 is provided over the small liquid container 20. The hood 251 for making the dispersed liquid collide and drop in the small liquid container 20 is provided on the right-hand side of the ultrasonic concave mirror lens 25, and the ultrasonic reflection tube 27 is fixed to this hood.

Reference numeral 26 represents a mechanism section for adjusting an angle of the ultrasonic concave mirror lens 25. The mechanism section 26 is fixed to the left-hand side of the small liquid container 20 by a supporting mechanism. Reference numeral 201 is a part of the small liquid container 20 and the dispersed liquid collecting mechanism.

The small liquid container 20, the liquid passage control mechanism 30, the perfume pouring means 60, and the ultrasonic concave mirror lens 25 are integrated. Reference numeral 203 represents a mechanism for attaching and detaching the small liquid container 20 to the liquid container 19. Hence, when a portion above the small liquid container 20 is lifted, it can be removed from the container 19.

An operation thereof will be described briefly. The ultrasonic waves emitted from 40F are propagated from Liq1 (W) to Liq2 (Wa) through the ultrasonic transparent film 23, are converged and reflected rightward by the ultrasonic concave mirror lens 25, and disperse Liq2 to then scatter.

Here, what is important for a position and an angle adjustment of the concave mirror lens 25 are to set it to be separated not far from the liquid level but to touch to the liquid level. As a result of this, the ultrasonic waves can efficiently push out the liquid rightward, without losing energy.

Next, the above-mentioned scattered ultrasonic waves travel rightward inside the ultrasonic reflection tube 27 while repeating reflection. Atomization is promoted, and a large amount of mist blows out from a right end of the reflection tube. It is possible to discharge the mist to a distance of about 1 m only by the ultrasonic energy, without using the air flow generating means. The alternate long and short dash line Fg indicates a behavior that the mist is discharged.

The liquid which has not become the mist is made to collide with the hood 251, the dispersed liquid collecting mechanism 201, or the like, and is collected to the small liquid container 20.

FIG. 17(B) is a figure for describing effects of atomizing the liquid by curving the ultrasonic waves in a transverse direction. since the liquid Liq2 pushed out horizontally tried to curve downward by gravity, and the ultrasonic waves tend to travel rightward as indicated by HD, the ultrasonic waves fly out in the air in a point where both traveling directions are shifted, Since the distance Dc until the ultrasonic waves fly out in the air is short compared with a case where Liq2 is pushed up in a vertical direction, the ultrasonic energy is efficiently utilized for atomization to thereby discharge a large amount of mist.

Since a structure in which the concave mirror lens 25, the hood 251, and the ultrasonic reflection tube 27 are integrated is small in size and weight, the angle can be adjusted by manual operation or electric control. When the concave mirror lens 25 is rotated horizontally, the mist can be discharged in the various directions. When the angle is changed vertically, the amount of atomization can be changed. For example, when a reflecting direction of the ultrasonic waves is directed to inside the liquid therebelow in the same figure, mist generation will be stopped.

Reference numeral 85 represents an illuminating device. Light is irradiated in a direction where the mist is discharged in Liq2 (Wa). When an electric lamp is used, it acts also as a heater, and sets Liq2 to be a temperature suitable for atomization or evaporation.

As described above, the present embodiment is the cheap mist generator capable of discharging the mist with easy constitution, which is also compact and efficient. It is possible to enjoy the perfume-containing mist while floating it over the surface of hot water in the bathtub or the like.

Tenth Embodiment

FIG. 18(A) is a tenth embodiment of the present invention, and shows a sectional view of the mist generator capable of atomizing or evaporating medicines or liquors other than perfumes as chemicals to discharge them.

In FIG. 18(A), the ultrasonic transducer 40 provided in the lower housing 06, the liquid container 19 of Liq1, the ultrasonic concave mirror lens 25, and the attachable and detachable mechanism 203 are similar to those described in FIG. 1. Hereinafter, description will be made focusing on different points as compared with FIG. 1.

The ultrasonic reflection tube 27 is provided in the upper part of the small liquid container 20. The small liquid container 20 and the ultrasonic reflection tube 27 can be connected with a fitting mechanism, and integrally used. Moreover, they can be separated for cleaning the inside. A hole for taking air in and pouring the liquid for atomization Liq2 is provided in the upper right portion of the small liquid container 20. Symbol 01k is the liquid pouring means for pouring a liquid Wk which contains perfumes, medicines, or the like, into the small liquid container 20.

A length of the ultrasonic reflection tube 27 is a sufficient length in which the droplet dispersed liquid AK2 is atomized or dropped inside the tube, and is preferable to be 5 cm to 20 cm. The ultrasonic waves travel upward in the tube while repeating reflection. Although the straight tube is used in the same figure, the curved tube 29 as shown in FIG. 4 may be used.

The air discharge tube 80 is provided in the tip of the ultrasonic reflection tube 27. The air discharge tube 80 is curved at the tip thereof and rotatable, and it acts so as not only to discharge the mist or vapor in a predetermined direction, but also to drop the droplet dispersed liquid AK2 when it goes up.

Since a mist mk goes up inside the ultrasonic reflection tube 27 at high speed to be discharged as indicated by the alternate long and short dash line Fg, medical supplies can be taken in when bringing a nasal cavity near the opening of the air discharge tube 80 close.

Further, in order to increase vaporizing efficiency or to increase the ingestion efficiency of medical supplies, heating means HT2 may be provided around the ultrasonic reflection tube 27 to generate an ascending air current due to heat inside the tube, and thus the mist mk may be carried and discharged by the air current. HT2 may be constituted by a cylindrical electric heater, a ceramic heater, or the like. FIG. 18(B) is an external view of HT2.

Additionally, the electric heater HT5 may be provided into the liquid container 19 to thereby warm Liq1, and Liq2 may be warmed and atomized by this heat.

Reference numeral 02 represents an integrated memory circuit for storing attribution information of the liquid Wk to be poured into the small liquid container 20. Reference numeral 03 represents a circuit for supplying electric power to the integrated memory circuit, and also for reading the information therefrom.

The present embodiment does not require the air flow generating means, but has a simple constitution, thus making it possible to be manufactured compactly and at low cost. Since it is rare for the liquid for atomization Liq2 to contact with air, it is suitable for atomization of medical supplies and liquors.

Eleventh Embodiment

FIG. 19(A) is an eleventh embodiment of the present invention, and shows a sectional view of the mist generator for discharging the mist or vapor which contains various chemicals.

In the lower housing 06, the ultrasonic transducer 40 is provided in the center thereof, and it is connected to the rotation angle controlling motor 92. A plurality of ultrasonic concave mirror lenses 25 and 25*b* are provided around the ultrasonic transducer 40. In an upper part of the ultrasonic propagation medium Liq1 (W) which covers the plane of vibration, the integrated structure of the small liquid container 20 and the ultrasonic reflection tube 27 is provided in a direction where the ultrasonic waves reflected by the ultrasonic concave mirror lens 25 travel, and The integrated structure of the small liquid container 20*b* and the ultrasonic reflection tube 27*b* is provided in a direction where the ultrasonic waves reflected by the ultrasonic concave mirror lens 25*b* travel.

FIG. 19(B) shows only the integrated structure while being separated. The ultrasonic transparent film 23 of a concave configuration is provided at a bottom of the small liquid container 20, and the air passage holes Air and a nozzle insertion slot 102 are provided in an upper part thereof.

The nozzle of the liquid container 10 is inserted in the insertion slot. The liquid for atomization Liq2 is poured from the nozzle.

An ultrasonic reflection tube 273 having a plurality of axes for making the ultrasonic waves travel is connected to upper parts of the ultrasonic reflection tubes 27 and 27*b* by a fitting mechanism. The ultrasonic reflection tube 273 can discharge the mist discharged from the ultrasonic reflection tube 27, and the mist discharged from the ultrasonic reflection tube 27*b* from one opening. The ultrasonic reflection tube 273 can be removed if needed.

While a behavior that Liq2 (Wb) is atomized is shown in the same figure, Liq2 (Wb) can be atomized by rotating the ultrasonic transducer 40.

Additionally, while two sets of mist discharge mechanisms are shown in the same figure, still many mist discharge mechanisms can be provided around the ultrasonic transducer.

Since two or more types of chemical-containing liquids are switched at high speed and can be atomized by rotating the ultrasonic transducer 40, the chemicals can be mixed within the ultrasonic reflection tube 273 to be then discharged from the opening.

Twelfth Embodiment

FIG. 20(A) is a twelfth embodiment of the present invention, and shows a sectional view of the mist generator for discharging the mist or vapor which contains various chemicals.

Different points as compared with FIG. 19 will be described. The ultrasonic cylindrical mirror lenses 24 and 24*b* are used for the ultrasonic convergence and reflection mechanism, and the lenses are provided into the liquids for atomization Liq2 (Wa) and Liq2 (Wb) of the small liquid containers 20 and 20*b*, respectively. FIG. 20(B) is an external view of the cylindrical mirror lens 24. The cylindrical mirror lens is set so that the end of the liquid pushed out by the ultrasonic waves may come near the focal point Foc, and it is fixed to the small liquid container.

The ultrasonic transducer 40 is provided so that the plane of vibration may face upward, and the ultrasonic waves are irradiated towards the ultrasonic cylindrical mirror lens 24*b* in Liq2 (Wb) through the ultrasonic transparent film 23*b*, converged and reflected at a reflective surface of the ultrasonic cylindrical mirror lens 24*b*, and disperse Liq2 (Wb) near the focal point Foc of the ultrasonic cylindrical mirror lens 24*b*.

The ultrasonic reflection tube 27*b* is attached to the small liquid container 20*b* so that the lower part thereof may surround the dispersed liquid, and air is taken in from under the tube. Air flows along the path indicated by the alternate long and short dash line Fg, and the mist mb is discharged from an upper part of the ultrasonic reflection tube 27*b*.

By rotating the ultrasonic transducer 40, Liq2 (Wa) can be atomized to thereby discharge the mist ma from an upper part of ultrasonic reflection 27.

Thirteenth Embodiment

FIG. 21 is a thirteenth embodiment of the present invention, and shows a mist generator for discharging the mist or vapor which contains various chemicals. FIG. 21(A) is a longitudinal sectional view of the apparatus. FIG. 21(B) is a top view in a state where the upper housing 04 and the ultrasonic reflection tube are removed in FIG. 21(A). FIG. 21(A)

corresponds to a cross section at the dashed line Sec in FIG. 21(B). Different points will be described although it is similar to FIG. 14.

By using the long axis ultrasonic reflection tube 27, the dispersed liquid collecting mechanism 50 and the air flow generating means 70 are eliminated.

In FIG. 21(A), a buoyancy generating mechanism FLT is provided in the small liquid container. The liquid level G2 of the liquid for atomization Liq2 is set to slightly higher than the liquid level of Liq1. The liquid level G2 is almost constant regardless of a residual amount of Liq2.

A small liquid container coupling mechanism 171 is constituted into a cylindrical-shape so that the small liquid containers 20 and 20b can move up and down.

Heating means HT3 is provided in the upper part of the ultrasonic reflection tube 27. The heating means HT3 has a cylindrical-shape, and is connected to the ultrasonic reflection tube 27 by a fitting mechanism. The bar-shaped moisture-proof heating element YAS is provided in HT3 and an ascending air current is generated by warming the inside of the tube.

As shown in FIG. 21(C), the moisture-proof heating element YAS is composed of a nichrome wire NC and a thermal diffusion filler NC2, which are put into a tubular stainless steel container SUS. NC1 is an electric wiring.

In FIG. 21(B), the four small liquid containers 20, 20b, 20c, and 20d are mounted in the small liquid container coupling mechanism 171, and four types of liquids for atomization Liq2 (Wa, Wb, Wc, Wd) are poured thereinto, respectively.

By rotating the small liquid container coupling mechanism 171 around a medial axis, the chemical-containing mist to be discharged can be switched at high speed.

Fourteenth Embodiment

Figure 23:
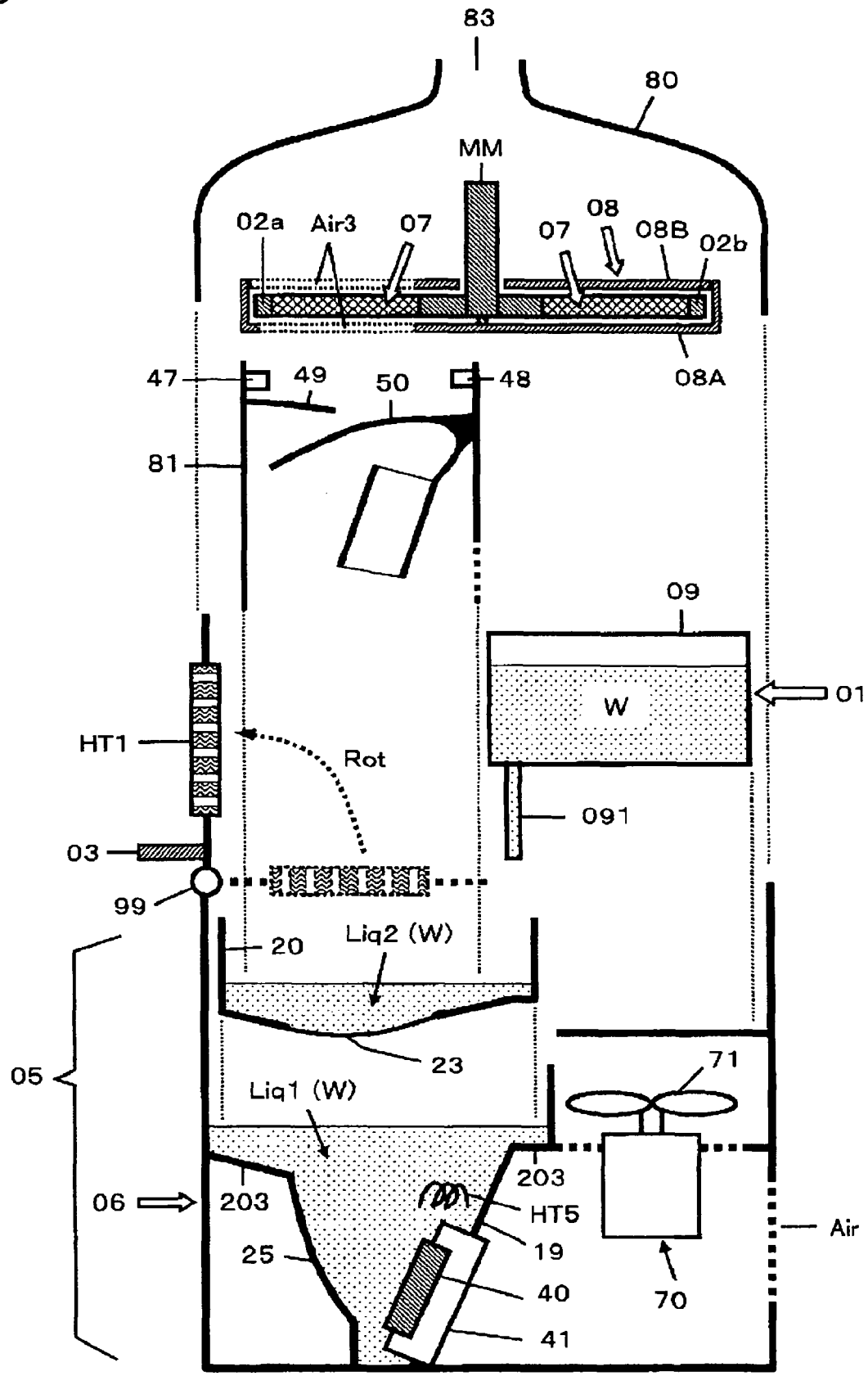

FIG. 22 is a fourteenth embodiment of the present invention, and shows a mist generator for discharging the mist or vapor which contains various chemicals. FIG. 22(A) is a sectional view viewed from the side, FIG. 22(B) is a figure in which a cross section of the chemical occlusion mechanism 07 which is an example of the chemical-containing material is viewed from the top, and FIG. 22(C) is a top view of segmented area selecting case 08. FIG. 23 is an exploded view showing a component constitution.

A basic constitution of the present embodiment will be described. The air flow generating means 70 for sending an air current to the liquid atomization means 05 is provided on the right-hand side of the liquid atomization means 05, the heating means HT1 is provided in an upper part of the liquid atomization means 05, and the chemical occlusion mechanism 07 is provided in an upper part of HT1.

The constitution and operation of the liquid atomization means 05 and the air flow generating means 70 have been described in FIG. 1, they are omitted.

The heating means HT1 provided in the upper part of the air tube 81 will be described. In FIG. 22(A), a lot of air passage holes Air are provided in HT1. Additionally, HT1 can control a heating value by a feeder circuit which is not shown in the same figure.

On the left-hand side of HT1, there is provided a circuit 03 which can supply electric power to an integrated memory circuit 02a which will be described later, and send and receive signals between the integrated memory circuit and this circuit. The HT1 and the circuit 03 can rotate upward about a fulcrum 99.

Next, the chemical occlusion mechanism 07 provided in the upper part of HT1 will be described. The chemical occlusion mechanism 07 is formed into a disk-type and it is divided into six areas by liquid division plates YS, as shown in FIG. 22(B), and six types of chemicals a, b, c, d, e, and f are occluded in the segmented areas, respectively.

While perfumes, medical supplies, pesticides which are less harmful to human bodies, or the like, are applicable as the chemicals to be occluded, a case of occluding the perfume will be hereinbelow described.

The integrated memory circuits 02a 02b, 02c, 02d, 02e, and 02f for storing types, properties, manner of use, relevant information, or the like on the chemicals are provided in segmented areas, respectively. The chemical occlusion mechanism 07 rotates about an axis of rotation MM. When these integrated memory circuits, and the above-mentioned electric power supply and signal transmission/reception circuit 03 are faced to each other upon rotation, the electric power supply and signal transmission/reception circuit 03 can read or write the above-mentioned information while supplying electric power to the integrated memory circuit.

The segmented area selecting case 08 is a segmented area selecting case provided so as to cover the outside of the above-mentioned chemical occlusion mechanism 07, and selectively exposes one of six areas of the chemical occlusion mechanism 07, and shields other areas as shown in FIG. 22(C). Air passage holes Air3 are provided in the selected area.

In the case of use, it is used after integration of housing the chemical occlusion mechanism 07 in a case lower part 08A of the segmented area selecting case 08 to then cover a case lid 08B from a top. The chemical occlusion mechanism 07 put into the case 08 can be attached from or detached to a main body of the apparatus. When it is attached thereto so that the air passage holes Air3 of the above-mentioned case may be located in the upper part of the heating means HT1 as shown in FIG. 22(A), heat of HT1 passes through the holes to be then conducted to a predetermined region of the chemical occlusion mechanism 07.

Next, an operation of discharging the chemicals to be contained in the mist or vapor will be described. A water mist m is generated from Liq2 (W) by an operation of the liquid atomization means 05. By an operation of the air flow generating means 70, the mist passes through the heating means HT1 and the chemical occlusion mechanism 07 along the path indicated by the alternate long and short dash line Fg to finally reach the air discharge tube 80.

In a state where the heating means HT1 is not operated, the air pass holes Air of HT1 and small air passage holes of the chemical occlusion mechanism 07 become a resistance against an air current, so that the mist m tends to be accumulated inside the air discharge tube 80 of an upper part of the chemical occlusion mechanism 07. Meanwhile, even when it is the mist exited from the discharge opening 83, heavy particles tend to drop around the circumference.

Figure 24:
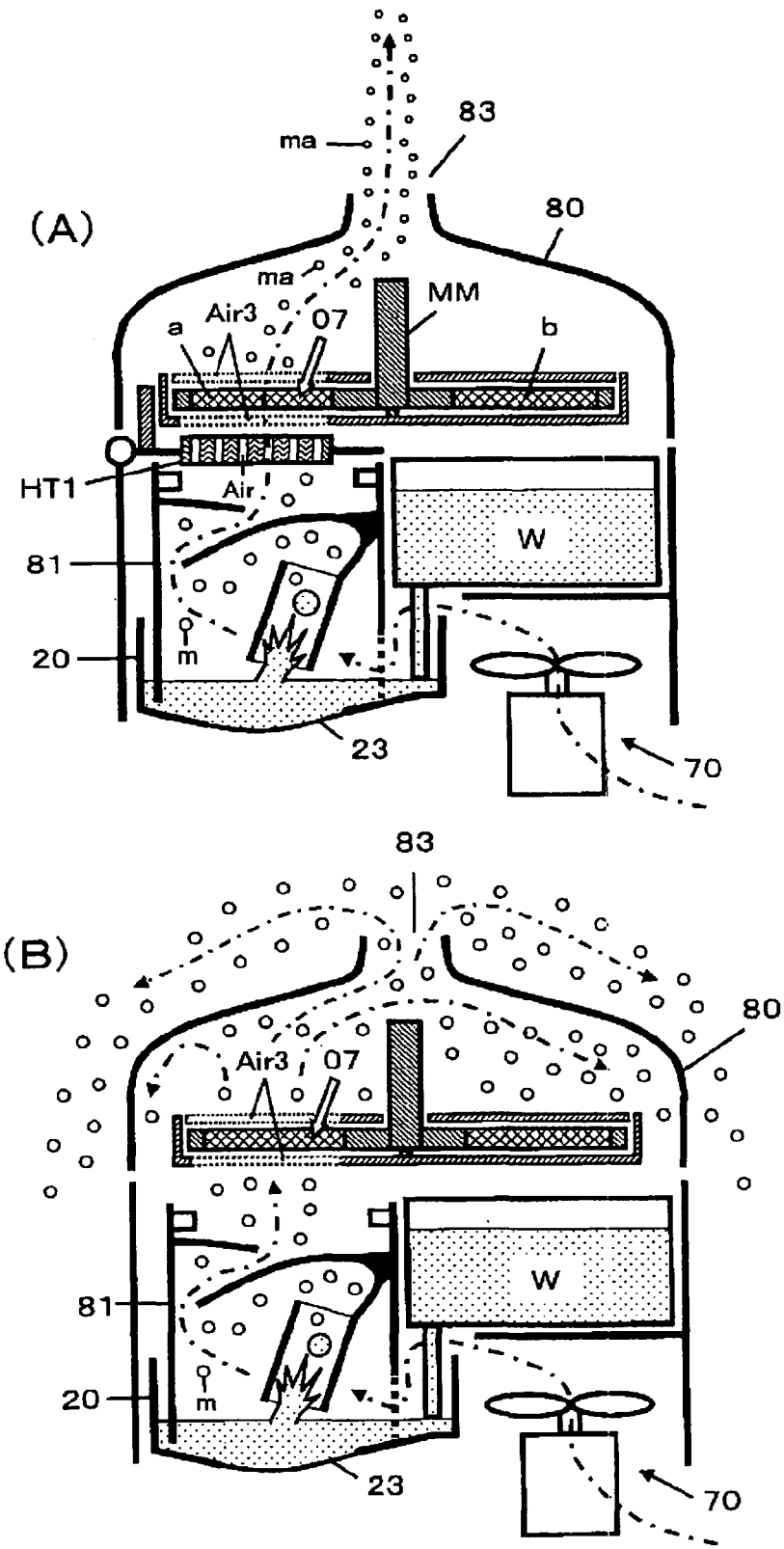

FIG. 24 is for describing effects of the heating means HT1, and FIG. 24(B) shows a case where it is driven while HT1 is omitted. The mist droops around the discharge opening 83. Additionally, when the operation is continued under this state, water will be accumulated in the small air passage holes of the chemical occlusion mechanism 07 to thereby cause clogging, and the mist will no longer be discharged.

Meanwhile, FIG. 24(A) shows a case where HT1 is operated. Air around HT1 is warmed to generate an ascending air current. The mist m passes through the air holes of the chemical occlusion mechanism 07 while being heated. In this case, the mist is promoted in evaporation to be still smaller particles. Meanwhile, the chemicals of the chemical occlusion mechanism 07 are evaporated with the heat, and rise together with the above-mentioned mist. A part of them blends into the water mist m to be the mist ma which contains the chemical a, and rises.

The mist ma comes out of the opening 83 of the air discharge tube 80, and rises almost vertically. After that, it evaporates thoroughly and disappears in an appropriate height. This behavior is similar to that of smoke rising from an incense burner. The behavior that the mist rises while slowly changing into various forms provides the visual healing effects. Naturally, the mist does not drop around the apparatus and does not cause contamination. Moreover, the small air passage holes of the chemical occlusion mechanism 07 are neither clogged. Discharging perfume-containing mist is continued extremely stably.

The chemical occlusion mechanism 07 is heated by the heating means HT1 at about 30 to 50 degrees Centigrade. At 30 degrees Centigrade or less, the ascending air current is not enough, and an amount of evaporation of the chemicals is also small. Hence, the smell characteristics of perfume are not enough. When it is heated at 30 degrees Centigrade or more, preferably at 35 degrees Centigrade or more, the ascending air current with beautiful form will be generated, and the perfume will be evaporated efficiently to emit fragrance.

Meanwhile, when it is heated at 45 to 50 degrees Centigrade or more, movements of the ascending air current are quick and violent, so that the mist looks like smoke when something is burning. Now, there are little healing effects. High visual healing is obtained when the movements of the mist is proportional to an inverse number of the frequency. Namely, it is high when fast repeated movements are included in slow movements as a whole by about an amount proportional to the inverse number of the frequency.

Some perfumes change its nature due to temperature. When it is heated at high temperature, chemical reactions tend to occur, and it may change into another substance. Since many natural perfumes are sensitive to temperature in particularly, temperature controlling is important for them.

Finally, in order to fulfill the aforementioned conditions, it is preferable that the chemical occlusion mechanism 07 is heated in a range of between 30 degrees Centigrade and 50 degrees Centigrade. Passing the mist heated by the heating means HT1 through the air holes of the chemical occlusion mechanism 07 makes it possible to set an exposed portion (portion of Air3) of the chemical occlusion mechanism 07 to a prescribed temperature of between 30 degrees Centigrade to 50 degrees Centigrade.

It should be noted that the above-mentioned temperature is a temperature at the time of heating the chemical-containing material, or a temperature at the time of discharging the mist, and is not a meaning to present it near human organ of smell at this temperature. Since smell characteristics of the human organ of smell will be degraded when the temperature becomes 35 degrees Centigrade or more, it is natural to discharge so as to become a room temperature in front of the tip of the human nose.

The above-mentioned generated mist m acts so as to give moisture to the chemical occlusion mechanism 07. Hence, the chemical is evaporated over a long time, while the concentration thereof is diluted little by little. If the chemical is a perfume, it will be a comfortable aroma felt to be soft with less stimulation when it is discharged while containing moisture. Additionally, since the perfume adheres to the olfactory mucosa more easily when there is a certain amount of humidity, the olfactory sense is efficiently stimulated even by a small amount of perfume. Since this aroma is discharged for a long time, comfortable space is formed. As a result of experiments, the aroma is maintained for a long time by about two to five times as compared with a case of using the ascending air current without moisture.

Although it is necessary to replenish the perfume at a point where the amount of perfume becomes low, this required replenishment frequency is reduced since the perfume is efficiently consumed without waste. Hence, it is economical.

Additionally, upon cleaning the chemical occlusion mechanism 07, since the mechanism is used in a situation where moisture is always provided by the heated mist, it is rare for the chemicals to strongly adhere to the inside thereof, resulting in relatively easy cleaning by washing in cold water or the like.

While there are some steam irons which float and remove the dirt in textiles with steam, it may be thought that the perfume which is occluded into the chemical occlusion mechanism 07 is evaporated while being floated in the present invention based on a similar principle.

What is necessary is just to turn the axis of rotation MM upon switching the type of chemical to be discharged. Preferably, the chemical occlusion mechanism 07 is formed into a thin structure, and constituent materials with high thermal conductivity may be used. When the axis of rotation MM is rotated, a newly heated area will get warm immediately, so that the mist which contains the chemical occluded in this area will be discharged.

Here, a function of the above-mentioned segmented area selecting case 08 will be described. When the chemical of a predetermined area of the chemical occlusion mechanism 07 is evaporated in FIG. 22(A), supposing that there is no segmented area selecting case 08, the heat of the heating means HT1 is conducted to the next area, so that there may be a case where the chemicals in a plurality of areas are mixed to each other. The segmented area selecting case 08 is for solving this problem.

Since areas other than an area which is selected by the segmented area selecting case 08 are shielded as shown in FIG. 22(C), a plurality of chemicals are not mixed to each other. When the chemical occlusion mechanism 07 is rotated, aroma will change, but this switching is clear.

Next, effects of providing the integrated memory circuit in the chemical occlusion mechanism 07 will be described. In FIG. 22(B), six types of chemicals can be stored in the chemical occlusion mechanism 07. In order to replenish six segmented areas with chemicals rightly, a mark is required for users. In the present embodiment, the type of each liquid is stored in the integrated memory circuit, can be read by the electric power supply and signal transmission/reception circuit 03, and can be displayed on the user display unit 46. As a result of this, the user can rightly replenish predetermined chemicals, seeing and confirming the display.

Another effect using the integrated memory circuit is that since the type of chemical occluded in each area of the chemical occlusion mechanism 07 is known, the mist generating means 05 can automatically control the driving method according to the type of chemical. For example, controls to change a heating temperature of the chemical occlusion mechanism 07, or to change the generation amount of mist, or the like are possible according to the type and concentration of the chemical occluded in the chemical occlusion mechanism 07.

Additionally, as described in the embodiment shown in FIG. 1, the five senses presentation information for producing the mist to be discharged is stored in the integrated memory circuits. Presentation of the sensory stimulation corresponding to the physiological and psychological function of aroma will increase the healing effects by a synergetic effect.

When the heating means HT1 is rotated around the fulcrum 99 as indicated by a dashed line arrow Rot shown in FIG. 23, the air tube 81 and the small liquid container 20 can be removed. As described above, the present embodiment provides excellent maintainability because of its easy decomposition.

Since the present invention is the apparatus for providing healing by evaporating the perfumes or the like, there is a fundamental problem if it has a structure which tends to be unsanitary. As described above, a structure which can be simply decomposed to be cleaned is extremely important practically.

In FIG. 22, when the liquid for atomization Liq2 is warmed in advance, it is effective to further generate a large amount of mist. As this means, the heating means HT5 is provided in the liquid container 19 to warm the ultrasonic propagation medium Liq1, thus allowing the heat to warm Liq2 in the small liquid container 20.

In FIG. 22, the air flow generating means 70 and the heating means HT1 have been used in order to generate the flow of the mist, but the flow of the mist can be formed only by HT1. The air flow generating means 70 may be eliminated.

FIG. 25 shows the chemical occlusion mechanism 07 and the peripheral mechanism sections thereof in detail. FIG. 25(A) describes a cross-sectional structure of the chemical occlusion mechanism 07. In addition, FIG. 25(B) is an external view of the heating means HT1.

In the chemical occlusion mechanism 07, reference 95 represents a liquid occlusion plate composed of a reticulated material or a porous material, and holds the liquid chemicals a, b, c, and d dropped from liquid inlets 96 thereinside by the force of surface tension. There are two liquid inlets 96 in each area divided by the liquid division plates YS. The liquid may be poured from either of them. It spreads in a predetermined area of the liquid occlusion plate 95 due to capillarity action.

When the above-mentioned reticulated material 95 is used, several fine-mesh materials which are piled up may be used as the reticulated material 95. It is important that the liquid occlusion plate has a wide liquid occlusion area and does not block the passage of air. When several fine-mesh materials are piled up, a liquid occlusion amount can be increased. As a result of experiments, when 3 to 5 sheets of metallic mesh of No. 50 to No. 120 are used in piles, the liquid perfume can be efficiently occluded.

Reference numerals 93 and 94 are cover plates having a large number of air holes provided so that the liquid occlusion plate 95 may be disposed therebetween. Hence, FIG. 25(A) shows a 3-layer structure, and when several fine-mesh materials are used for the liquid occlusion plate, it will be a structure of about 5 to 7-layer.

The air holes of the above-mentioned cover plates 93 and 94 are constituted so that the inside (liquid occlusion plate side) thereof may be larger and the outside thereof may be smaller. According to such structure, the liquid does not leak outside. Even if a user touches the chemical occlusion mechanism 07 with bare hands, the hands do not become dirty. Handling is extremely easy.

Moreover, a large number of spaces with a small parabolic edge section (indicated by Air in 93 and 94) are formed around the liquid occlusion plate 95, thus resulting in excellent evaporation characteristics. Air is a hole with a diameter of about 1 mm to 3 mm, it may be provided as many as possible so as not to prevent the ascending air current.

The above-mentioned chemical occlusion mechanism 07 and the segmented area selecting case 08 may be materials which do not react to the liquid chemical to be occluded. Aluminum, stainless steel, carbon, or the like may be used. In addition, it may also be constituted by noble metals, such as gold, platinum, or the like. In applying this apparatus as luxury goods such as an electronic incense burner, it becomes a product of rich feeling by constitution of the noble metals.

The heating means HT1 shown in FIG. 25(B) is constituted in such a way that heat-resistant glasses, stones, Chinas, or the like are used for the material to then trench the material, and the nichrome wire NC or the like is wired therein.

Any means which allows air to pass through and the chemical occlusion mechanism 07 provided in the upper part to be warmed at a temperature of between 30 to 50 degrees Centigrade may be used as the heating means HT1. Other than the aforementioned constitution, it can also be constituted by making many holes in a plate-like ceramic heater whose material itself generates heat.

The photo couplers 47 and 48 provided in the air tube 81 shown in FIG. 25(A) are similar to the photo couplers 47 and 48 shown in FIG. 1(A) of the first embodiment, and are for detecting the amount of mist. An output of the ultrasonic transducer 40, the heating means HT1, or the air flow generating means 07 can be appropriately controlled based on this result. It is possible to gradually change the discharge amount of the mist, to gradually change the strength of the aroma, or the like.

FIG. 26 is another embodiment of a chemical-containing material, and a solid perfume with multiple holes 15 and a mechanism section around it are shown in detail. FIG. 26(A) shows a cross-sectional structure of the mechanism section. Additionally, FIG. 26(B) is an external view of the solid perfume with multiple holes. The water mist m which contains the evaporated chemical e is me.

The solid perfume with multiple holes 15 can be produced in such a way that a woody perfume is mashed into a plate-shape using an adhesive, and many holes are made in a surface of the plate. Sandalwoods, sunk woods (chin-boku), or the like can be used as the woody perfume. Although it is similar to production of an incense stick, a point of providing a lot of air pass holes Air so as for the mist to easily pass therethrough is characteristic.

Fifteenth Embodiment

FIG. 27 is a fifteenth embodiment of the present invention, and shows a mist generator for mixing the mist which contains various chemicals with the vapor which contains other chemicals to discharge them. FIG. 27(A) is a sectional view viewed from the side, FIG. 27(B) is a figure in which a cross section of the chemical occlusion mechanism 07 which is an example of the chemical-containing material is viewed from the top, and FIG. 27(C) is a top view of segmented area selecting case 08.

A basic constitution of the present embodiment will be described. A constitution of the liquid atomization means 05 is similar to that of the apparatus shown in FIG. 10. However, the heating means HT1 is provided in the upper part of the ultrasonic reflection tube 29 in the present embodiment. Further, a mechanism for making the mist contain the chemicals is provided in the upper part of HT1, which is similar to that shown in FIG. 22.

The mechanism comprises the chemical occlusion mechanism 07 and the segmented area selecting case 08. However, in the present embodiment, unlike FIG. 22, the segmented area selecting case 08 is connected to the axis of rotation 91, and rotates together with the ultrasonic transducer 40 and the heating means HT1. Additionally, the chemical occlusion mechanism 07 rotates independently of the segmented area selecting case 08 by rotating MM.

An operation of discharging the mist or vapor which contains the chemicals will be described. In FIG. 27(A) the water W is poured into the small liquid container 20, and the water mist m is flowing along a path indicated by the alternate long and short dash line Fg. Since the perfume b is occluded in one area of the chemical occlusion mechanism 07 located over the heating means HT1 as shown in FIG. 27(B), a water mist mb containing the perfume b is discharged.

Here, when the axis of rotation 91 is rotated, the ultrasonic transducer 40, the heating means HT1, and the segmented area selecting case 08 rotate. Here, the chemical occlusion mechanism 07 shall not rotate by the rotation of the axis of rotation 91. The ultrasonic waves atomize the liquid Liq2 in another small liquid container, and the mist passes through another area of the chemical occlusion mechanism 07.

For example, when the axis of rotation 91 is rotated by 180 degrees from a state shown in FIG. 27(A), the ultrasonic waves are irradiated to the liquid of the small liquid container 20b. Since the liquid Wb which contains the perfume b is contained in the small liquid container 20b, the mist mb is generated. Since this mist passes through the area of the chemical occlusion mechanism 07 which occludes the perfume a, the mist or vapor which contains the perfume a and the perfume b is discharged from the opening 83 of the air discharge tube 80.

When the axis of rotation 91, and the axis of rotation MM of the chemical occlusion mechanism 07 are rotated independently, the aroma discharged from one of the perfume-containing liquids in the six small liquid containers and the aroma discharged from one of six types of perfume-containing liquids occluded in the chemical occlusion mechanism 07 can be arbitrarily mixed, so that 30 types of aromas can be switched and discharged, except for the water mist.

HT1 and the chemical occlusion mechanism 07 can be constituted in small size as described above. Hence, when a compact means is used for the means 05 for atomizing the liquid, the apparatus can be constituted in small size as a whole.

Although the chemical-containing materials in FIG. 25 and FIG. 26 have been described that they are all flat-shaped materials, curved plate shape materials may be used. In addition, although the mist is hit to the chemical-containing materials (07, 15) of the flat shape at a right angle in these drawings, the mist may be obliquely hit to the plate. It may be constituted in such a way that the heated mist passes through the plate which contains the chemicals to carry the chemicals.

Although the method for using the ultrasonic waves for the liquid atomization means 05 is shown in the embodiment shown in FIG. 22 or FIG. 27, The mist can also be generated using a principle of atomizers. Moreover, steam obtained by heating water with an electric heater may also be used.

It should be noted that the present invention is not limited to each of above embodiments but can be variously modified without departing the scope thereof in the execution phase. Moreover, the aforementioned embodiments include the inventions at various stages, which may be performed with suitable combinations. Furthermore, the components of each aforementioned embodiment may be suitably omitted based on the object, or may be covered with well-known or commonly-used art.

INDUSTRIAL APPLICABILITY (1) Highly efficient fragrance generator; Since high olfactory stimulation is obtained with a small amount of perfume, high-grade natural perfumes can be used. Preparing a plurality of types of perfumes to present aromas while switching them makes it possible to obtain high healing effects. In addition, since the perfume-containing mist can be discharged toward human organs of smell as a mass, it is possible to present aroma spaces from near locations to distant locations. The healing effects are still higher, when sound and music are generated in accordance with the discharge of the mist or lighting colors are changed. (it is possible in the embodiments of all the drawings)

The fragrance generator is the most suitable for waiting rooms of hospitals where stress alleviation or pain relief are highly requested, guest rooms of hotels, study rooms of children, in which the concentration level is desired to be increased, sport training field where smell of sweat is desired to be refreshed, bedrooms where peaceful sleep is induced, lobbies or conference rooms of airline companies, banks, or the like, which provide services to special customers, or the like. Moreover, it is effective also when producing freshness in places, such as pachinko parlors, where air is dirty.

Meanwhile, although fragrance presentations are conventionally disliked at the foodstuffs-related counters because of disturbance of smells of foods, it is possible to select perfumes to thereby restrictively present aromas in time and in space in the present invention, so that it can be utilized also for the food counters. In order to remove an oily smell in a store which uses much oil, it is effective if the aroma of vanilla is discharged.

(2) Electronic incense burner; When the generated mist is warmed by the heating means (HT1), the mist will rise as a narrow line. This behavior is similar to a behavior that smoke rises when fragrant woods are burnt. The electronic incense burner is safe since fire is not used, and also has excellent smell characteristics. When the outside of the apparatus is ornamented with carpenter carving and porcelain carving, it will be a high-grade electronic incense burner.

In addition, when noble metals, such as gold and platinum, are used for the chemical occlusion mechanism 07 and the segmented area selecting case 08; it will become an electronic incense burner of still more rich feeling. Since noble metals are hard to be corroded, they have excellent smell characteristics. (The embodiments shown in FIG. 8, FIG. 10, FIG. 18, FIG. 21, FIG. 22, and FIG. 27 are suitable in particular.)

(3) Infection preventive air cleaner; There are some natural perfumes having functions to increase immunity force and to fight off viruses. By discharging these as the mist, they can be utilized as infection prevention. For example, aromas of cypresses, lemons, and herbs are effective for prevention of cold. A eucalyptus, peppermint, or the like is effective for hay fever. Since a sodium hypochlorite has a bactericidal action, it may be used for infection prevention when being dissolved in water to be used. It is suitable for the physically weak person's life space, such as a hospital and a home for the aged. In addition, since a large amount of negative ions is generated upon atomization, there are refreshing effects similar to a forest bath. It is possible to interlock with an air-conditioner and a fan-heater (it is possible in the embodiments of all the drawings)

(4) Atmosphere presentation apparatus for visitors; It is a feature of the present invention to have ability of discharging the perfume-containing mist at high speed. It detects entering customers at the entrance of the store or the like to immediately generate aromas, thus allowing a pleasant atmosphere to be produced. In addition, it is the most suitable also as a home fragrance apparatus for entrance. Since the perfume-containing mist is generated shortly after switching on power supply, it can respond also to applications of generating aromas after detecting a visit of guests while interlocking with a door phone. Since the aroma can be focusingly generated on a required time zone, efficient use of the perfumes is possible, so that it is economical. (The embodiments shown in FIG. 1, FIG. 8, FIG. 10, and FIG. 13 are suitable in particular.)

Figure 17:
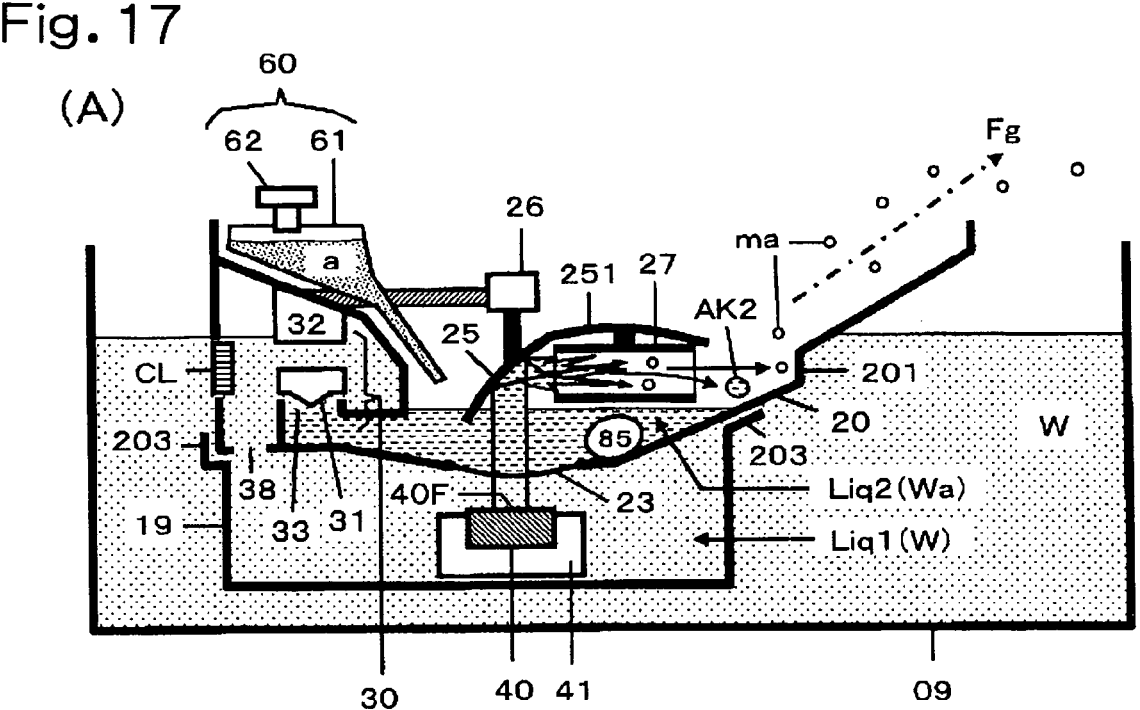
Figure 17:
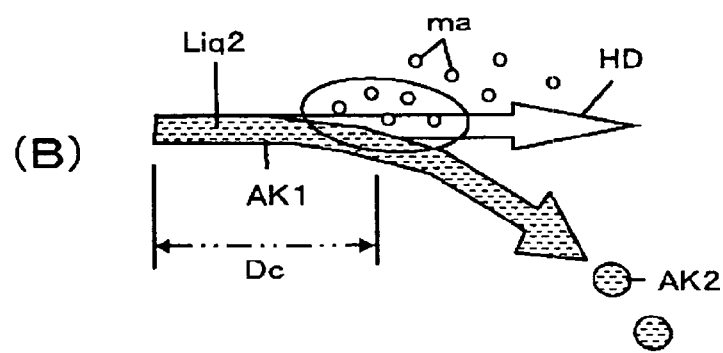

(5) Beauty device; It is effective for the apparatus for generating the mist and vapor which contains perfumes as chemicals to be used in a bathroom or a washroom. Water in the bathtub may also be utilized as the ultrasonic propagation medium (Liq1). The perfume-containing mist floats on the surface of hot water. When a perfume, such as a natural rose or the like, which is traditionally said to have beauty characteristics, is used, components of the essential oil permeate from skin, so that it is effective for cosmetics. Moreover, aromas adhere to hair or the like, so that the mind is fulfilled with the comfortable aroma still after taking a bath. (The embodiments shown in FIG. 15 and FIG. 17 are suitable in particular.)

(6) Aroma generation toilet; This apparatus can also be interlocked with a toilet bowl in a toilet. When a user approaches the toilet bowl, this is detected and aromas are generated. Since the present invention can generate or switch aromas at high speed, fresh aromas can be generated only for using the toilet bowl. In addition, a favorite aroma can also be generated for every user. For example, a chemical which resolves a smell is put into one of the small liquid containers shown in FIG. 10, or one liquid occlusion partition of the chemical occlusion mechanism 07 shown in FIG. 22, a mist generation operation for deodorization is performed, so that an aroma generation operation can be performed thereafter. It will be a clear and comfortable aroma. (The embodiments shown in FIG. 1, FIG. 10, FIG. 13, FIG. 15, FIG. 19, FIG. 22, and FIG. 27 are suitable in particular.)

(7) Aroma generation clock; It can be utilized as a time signal by corresponding a plurality of aromas to time. For example, it is possible to discharge fresh and pleasant wake-up aromas, such as bergamot, lemon, peppermint, coffee, or the like, in the morning, refreshing aromas for increasing the concentration, such as grapefruit, cider wood, or the like, in the daytime, and relaxed aromas, such as lavender, rosewood, sweet orange, or the like, at night. In addition, when aromas in a room are switched in a short time, the aromas will be mixed intricately to thereby form lovely fragrance space. (It is possible in the embodiments of all the drawings.)

(8) Drive support apparatus for automobiles; It can be utilized as a fragrance apparatus for driving support. For example, it is possible to present a perfume of a citrus type with a refreshing function when fatigue is felt during driving, and present a perfume of lavender or the like with a relaxing function when a feeling of irritation is increased due to traffic jams or the like. When it is combined with an apparatus for detecting a nap, it can also present aromas for calling attention to warn. In addition, since this apparatus can control the discharge direction and range of the aroma, it can present a driver's seat, a passenger seat, and a dickey seat an alternative aroma. (The embodiments shown in FIG. 1 and FIG. 13 are suitable in particular.)

(9) Accident prevention alarm apparatus; When a serious disaster is expected due to earthquakes, tidal waves, terrorisms, or the like, aromas can be used as an alarm for informing danger. Accident warning signals for informing the danger are transmitted by the television or radio broadcasting. Upon receiving the signals, a receiving terminal can control the aroma generator employing the present invention to thereby present televiewer the aroma for calling attention. It is effective as means for certainly informing accidents. Meanwhile, in order to restrict the ingress to a dangerous place, it can detect by a sensor that human beings approached the place to then discharge a predetermined aroma to the place, either. (it is possible in the embodiments of all the drawings)

(10) Display unit; This mist generator is placed in a pond of parks or gardens to fill the water surface with the mist. It is possible to enjoy aromas flowing circumferentially while looking at changing mist motions. The healing effects will be further increased when sound and illumination are combined. (The embodiments shown in FIG. 15 and FIG. 17 are suitable in particular.)

(11) Olfactory sense presentation system for adding smells to images or music; Since it is possible to clearly switch aromas at high speed, it can be utilized synchronizing with movies, music, or the like. When a suitable aroma is presented according to the scene change of the contents, presence will be improved. Moreover, it can also be utilized for aroma communication and article introductions in the electronic commerce using the Internet. (The embodiments shown in FIG. 1, FIG. 8, FIG. 10, FIG. 11, FIG. 13, FIG. 19, FIG. 20, FIG. 21, FIG. 22, and FIG. 27 are suitable in particular.)

(12) Medical supplies ingestion apparatus; When it is constituted by integrating the small liquid container 20 and the ultrasonic reflection tube 27 as shown in FIG. 18, it is rare for the liquid for atomization Liq2 therein to contact with the open air, so that it is hard to be contaminated. Hence, medical supplies Wk can be used as the liquid. When the medical supplies are atomized or evaporated to then be absorbed from lungs, it is instantaneously effective. It is suitable for patients who cannot absorb tablets from the stomach and have difficulties in intravenous drip. In addition, the above-mentioned integrated structure can be encapsulated to be thereby disposable. Liquors can also be used instead of the medical supplies. (The embodiments shown in FIG. 18 and FIG. 19 are suitable in particular.)

(13) Insecticide atomizing apparatus; It is possible to put a perfume and an insecticide in the small liquid containers 20 and 20*b* as shown in FIG. 10, for example, to atomizing them while switching. Additionally, the insecticide and the perfume can be occluded in each liquid occlusion partition of the chemical occlusion mechanism 07 shown in FIG. 22 to be used while switching. There are some persons who care about side effects on health, such that the medicine does not suit their constitution when only the insecticide is used to evaporate for a long time, but if the insecticide and the perfume are used while switching, only a necessary minimum insecticide is required, and a change of air is also promoted with the aroma, thus providing comfortable feeling. Naturally, it can also be used by putting only the insecticide therein. (The embodiments shown in FIG. 1, FIG. 10, FIG. 13, FIG. 15, FIG. 19, FIG. 22, and FIG. 27 are suitable in particular.)

(14) Toy for discharging false smoke with smell; A mass of the mist to which a smell of gunpowder is added can be discharged while imitating smoke discharged from a gun in radio control tanks or the like. When launching sound of the gun is reproduced and balls of the mist are discharged, it appeals strongly. Additionally, it can be used also for a locomotive toy. When the mist with a smell imitating smoke is discharged from the chimney, sense of reality will be increased.

(15) Game machine apparatus with smell; In electronic games, it is possible to generate a smell on a scene desired to attract user's concerns. For example, in shooting games, the ball of the mist with a smell is discharged from the gun toward opponents. Since the smell will be felt when the ball collides near a face, struck feeling hit by the ball can be felt. Since it is the vapor ball, it is safe and pleasant.

(16) Smell generating robot; It is applicable also to a healing human-type or animal-type robot. When it approaches human beings to discharge the mist ball with the smell, friendly feelings are increased, thus providing high healing effects.

(17) Noxious animal beat-off apparatus; It is applicable also to beat off bears, monkeys, or the like, which appear human habitations. A perfume that an animal to be beaten off dislikes is mixed in an oily liquid which is hard to evaporate, and a ball of the mist with fetor is discharged. When it hits the animal, the unpleasant smell spreads, and the smell cannot be taken for a while, so that the animal run away and does not try to approach again.

(18) Flame generator; In, for example, FIG. 19, it is possible to pour a perfume-containing alcohol into the small liquid containers 20 and 20b to evaporate the alcohol to be burnt. When the mist which comes out from the tip of the ultrasonic reflection tube 273 is lit, flames will rise. The mist highly rises by the ascending air current due to the flames, and the flames also become high. When the ultrasonic waves are stopped, the flames will also disappear. The flames of various aromas can be generated by changing the type of mist. Moreover, when a medicine whose flame color changes is mixed in the above-mentioned alcohol, the color and the aroma of the flame can be controlled. It will be an attractive interior. (The embodiments shown in FIG. 18 and FIG. 19 are suitable in particular)

In addition to that, applications for forming thin films, applications for cleaning equipment in the body, which is attached to endoscopes, or the like, are possible.

BRIEF DESCRIPTION OF THE DRAWINGS

FIGS. 1A and 1B show a first embodiment that shows a mist generator for atomizing or evaporating various chemical-containing liquids to discharge them to distant locations;

FIG. 1C shows a traveling direction HD of ultrasonic waves reflected by an unltrasonic concave mirror lens of the first embodiment of FIGS. 1A and 1B;

FIG. 2 is an exploded view showing a component constitution in the embodiment;

FIGS. 3A-3C show an enlarged view of the liquid atomization means (05) of the above-mentioned first embodiment;

FIGS. 4A-4C show an improved example of the liquid atomization means (05) of the above-mentioned first embodiment;

FIGS. 5GD1-5GD5 show a second embodiment of the present invention, showing a mist generator using an ultrasonic convergence and reflection mechanism (25) and a long axis ultrasonic reflection mechanism;

FIG. 6 is a drawing for explaining effects of appropriately using an ultrasonic convergence and reflection mechanism (24) and an ultrasonic reflection tube (27);

FIG. 7 is a drawing for explaining problems of the conventional liquid atomization means;

FIGS. 8A-8B show is a third embodiment of the present invention, and shows a mist generator for atomizing or evaporating various chemical-containing liquids to mixingly discharge them to distant locations;

FIG. 9 is an exploded view showing a component constitution in the embodiment;

FIGS. 10A-10B show a fourth embodiment the present invention that shows a mist generator for atomizing or evaporating various chemical-containing liquids to discharge them while switching at high speed;

FIGS. 11A-11B show a fifth embodiment of the present invention that shows a mist generator for atomizing or evaporating various chemical-containing liquids to discharge them while switching at high speed;

FIGS. 12A-12B show a drawing for explaining effects of mounting small liquid containers (20) into which a various chemical-containing liquids are put so that they may be floated on the ultrasonic propagation medium (Liq1) in the embodiment;

FIGS. 13A-13B show a sixth embodiment of the present invention that shows a mist generator for atomizing or evaporating various chemical-containing liquids to discharge them to distant locations while switching at high speed;

FIGS. 14A-14B show a seventh embodiment of the present invention that shows a mist generator for atomizing or evaporating various chemical-containing liquids to discharge them while switching at high speed;

FIGS. 15A-15B show an eighth embodiment of the present invention that shows a mist generator for discharging various chemical-containing mists while controlling the types of chemicals to be poured into the small liquid containers 20;

FIG. 16 is a drawing for explaining a method for controlling switching of the chemical-containing mist in the embodiment;

FIGS. 17A-17B show a ninth embodiment of the present invention that shows a mist generator for readily enjoying aroma in a bathtub or the like;

FIGS. 18A-18B show a tenth embodiment of the present invention that shows a mist generator using medical supplies or liquors as chemicals other than perfumes;

FIGS. 19A-19B show an eleventh embodiment of the present invention that shows a mist generator for atomizing or evaporating various chemical-containing liquids to discharge them while switching at high speed;

FIGS. 20A-20B show a twelfth embodiment of the present invention that shows a mist generator for atomizing or evaporating various chemical-containing liquids to discharge them while switching at high speed;

FIGS. 21A-21C show a thirteenth embodiment of the present invention that shows a mist generator for atomizing or evaporating various chemical-containing liquids to discharge them while switching at high speed;

FIGS. 22A-22C show a fourteenth embodiment of the present invention that shows a mist generator for discharging the mist or vapor which contains various chemicals using a chemical occlusion mechanism (07);

FIG. 23 is an exploded view showing a component constitution in the embodiment;

FIGS. 24A-24B show a drawing for explaining mist discharge effects of heating means;

FIGS. 25A-25B show a drawing for explaining a constitution and operation of the chemical occlusion mechanism (07) which is an example of the chemical-containing material;

FIGS. 26A-26B show a drawing for explaining a constitution and operation of a solid perfume with multiple holes (15) which is an example of the chemical-containing material;

FIGS. 27A-27C show a fifteenth embodiment of the present invention that shows a mist generator for mixing the mist which contains various chemicals with the vapor which contains other chemicals to discharge them; and FIGS. 28A-28B show a conventional typical home ultrasonic mist generator.

EXPLANATIONS OF LETTERS OR NUMERALS

01, 01*a*, 01*b*, 01*c*, 01*k*: liquid pouring means into small liquid container

02, 02*a*, 02*b*, 02*c*, 02*d*, 02*e*, 02*f*: Integrated memory circuit

03, 03*a*, 03*b*, 03*c*: Electric power supply and signal transmission/reception circuit to integrated memory circuit

04: Upper housing

05: Liquid atomization means
06: Lower housing
07: Chemical-containing material using chemical occlusion mechanism (flat plate type)
08: Segmented area selecting case
08A: Case lower part
08B: Lid of case
09: Water container
091: Water pouring nozzle
10, 11, 12, 13: Liquid container for storing chemical-containing liquid
101, 111, 121: Liquid pouring nozzle
102: Nozzle insertion slot
14: Liquid supply port
15: Chemical-containing material using solid perfume with multiple holes
17, 171: Small liquid container coupling mechanism
18: Rotation mechanism
19: Container for pouring liquid so as to fill plane of vibration of ultrasonic transducer
20, 20b, 20c, 20d: Small liquid container with ultrasonic transparent film
201: A part of dispersed liquid collecting mechanism
202: Mounting mechanism for floating small liquid container
203, 204: A part of mechanism for detachably and attachably mounting small liquid container
205: Small liquid container exchanging mechanism
21: Liquid storage
23, 23b: Ultrasonic transparent film
24, 24b: Ultrasonic convergence and reflection mechanism (ultrasonic cylindrical mirror lens)
25, 25b, 25c, 25d, 25e, 25f: Ultrasonic convergence and reflection mechanism (ultrasonic concave mirror lens)
251: Hood-shaped dispersed liquid collecting mechanism
26, 26b: Angle adjustment mechanism of ultrasonic concave mirror lens
27, 27b: Ultrasonic reflection tube (straight tube)
271: Ultrasonic reflection tube (long axis tube)
272: Ultrasonic reflection tube (long axis curved tube)
273: Ultrasonic reflection tube (plural axes type)
28: Ultrasonic reflection tube (ultrasonic cylindrical mirror lens)
29, 29b: Ultrasonic reflection tube (curved tube)
291: mounting part of 29
30: Liquid passage control mechanism
31: Liquid stop valve portion
32: Electromagnet
33, 38: Liquid passage hole
39: Electromagnet drive circuit
40, 40b: Ultrasonic transducer
401: Small ultrasonic transducer
40F: Plane of vibration
41, 41b: Ultrasonic transducer mounting part
43: Drive circuit of ultrasonic transducer
45: Control processing unit
46: User operating unit
47: LED
48: Photo transistor
49, 491: Liquid dispersion preventing mechanism
50, 50b: Dispersed liquid collecting mechanism
51: Mist guide mechanism lower part
52: Mist guide mechanism upper part
58: Mist discharge tube
59: Mist discharge port
60, 60b, 60c, 60d: Chemical (perfume) pouring means
61, 63, 65, 67: Chemical (perfume) container
62, 64, 66, 68: Chemical (perfume) pouring pump
69: Blowing tube
70: Air flow generating means (air blowing blades type)
71: Air blowing blades
72: Motor.
73: Driving device
74: Instant air flow generating means (air gun)
75: Turbinated film for air compression (paraboloidal film)
76: Bellows deformation film
77: Driving solenoid
78: Solenoid drive unit
79: Air blower mechanism
80, 801: Mist discharge tube
81: Air tube
82: Air tube with cave hole
83: Discharge opening of mist or vapor
84: Illumination control means
85, 86: Illumination means
88: Heating means drive circuit
90: Ultrasonic transducer supporting bar
91: Axis of rotation
92: Rotation angle controlling motor
93, 94: Cover plate
95: Liquid occlusion plate
96: Liquid inlet
99: Fulcrum
a, b, c, d, e, f: Chemicals (perfumes)
Air: Air passage hole
Air2: Air passage cave hole
Air3: Air passage hole provided in segmented area selecting case 08
AK1: Column dispersing liquid (liquid column)
AK1C: Liquid dispersion portion
AK2: Droplet dispersed liquid
AK3: Droplet liquid
Audio: Acoustic signal generator
bm: Light beam from light source constituting photo coupler
CL: Liquid clean filter
Dp: Distance from plane of vibration 40F to liquid level of Liq2
Dc: Distance from plane of vibration 40F to liquid dispersion portion
Fg: Discharge passage of mist or vapor
FLT: Buoyancy generating mechanism
Foc: Focal point of ultrasonic convergence and reflection mechanism
G1: Liquid level of Liq1
G2: Liquid level of Liq2
HD, HD1, HD2: Traveling direction of the ultrasonic waves
HT1: Heating means (flat plate type)
HT2: Heating means (tube outside heating type)
HT3: Heating means (tube inside heating type)
HT5: Heating means of liquid for atomization (Liq2) (electric heater)
KE1, KE2: Wave surface of ultrasonic waves
KS: Mixer integrating ultrasonic reflection tube and air tube integrally
KY: Division plate
Liq1: Ultrasonic propagation medium
Liq2: Liquid for atomization
Lm: Annular mist
m: Water mist
ma: Mist which contains chemical (perfume) a
mb: Mist which contains chemical (perfume) b
me: Mist which contains chemical (perfume) e mk: Mist which contains perfume or medical supplies k
MM: Rotation axis of the chemical occlusion mechanism
NC: Nichrome wire
NC1: Wiring
NC2: Thermal diffusion filler
Ray: Light beam
S: Sensor for detecting liquid surface
Sb: Vibration sensor or acoustic sensor
St: Temperature sensor
Sw1, Sw2: Relay contact
SUS: Stainless steel
T1, T2: Height of liquid level
W: Water
Wa, Wb, Wc, Wd: Liquids which contain chemicals (perfumes)
Wk: Liquid which contains perfume or medical supplies k
YAS: Moisture-proof heating element
YS: Liquid division plate

The invention claimed is:

1. A mist generator comprising:
an ultrasonic transducer;
an ultrasonic propagation medium (Liq1) or a liquid for atomization (Liq2) provided so as to fill a plane of vibration of the ultrasonic transducer;
an ultrasonic convergence and reflection mechanism provided in the ultrasonic propagation medium or the liquid for atomization; and
means for discharging a mist outside,
wherein the means for discharging the mist outside uses at least the ultrasonic convergence and reflection mechanism and an ultrasonic reflection tube as components, and the ultrasonic convergence and reflection mechanism has a function for pushing up the liquid for atomization (Liq2) to locally disperse an end thereof, and
wherein the ultrasonic reflection tube is composed of an ultrasonic reflecting material with tube length of 3 cm or more, the tube is kept at a predetermined height from a liquid level of the liquid for atomization so that a lower part of the tube may surround the end of the liquid and a local liquid dispersing portion, and air may enter from the lower part of the tube, and the tube has a mist/liquid separating function for introducing most of ultrasonic waves scattering around the dispersing portion into the tube to convert them into traveling waves in a tube axial direction, the tube carrying the mist by the traveling wave in the axial direction until it passes through the tube, and dropping a droplet liquid from the lower part of the tube.

2. A mist generator comprising:
an ultrasonic transducer;
an ultrasonic propagation medium (Liq1) provided so as to fill a plane of vibration of the ultrasonic transducer;
means for holding a liquid for atomization (Liq2) so that it may contact with the ultrasonic propagation medium;
an ultrasonic convergence and reflection mechanism provided in the ultrasonic propagation medium or the liquid for atomization; and means for discharging a mist outside, wherein
the means for holding the liquid for atomization is composed of a small liquid container with an ultrasonic transparent film,
the means for discharging the mist outside uses at least the ultrasonic convergence and reflection mechanism and an ultrasonic reflection tube as components, and the ultrasonic reflection tube has a function for carrying the mist in an axial direction of the tube by ultrasonic traveling waves generated within the tube until it passes through the tube, and
the small liquid container with the ultrasonic transparent film and the ultrasonic reflection tube are integrally composed, and the integrated structure is detachably and attachably held so that the ultrasonic transparent film may contact with the ultrasonic propagation medium (Liq1).

3. The mist generator according to anyone of claims 1 and 2, wherein the means for discharging the mist outside includes means for detecting a concentration of the mist provided in a mist discharging passage, and instant air flow generating means that is driven upon detecting that the mist concentration becomes higher than a predetermined concentration.

4. The mist generator according to anyone of claims 1 and 2, wherein the means for discharging the mist outside includes means for heating an inside of the ultrasonic reflection tube, or a mist discharging passage coupled with the tube.

5. A mist discharge producing apparatus comprising:
a mist generator including an ultrasonic transducer,
an ultrasonic propagation medium (Liq1) and a liquid for atomization (Liq2) provided so as to fill a plane of vibration of the ultrasonic transducer, wherein ultrasonic waves produced by the ultrasonic transducer travel through the ultrasonic propagation medium to reach the liquid for atomization,
an ultrasonic convergence and reflection mechanism provided in the ultrasonic propagation medium or the liquid for atomization, the ultrasonic convergence and reflection mechanism provided at a slant proximate the ultrasonic transducer,
means for discharging a mist outside, and
means for containing chemicals in the mist, the means is equipped with memory means, and the memory means stores information for producing the mist to be discharged.

6. The mist discharge producing apparatus according to claim 5, wherein the ultrasonic convergence and reflection mechanism is a concave mirror.

* * * * *

UNITED STATES PATENT AND TRADEMARK OFFICE
CERTIFICATE OF CORRECTION

PATENT NO. : 7,934,703 B2
APPLICATION NO. : 11/886020
DATED : May 3, 2011
INVENTOR(S) : Tomono et al.

It is certified that error appears in the above-identified patent and that said Letters Patent is hereby corrected as shown below:

ON THE TITLE PAGE:

Item (86), under "PCT No.", in Column 1, Line 1, delete "PCT/JP2006/004604" and insert -- PCT/JP2006/304604 --, therefor.

Item (56), under "FOREIGN PATENT DOCUMENTS", in Column 2, Line 2, delete "JP 54-082707 7/1979".

Item (56), under "FOREIGN PATENT DOCUMENTS", in Column 2, Line 4, delete "JP U 55-2454 1/1980".

On Page 2, Item (56), under "FOREIGN PATENT DOCUMENTS", in Column 1, Line 1, delete "JP U 58-8034 1/1983".

On Page 2, Item (56), under "FOREIGN PATENT DOCUMENTS", in Column 1, Line 3, delete "JP U 63-198933 12/1988".

On Page 2, Item (56), under "FOREIGN PATENT DOCUMENTS", in Column 1, Line 6, delete "JP U 2-104872 8/1990".

On Page 2, Item (56), under "FOREIGN PATENT DOCUMENTS", in Column 1, Line 8, delete "JP 03-065264 3/1991".

On Page 2, Item (56), under "FOREIGN PATENT DOCUMENTS", in Column 1, Line 11, delete "JP 6-64760 9/1994".

On Page 2, Item (56), under "FOREIGN PATENT DOCUMENTS", in Column 1, Line 12, delete "JP 6-507836 9/1994".

Signed and Sealed this
Eighth Day of May, 2012

David J. Kappos
*Director of the United States Patent and Trademark Office*

CERTIFICATE OF CORRECTION (continued)
U.S. Pat. No. 7,934,703 B2

On Page 2, Item (56), under "FOREIGN PATENT DOCUMENTS", in Column 1, Line 15, delete "JP 07-213968 8/1995".

On Page 2, Item (56), under "FOREIGN PATENT DOCUMENTS", in Column 1, Line 17, delete "JP 7-112491 12/1995".

On Page 2, Item (56), under "FOREIGN PATENT DOCUMENTS", in Column 2, Line 1, delete "JP 09-155260 6/1997".

On Page 2, Item (56), under "FOREIGN PATENT DOCUMENTS", in Column 2, Line 3, delete "JP 2000-176339 6/2000".

On Page 2, Item (56), under "FOREIGN PATENT DOCUMENTS", in Column 2, Line 5, delete "JP 2002-200447 7/2002".

On Page 2, Item (56), under "FOREIGN PATENT DOCUMENTS", in Column 2, Line 7, delete "JP 2003-038646 2/2003".

On Page 2, Item (56), under "FOREIGN PATENT DOCUMENTS", in Column 2, Line 9, delete "JP 2003-245580 9/2003".

On Page 2, Item (56), under "FOREIGN PATENT DOCUMENTS", in Column 2, Line 10, delete "JP 2003-266034 9/2003".

On Page 2, Item (56), under "FOREIGN PATENT DOCUMENTS", in Column 2, Line 12, delete "JP U 3100873 1/2004".

On Page 2, Item (56), under "FOREIGN PATENT DOCUMENTS", in Column 2, Line 14, delete "JP 2004-159875 6/2004".

On Page 2, Item (56), under "FOREIGN PATENT DOCUMENTS", in Column 2, Line 16, delete "JP 2004-236508 8/2004".

IN THE SPECIFICATIONS:

In Column 1, Line 24, delete "c~n" and insert -- can --, therefor.

In Column 4, Line 26, delete "2002-200447" and insert -- 2002-200447. --, therefor.

In Column 9, Line 24, delete "mist," and insert -- mist. --, therefor.

In Column 27, Line 61, delete "high," and insert -- high --, therefor.

In Column 33, Line 8, delete "(GD2)" and insert -- (GD2), --, therefor.

CERTIFICATE OF CORRECTION (continued)
U.S. Pat. No. 7,934,703 B2

In Column 33, Line 38, delete "like" and insert -- like. --, therefor.

In Column 38, Line 33, delete "Example" and insert -- Embodiment --, therefor.

In Column 40, Line 52, delete "Example" and insert -- Embodiment --, therefor.

In Column 48, Line 19, delete "shifted," and insert -- shifted. --, therefor.

In Column 57, Line 2, delete "27(A)" and insert -- 27(A), --, therefor.

In Column 58, Line 8, delete "drawings)" and insert -- drawings.) --, therefor.

In Column 58, Line 56, delete "drawings)" and insert -- drawings.) --, therefor.

In Column 60, Line 2, delete "drawings)" and insert -- drawings.) --, therefor.

In Column 61, Line 25, delete "particular)" and insert -- particular.) --, therefor.

In Column 61, Line 60, delete "embodiment the" and insert -- embodiment of the --, therefor.